(12) United States Patent
Tsuboi et al.

(10) Patent No.: US 10,913,724 B2
(45) Date of Patent: Feb. 9, 2021

(54) PRODUCTION METHOD FOR AMIDATE COMPOUND

(71) Applicant: KOEI CHEMICAL COMPANY, LIMITED, Chiba (JP)

(72) Inventors: Hitomi Tsuboi, Chiba (JP); Motoyoshi Miyagi, Chiba (JP); Shingo Nitta, Chiba (JP); Shogo Takahashi, Chiba (JP)

(73) Assignee: KOEI CHEMICAL COMPANY, LIMITED, Chiba (JP)

( * ) Notice: Subject to any disclaimer, the term of this patent is extended or adjusted under 35 U.S.C. 154(b) by 0 days.

(21) Appl. No.: 16/497,997

(22) PCT Filed: Mar. 29, 2018

(86) PCT No.: PCT/JP2018/013332
§ 371 (c)(1),
(2) Date: Sep. 26, 2019

(87) PCT Pub. No.: WO2018/181753
PCT Pub. Date: Oct. 4, 2018

(65) Prior Publication Data
US 2020/0024237 A1 Jan. 23, 2020

(30) Foreign Application Priority Data
Mar. 31, 2017 (JP) ................. 2017-072941

(51) Int. Cl.
*C07D 233/90* (2006.01)
(52) U.S. Cl.
CPC ................. *C07D 233/90* (2013.01)
(58) Field of Classification Search
None
See application file for complete search history.

(56) References Cited

U.S. PATENT DOCUMENTS

| | | | |
|---|---|---|---|
| 2011/0046301 A1 | 2/2011 | Mignani et al. | |
| 2019/0177464 A1 | 6/2019 | Miyagi et al. | |

FOREIGN PATENT DOCUMENTS

| | | |
|---|---|---|
| JP | 5-45763 | 2/1993 |
| JP | 2013-526630 | 6/2013 |
| SG | 185398 | 12/2012 |
| WO | 2009/013344 | 1/2009 |
| WO | 2018/025970 | 2/2018 |

OTHER PUBLICATIONS

Baiocchi et al., "1,2,4-Oxadiazoles. XI (1). An Intermediate in the Isomerization from Nitrones to Amides", J. Heterocyclic Chem., vol. 16, pp. 1477-1481 (1979).

Temprado et al., "Synthesis, structure, and thermochemistry of adduct formation between N-heterocyclic carbenes and isocyanates or mesitylnitrile oxide", Struct Chem, vol. 24, pp. 2059-2068 (2013).
Extended European Search Report dated Feb. 7, 2020 in European Patent Application No. 17837071.4.
International Search Report dated Sep. 12, 2017 in International (PCT) Application No. PCT/JP2017/028314.
Sturada et al., "Electron-Deficient Heteroarenium Salts: An Organocatalytic Tool A for Activation of Hydrogen Peroxide in Oxidations", Journal of Organic Chemistry, vol. 80, No. 5, 2015, pp. 2676-2699, ISSN:0022-3263.

(Continued)

*Primary Examiner* — Samantha L Shterengarts
(74) *Attorney, Agent, or Firm* — Wenderoth, Lind & Ponack, L.L.P.

(57) ABSTRACT

A method for producing an amidate compound represented by Formula (3), comprising reacting a urethane compound represented by Formula (1) with a carboxylate compound represented by Formula (2):

Formula (1)

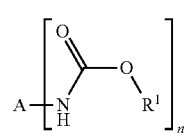

(1)

Formula (2)

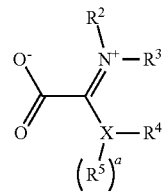

(2)

Formula (3)

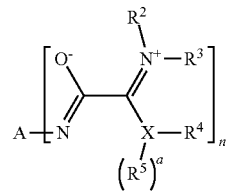

(3)

(in the formulas, A, n, $R^1$, $R^2$, $R^3$, $R^4$, $R^5$, $R^6$, X, and a are as described in the Description).

9 Claims, No Drawings

(56) References Cited

OTHER PUBLICATIONS

Schmidt et al., "Imidazol-2-and-4-ylidene by decarboxylation. Studies on the cross-conjugated mesomeric betaine-alkaloid norzooanemonine and its pseudo-cross-conjugated isomer", Organic & Biomolecular Chemistry, vol. 6, No. 2, 2008, pp. 287-295, ISSN:1477-0520.

Coutelier et al., "N-Heterocyclic Carbene-Catalyzed Synthesis of Polyurethanes", Polymer Preprints, vol. 52, No. 2, 2011, pp. 290-291.

Bantu et al., "$CO_2$, Magnesium, Aluminum, and Zinc Adducts of N-Heterocyclic Carbenes as (Latent) Catalysts for Polyurethane Synthesis", European Journal of Inorganic Chemistry, No. 13, 2009, pp. 1970-1976, ISSN: 1434-1948.

Bantu et al., "$CO_2$ and $Sn^{II}$ adducts of N-Heterocyclic Carbenes as Delayed-Action Catalysts for Polyurethane Synthesis", Chemistry—A European Journal, vol. 15, No. 13, 2009, pp. 3103-3109, ISSN:0947-6539.

Winkler et al., "Preparation and reactivity of an isolable N-heterocyclic carbene-borane", Journal of Organometallic Chemistry, vol. 775, 2015, pp. 164-168, ISSN: 0022-328X.

Li et al., "Amine-Linked N-Heterocyclic Carbenes: The Importance of an Pendant Free Amine Auxiliary in Assisting the Catalytic Reaction", Chemistry—An Asian Journal, vol. 6, No. 6, 2011, pp. 1520-1524, ISSN:1861-4728.

Wang et al., "High-Spin Iron(II) Alkynyl Complexes with N-Heterocyclic Carbene Ligation: Synthesis, Characterization, and Reactivity Study", Organometallics, vol. 4, No. 12, 2015, pp. 2775-2782, ISSN:0276-7333.

"Structure and physical properties of polyurethane, and higherfunction and application development" Technical InformationInstitute Co., Ltd., 1998, p. 325, with partial English translation.

Coutalier et al., "N-Heterocyclic carbene-catalysed synthesis of polyurethanes", Polymer Chemistry, vol. 3, 2012, pp. 605-608.

International Search Report dated Jul. 3, 2018 in International (PCT) Application No. PCT/JP2018/013332.

PRODUCTION METHOD FOR AMIDATE COMPOUND

TECHNICAL FIELD

The present invention relates to a method for producing an amidate compound.

BACKGROUND ART

Among coordination unsaturated compounds collectively referred to as carbene compounds, heterocyclic carbene compounds (NHCs) have recently attracted attention as catalysts. For example, heterocyclic carbene compounds are known to be used as catalysts for producing polymers having a polyether structure by ring-opening polymerization of alkylene oxides, such as epoxy compounds (Patent Literature (PTL) 1 and Patent Literature (PTL) 2)); and as catalysts for a polymerization reaction of an aliphatic diisocyanate and an aliphatic diol (Non-patent Literature (NPL) 1). However, carbene compounds are generally unstable to oxygen and water. Therefore, as carbene-stabilized compounds, for example, carbon dioxide adducts of heterocyclic carbene compounds (hereinafter referred to as carboxylate compounds) or isocyanate adducts of heterocyclic carbene compounds (hereinafter referred to as amidate compounds) are known (Non-patent Literature (NPL) 2).

Among these, as a method for producing an amidate compound, for example, a method comprising reacting p-chlorophenyl isocyanate with 1,3-dimethylimidazolium-2-carboxylate is known (NPL 2). With reference to the production method disclosed in NPL 2, the present inventors attempted to react diphenylmethane diisocyanate with 1,3-dimethylimidazolium-2-carboxylate to obtain an amidate compound having two amidate groups. However, due to complicated reactions, the inventors were unable to produce the desired product (see the Comparative Examples described below). Thus, the production method disclosed in NPL 2 is unsatisfactory in term of producing an amidate compound having multiple amidate groups. Accordingly, it has been a challenge to develop an amidate compound production method that is applicable to a wide range of substrates, the method being capable of producing an amidate compound having amidate groups, as well as an amidate compound having one amidate group.

CITATION LIST

Patent Literature

PTL 1: WO2009/013344
PTL 2: JP2013-526630A

Non-Patent Literature

NPL 1: Polymer Chemistry, 2012, Vol. 3, pp. 605 to 608
NPL 2: Organic & Biomolecular Chemistry, 2008, Vol. 6, No. 2, pp. 287 to 295

SUMMARY OF INVENTION

Technical Problem

The present invention was made in view of the above background art. An object of the present invention is to provide an amidate compound production method that is applicable to a wide range of substrates, the method being capable of producing a compound having amidate groups, as well as a compound having one amidate group.

Solution to Problem

The present inventors conducted extensive research to solve the above problem, and found that an amidate compound represented by Formula (3) below can be produced by reacting a urethane compound represented by Formula (1) below with a carboxylate compound represented by Formula (2) below. The present invention has thus been accomplished.

More specifically, the present invention includes the following [1] to [9].

[1] A method for producing an amidate compound, comprising reacting a urethane compound with a carboxylate compound, the urethane compound being represented by Formula (1):

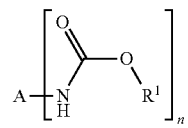

(wherein $R^1$ represents a hydrocarbon group that may contain a heteroatom; A represents a substituted or unsubstituted hydrocarbon group; and n is an integer of 1 or more), the carboxylate compound being represented by Formula (2):

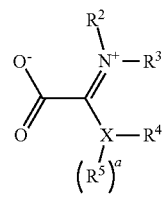

(wherein $R^2$, $R^3$, $R^4$ and $R^5$ each represent a hydrocarbon group that may contain a heteroatom; some or all of $R^2$, $R^3$, $R^4$, and $R^5$ may be bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom; and the amidate compound being represented by Formula (3):

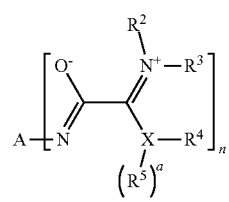

(wherein A, n, $R^2$, $R^3$, $R^4$, $R^5$, X, and a are as defined above).
[2] The method for producing an amidate compound according to [1], wherein the urethane compound represented by Formula (1) is a urethane compound represented by any one of the following Formulas (1-1), (1-2), and (1-3):

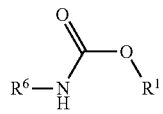
(1-1)

(wherein $R^6$ represents a substituted or unsubstituted hydrocarbon group; and $R^1$ is as defined above);

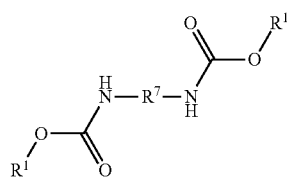
(1-2)

(wherein $R^7$ represents a substituted or unsubstituted hydrocarbon group; and $R^1$ is as defined above); and

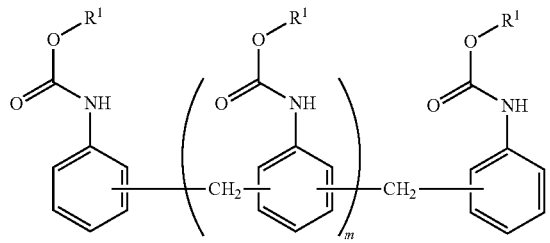
(1-3)

(wherein m is an integer of 0 to 4; and $R^1$ is as defined above).

[3] The method for producing an amidate compound according to [1], wherein the urethane compound represented by Formula (1) is obtained by reacting an amine compound with a carboxyl compound, and the obtained urethane compound represented by Formula (1) is then reacted with the carboxylate compound represented by Formula (2), the amine compound being represented by Formula (4):

$$A\text{―}[NH_2]_n \quad (4)$$

(wherein A and n are as defined above), and the carboxyl compound being represented by any one of the following Formulas (5a), (5b), and (5c):

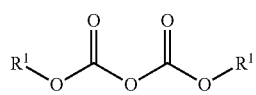
(5a)

(wherein $R^1$ is as defined above);

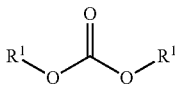
(5b)

(wherein $R^1$ is as defined above); and

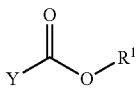
(5c)

(wherein $R^1$ is as defined above; and Y represents a halogen atom).

[4] The method for producing an amidate compound according to [3], wherein the carboxyl compound is a carboxyl compound represented by Formula (5a).

[5] The method for producing an amidate compound according to [3] or [4], wherein the amine compound is an amine compound represented by any one of the following Formulas (4-1), (4-2), and (4-3):

$$R^6\text{―}NH_2 \quad (4\text{-}1)$$

(wherein $R^6$ is as defined above);

$$H_2N\text{―}R^7\text{―}NH_2 \quad (4\text{-}2)$$

(wherein $R^7$ is as defined above); and

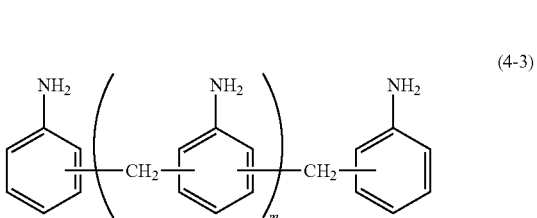
(4-3)

(wherein m is as defined above).

[6] The method for producing an amidate compound according to [1] or [2], wherein the urethane compound represented by Formula (1) is obtained by reacting an isocyanate compound with an alcohol compound, and the obtained urethane compound represented by Formula (1) is then reacted with the carboxylate compound represented by Formula (2), the isocyanate compound being represented by Formula (6):

$$A\text{―}[NCO]_n \quad (6)$$

(wherein A and n are as defined above), and the alcohol compound being represented by Formula (7):

$$R^1\text{―}OH \quad (7)$$

(wherein $R^1$ is as defined above).

[7] The method for producing an amidate compound according to [6], wherein the isocyanate compound represented by Formula (6) is an isocyanate compound represented by any one of the following Formulas (6-1), (6-2), and (6-3):

$$R^6\text{―}NCO \quad (6\text{-}1)$$

(wherein $R^6$ is as defined above);

$$OCN\text{―}R^7\text{―}NCO \quad (6\text{-}2)$$

(wherein $R^7$ is as defined above); and

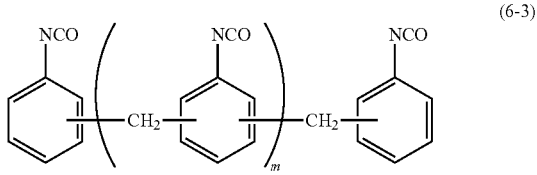

(6-3)

(wherein m and $R^1$ are as defined above).

[8] The method for producing an amidate compound according to any one of [1] to [7], wherein the carboxylate compound represented by Formula (2) is a carboxylate compound represented by any one of the following Formulas (2-1), (2-2), and (2-3):

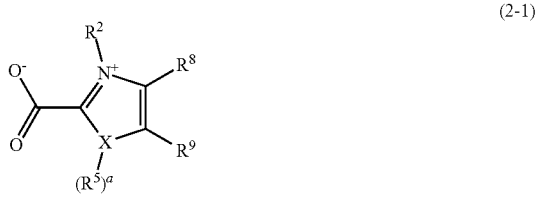

(2-1)

(wherein $R^2$, $R^5$, X, and a are as defined above; and $R^8$ and $R^9$ represent a hydrogen atom, or a $C_1$-$C_6$ hydrocarbon group that may contain a heteroatom);

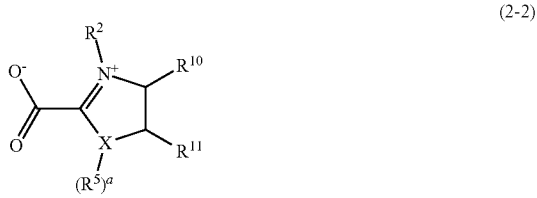

(2-2)

(wherein $R^2$, $R^5$, X, and a are as defined above; $R^{10}$ and $R^{11}$ represent a hydrogen atom, or a $C_1$-$C_6$ hydrocarbon group that may contain a heteroatom); and

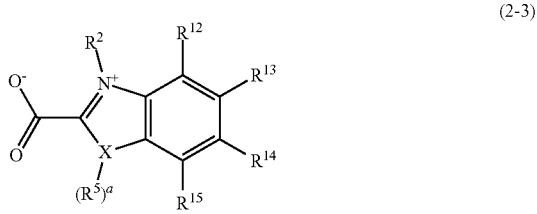

(2-3)

(wherein $R^2$, $R^5$, X, and a are as defined above; $R^{12}$, $R^{13}$, $R^{14}$, and $R^5$ each represent a hydrogen atom, or a $C_1$-$C_6$ hydrocarbon group that may contain a heteroatom).

[9] The method for producing an amidate compound according to any one of [1] to [8], wherein X is a nitrogen atom.

Advantageous Effects of Invention

According to the present invention, there can be provided a novel method for producing an amidate compound, which is applicable to a wide range of substrates, the method being capable of producing an amidate compound having amidate groups, as well as an amidate compound having one amidate group.

DESCRIPTION OF EMBODIMENTS

Embodiments of the present invention are described in detail below.

In Formula (1), $R^1$ is a hydrocarbon group that may contain a heteroatom, preferably a $C_1$-$C_{50}$ hydrocarbon group that may contain a heteroatom, more preferably a $C_1$-$C_{30}$ hydrocarbon group that may contain a heteroatom, and particularly preferably a $C_1$-$C_8$ hydrocarbon group that may contain a heteroatom. Examples of the hydrocarbon group that may contain a heteroatom include methyl, ethyl, propyl, isopropyl, n-butyl, s-butyl, t-butyl, n-pentyl, n-hexyl, n-octyl, n-decyl, n-dodecyl, allyl, benzyl, cyclohexyl, adamantyl, phenyl, 2,6-diisopropylphenyl, 2,4,6-trimethylphenyl, 2-methoxyethyl, 2-ethoxyethyl, 2-(dimethylamino)ethyl, and the like; preferably methyl, ethyl, propyl, isopropyl, t-butyl, n-octyl, cyclopentyl, cyclohexyl, and 2,4,6-trimethylphenyl; more preferably methyl, ethyl, isopropyl, t-butyl, n-octyl, and phenyl; and particularly preferably methyl, isopropyl, t-butyl, n-octyl, and phenyl.

A is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group.

When A is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro, cyano, sulfonyl, isocyanate, and like groups. The hydrocarbon group represented by A may be substituted with a heteroatom, such as oxygen, nitrogen, or sulfur. When the hydrocarbon group A is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include a phenyl group, a naphthyl group, and the like.

The number of substituents can be 1 to 5, preferably 1 to 3, and more preferably 1 or 2.

n is an integer of 1 or more. In view of ease of availability, n is preferably 1 to 6, more preferably 1 to 4, and particularly preferably 1 to 2.

In the present invention, the urethane compound represented by Formula (1) (hereinafter referred to as urethane compound (1)) is preferably a urethane compound represented by any one of Formulas (1-1), (1-2), and (1-3), and particularly preferably a urethane compound represented by Formula (1-1) or Formula (1-2).

In Formula (1-1), $R^1$ is as defined above. $R^6$ is a substituted or unsubstituted hydrocarbon group, preferably a substituted or unsubstituted $C_1$-$C_{50}$ hydrocarbon group, more preferably a substituted or unsubstituted $C_1$-$C_{30}$ hydrocarbon group, and particularly preferably a substituted or unsubstituted $C_1$-$C_{12}$ hydrocarbon group. Specific examples include methyl, ethyl, propyl, isopropyl, n-butyl, s-butyl, t-butyl, n-pentyl, n-hexyl, n-heptyl, n-decyl, n-dodecyl, n-octadecyl, cyclopropyl, cyclopentyl, cyclohexyl, phenyl, naphthyl, benzyl, phenethyl, tolyl, allyl, and the like; and preferably benzyl and phenyl.

When $R^6$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro, cyano, sulfonyl, isocyanate, and like groups. The hydrocarbon group represented by $R^6$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include phenyl, naphthyl, and like groups.

The number of substituents can be 1 to 5, preferably 1 to 3, and more preferably 1 or 2.

In Formula (1-2), $R^1$ is as defined above. $R^7$ is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group. Specific examples include alkylene groups, such as methylene, dimethylmethylene, ethylene, n-propylene, n-butylene, n-pentylene, n-hexylene, n-heptylene, n-octylene, n-nonylene, n-decylene, n-dodecylene, n-octadecylene, and cyclohexylene; arylene groups, such as phenylene, 2-methylphenylene, 2,6-dimethylphenylene, 2,4-dimethylphenylene, 2,3-dimethylphenylene, and naphthylene; arylalkylene groups, such as phenylmethylene, phenylethylene, 1-phenylpropylene, 2-phenylpropylene, 1-phenylbutylene, 2-phenylbutylene, naphthylmethylene, and naphthylethylene; arylenealkylene groups obtained by suitably combining the above alkylene groups and arylene groups; and the like. These divalent hydrocarbon groups may be repeated or combined to constitute one divalent hydrocarbon group.

When $R^7$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro, cyano, sulfonyl, isocyanate, and like groups. The hydrocarbon group represented by $R^7$ may be substituted with a heteroatom, such as oxygen, nitrogen, or sulfur. When a hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include phenyl, naphthyl, and like groups.

The number of substituents can be 1 to 5, preferably 1 to 3, and more preferably 1 or 2.

In Formula (1-3), m is an integer of 0 to 4, and $R^1$ is as defined above.

Specific examples of the urethane compound (1) are shown below. However, the present invention is not limited thereto. In the specific examples below, Et represents ethyl, Pr represents n-propyl, and Bu represents n-butyl.

$$R-\underset{H}{N}-\overset{O}{\underset{\|}{C}}-O-R'$$

| R | R' | |
|---|---|---|
| $CH_3$ | $CH_3$ | (1-1-1p) |
| Et | $CH_3$ | (1-1-2p) |
| Pr | $CH_3$ | (1-1-3p) |
| $CH(CH_3)_2$ | $CH_3$ | (1-1-4p) |
| Bu | $CH_3$ | (1-1-5p) |
| $C(CH_3)_3$ | $CH_3$ | (1-1-6p) |
| $(CH_2)_4CH_3$ | $CH_3$ | (1-1-7p) |
| $(CH_2)_5CH_3$ | $CH_3$ | (1-1-8p) |
| $(CH_2)_7CH_3$ | $CH_3$ | (1-1-9p) |
| $(CH_2)_{11}CH_3$ | $CH_3$ | (1-1-10p) |
| $(CH_2)_{17}CH_3$ | $CH_3$ | (1-1-11p) |
| allyl | $CH_3$ | (1-1-12p) |
| cyclopropylmethyl | $CH_3$ | (1-1-13p) |
| cyclopentylmethyl | $CH_3$ | (1-1-14p) |
| cyclohexylmethyl | $CH_3$ | (1-1-15p) |
| adamantylmethyl | $CH_3$ | (1-1-16p) |
| $CH(CH_3)CH_2Cl$ | $CH_3$ | (1-1-17p) |
| $CH(CH_2Cl)_2$ | $CH_3$ | (1-1-18p) |

-continued

R—NH—C(=O)—O—R'

| R | R' | |
|---|----|--|
| -(CH₂)₄-Cl (branched) | CH₃ | (1-1-19p) |
| CH₃ | CH(CH₃)₂ | (1-1-1q) |
| Et | CH(CH₃)₂ | (1-1-2q) |
| Pr | CH(CH₃)₂ | (1-1-3q) |
| CH(CH₃)₂ | CH(CH₃)₂ | (1-1-4q) |
| Bu | CH(CH₃)₂ | (1-1-5q) |
| C(CH₃)₃ | CH(CH₃)₂ | (1-1-6q) |
| (CH₂)₄CH₃ | CH(CH₃)₂ | (1-1-7q) |
| (CH₂)₅CH₃ | CH(CH₃)₂ | (1-1-8q) |
| (CH₂)₇CH₃ | CH(CH₃)₂ | (1-1-9q) |
| (CH₂)₁₁CH₃ | CH(CH₃)₂ | (1-1-10q) |
| (CH₂)₁₇CH₃ | CH(CH₃)₂ | (1-1-11q) |
| allyl | CH(CH₃)₂ | (1-1-12q) |
| cyclopropylmethyl | CH(CH₃)₂ | (1-1-13q) |
| cyclopentylmethyl | CH(CH₃)₂ | (1-1-14q) |
| cyclohexylmethyl | CH(CH₃)₂ | (1-1-15q) |
| adamantylmethyl | CH(CH₃)₂ | (1-1-16q) |
| -CH₂Cl (branched) | CH(CH₃)₂ | (1-1-17q) |
| -(CH₂)₂Cl (branched) | CH(CH₃)₂ | (1-1-18q) |
| -(CH₂)₄Cl (branched) | CH(CH₃)₂ | (1-1-19q) |
| CH₃ | C(CH₃)₃ | (1-1-1r) |
| Et | C(CH₃)₃ | (1-1-2r) |
| Pr | C(CH₃)₃ | (1-1-3r) |
| CH(CH₃)₂ | C(CH₃)₃ | (1-1-4r) |
| Bu | C(CH₃)₃ | (1-1-5r) |
| C(CH₃)₃ | C(CH₃)₃ | (1-1-6r) |
| (CH₂)₄CH₃ | C(CH₃)₃ | (1-1-7r) |
| (CH₂)₅CH₃ | C(CH₃)₃ | (1-1-8r) |
| (CH₂)₇CH₃ | C(CH₃)₃ | (1-1-9r) |
| (CH₂)₁₁CH₃ | C(CH₃)₃ | (1-1-10r) |

-continued

R—NH—C(=O)—O—R'

| R | R' | |
|---|----|--|
| (CH₂)₁₇CH₃ | C(CH₃)₃ | (1-1-11r) |
| allyl | C(CH₃)₃ | (1-1-12r) |
| cyclopropylmethyl | C(CH₃)₃ | (1-1-13r) |
| cyclopentylmethyl | C(CH₃)₃ | (1-1-14r) |
| cyclohexylmethyl | C(CH₃)₃ | (1-1-15r) |
| adamantylmethyl | C(CH₃)₃ | (1-1-16r) |
| -CH₂Cl (branched) | C(CH₃)₃ | (1-1-17r) |
| -(CH₂)₂Cl (branched) | C(CH₃)₃ | (1-1-18r) |
| -(CH₂)₄Cl (branched) | C(CH₃)₃ | (1-1-19r) |

R—NH—C(=O)—O—R'

| R | R' | |
|---|----|--|
| CH₃ | (CH₂)₇CH₃ | (1-1-1s) |
| Et | (CH₂)₇CH₃ | (1-1-2s) |
| Pr | (CH₂)₇CH₃ | (1-1-3s) |
| CH(CH₃)₂ | (CH₂)₇CH₃ | (1-1-4s) |
| Bu | (CH₂)₇CH₃ | (1-1-5s) |
| C(CH₃)₃ | (CH₂)₇CH₃ | (1-1-6s) |
| (CH₂)₄CH₃ | (CH₂)₇CH₃ | (1-1-7s) |
| (CH₂)₅CH₃ | (CH₂)₇CH₃ | (1-1-8s) |
| (CH₂)₇CH₃ | (CH₂)₇CH₃ | (1-1-9s) |
| (CH₂)₁₁CH₃ | (CH₂)₇CH₃ | (1-1-10s) |
| (CH₂)₁₇CH₃ | (CH₂)₇CH₃ | (1-1-11s) |

-continued

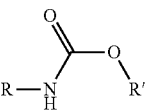

| R | R' | |
|---|---|---|
| 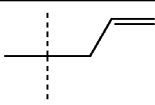 | (CH₂)₇CH₃ | (1-1-12s) |
| 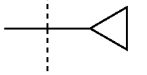 | (CH₂)₇CH₃ | (1-1-13s) |
| 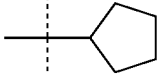 | (CH₂)₇CH₃ | (1-1-14s) |
| 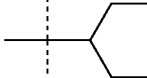 | (CH₂)₇CH₃ | (1-1-15s) |
| 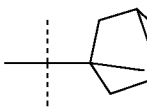 | (CH₂)₇CH₃ | (1-1-16s) |
| 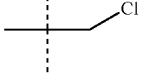 | (CH₂)₇CH₃ | (1-1-17s) |
| 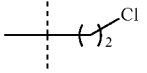 | (CH₂)₇CH₃ | (1-1-18s) |
| 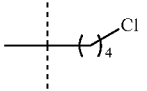 | (CH₂)₇CH₃ | (1-1-19s) |
| CH₃ | Ph | (1-1-1t) |
| Et | Ph | (1-1-2t) |
| Pr | Ph | (1-1-3t) |
| CH(CH₃)₂ | Ph | (1-1-4t) |
| Bu | Ph | (1-1-5t) |
| C(CH₃)₃ | Ph | (1-1-6t) |
| (CH₂)₄CH₃ | Ph | (1-1-7t) |
| (CH₂)₅CH₃ | Ph | (1-1-8t) |
| (CH₂)₇CH₃ | Ph | (1-1-9t) |
| (CH₂)₁₁CH₃ | Ph | (1-1-10t) |
| (CH₂)₁₇CH₃ | Ph | (1-1-11t) |
| 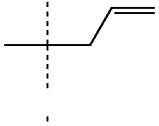 | Ph | (1-1-12t) |
| 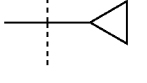 | Ph | (1-1-13t) |
| 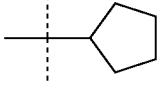 | Ph | (1-1-14t) |

-continued

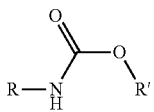

| R | R' | |
|---|---|---|
| 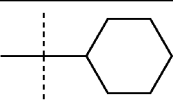 | Pt | (1-1-15t) |
|  | Ph | (1-1-16t) |
| 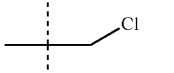 | Ph | (1-1-17t) |
| 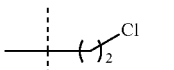 | Ph | (1-1-18t) |
| 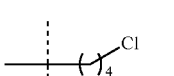 | Ph | (1-1-19t) |

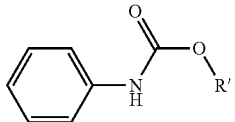

| R | R' | |
|---|---|---|
| H | CH₃ | (1-1-20p) |
| CH₃ | CH₃ | (1-1-21p) |
| (CH₂)₃CH₃ | CH₃ | (1-1-22p) |
| (CH₂)₇CH₃ | CH₃ | (1-1-23p) |
| OCH₃ | CH₃ | (1-1-24p) |
| OCH₂CH₃ | CH₃ | (1-1-25p) |
| CH(CH₃)₂ | CH₃ | (1-1-26p) |
| C(CH₃)₃ | CH₃ | (1-1-27p) |
| N(CH₃)₂ | CH₃ | (1-1-28p) |
| F | CH₃ | (1-1-29p) |
| Cl | CH₃ | (1-1-30p) |
| Br | CH₃ | (1-1-31p) |
| H | CH(CH₃)₂ | (1-1-20q) |
| CH₃ | CH(CH₃)₂ | (1-1-21q) |
| (CH₂)₃CH₃ | CH(CH₃)₂ | (1-1-22q) |
| (CH₂)₇CH₃ | CH(CH₃)₂ | (1-1-23q) |
| OCH₃ | CH(CH₃)₂ | (1-1-24q) |
| OCH₂CH₃ | CH(CH₃)₂ | (1-1-25q) |
| CH(CH₃)₂ | CH(CH₃)₂ | (1-1-26q) |
| C(CH₃)₃ | CH(CH₃)₂ | (1-1-27q) |
| N(CH₃)₂ | CH(CH₃)₂ | (1-1-28q) |
| F | CH(CH₃)₂ | (1-1-29q) |
| Cl | CH(CH₃)₂ | (1-1-30q) |
| Br | CH(CH₃)₂ | (1-1-31q) |
| H | C(CH₃)₃ | (1-1-20r) |
| CH₃ | C(CH₃)₃ | (1-1-21r) |
| (CH₂)₃CH₃ | C(CH₃)₃ | (1-1-22r) |
| (CH₂)₇CH₃ | C(CH₃)₃ | (1-1-23r) |
| OCH₃ | C(CH₃)₃ | (1-1-24r) |
| OCH₂CH₃ | C(CH₃)₃ | (1-1-25r) |

-continued

Structure: ortho-substituted phenyl carbamate (R on ortho position)

| R | R' | |
|---|----|---|
| CH(CH₃)₂ | C(CH₃)₃ | (1-1-26r) |
| C(CH₃)₃ | C(CH₃)₃ | (1-1-27r) |
| N(CH₃)₂ | C(CH₃)₃ | (1-1-28r) |
| F | C(CH₃)₃ | (1-1-29r) |
| Cl | C(CH₃)₃ | (1-1-30r) |
| Br | C(CH₃)₃ | (1-1-31r) |
| H | (CH₂)₇CH₃ | (1-1-20s) |
| CH₃ | (CH₂)₇CH₃ | (1-1-21s) |
| (CH₂)₃CH₃ | (CH₂)₇CH₃ | (1-1-22s) |
| (CH₂)₇CH₃ | (CH₂)₇CH₃ | (1-1-23s) |
| OCH₃ | (CH₂)₇CH₃ | (1-1-24s) |
| OCH₂CH₃ | (CH₂)₇CH₃ | (1-1-25s) |
| CH(CH₃)₂ | (CH₂)₇CH₃ | (1-1-26s) |
| C(CH₃)₃ | (CH₂)₇CH₃ | (1-1-27s) |
| N(CH₃)₂ | (CH₂)₇CH₃ | (1-1-28s) |
| F | (CH₂)₇CH₃ | (1-1-29s) |
| Cl | (CH₂)₇CH₃ | (1-1-30s) |
| Br | (CH₂)₇CH₃ | (1-1-31s) |
| H | Ph | (1-1-20t) |
| CH₃ | Ph | (1-1-21t) |
| (CH₂)₃CH₃ | Ph | (1-1-22t) |
| (CH₂)₇CH₃ | Ph | (1-1-23t) |
| OCH₃ | Ph | (1-1-24t) |
| OCH₂CH₃ | Ph | (1-1-25t) |
| CH(CH₃)₂ | Ph | (1-1-26t) |
| C(CH₃)₃ | Ph | (1-1-27t) |
| N(CH₃)₂ | Ph | (1-1-28t) |
| F | Ph | (1-1-29t) |
| Cl | Ph | (1-1-30t) |
| Br | Ph | (1-1-31t) |

Structure: meta-substituted phenyl carbamate

| R | R' | |
|---|----|---|
| CH₃ | CH₃ | (1-1-32p) |
| (CH₂)₃CH₃ | CH₃ | (1-1-33p) |
| (CH₂)₇CH₃ | CH₃ | (1-1-34p) |
| OCH₃ | CH₃ | (1-1-35p) |
| OCH₂CH₃ | CH₃ | (1-1-36p) |
| CH(CH₃)₂ | CH₃ | (1-1-37p) |
| C(CH₃)₃ | CH₃ | (1-1-38p) |
| N(CH₃)₂ | CH₃ | (1-1-39p) |
| F | CH₃ | (1-1-40p) |
| Cl | CH₃ | (1-1-41p) |
| Br | CH₃ | (1-1-42p) |
| CH₃ | CH(CH₃)₂ | (1-1-32q) |
| (CH₂)₃CH₃ | CH(CH₃)₂ | (1-1-33q) |
| (CH₂)₇CH₃ | CH(CH₃)₂ | (1-1-34q) |
| OCH₃ | CH(CH₃)₂ | (1-1-35q) |
| OCH₂CH₃ | CH(CH₃)₂ | (1-1-36q) |
| CH(CH₃)₂ | CH(CH₃)₂ | (1-1-37q) |
| C(CH₃)₃ | CH(CH₃)₂ | (1-1-38q) |
| N(CH₃)₂ | CH(CH₃)₂ | (1-1-39q) |
| F | CH(CH₃)₂ | (1-1-40q) |
| Cl | CH(CH₃)₂ | (1-1-41q) |
| Br | CH(CH₃)₂ | (1-1-42q) |
| CH₃ | C(CH₃)₃ | (1-1-32r) |

-continued

Structure: meta-substituted phenyl carbamate

| R | R' | |
|---|----|---|
| (CH₂)₃CH₃ | C(CH₃)₃ | (1-1-33r) |
| (CH₂)₇CH₃ | C(CH₃)₃ | (1-1-34r) |
| OCH₃ | C(CH₃)₃ | (1-1-35r) |
| OCH₂CH₃ | C(CH₃)₃ | (1-1-36r) |
| CH(CH₃)₂ | C(CH₃)₃ | (1-1-37r) |
| C(CH₃)₃ | C(CH₃)₃ | (1-1-38r) |
| N(CH₃)₂ | C(CH₃)₃ | (1-1-39r) |
| F | C(CH₃)₃ | (1-1-40r) |
| Cl | C(CH₃)₃ | (1-1-41r) |
| Br | C(CH₃)₃ | (1-1-42r) |
| CH₃ | CH₃ | (1-1-32s) |
| (CH₂)₃CH₃ | (CH₂)₇CH₃ | (1-1-33s) |
| (CH₂)₇CH₃ | (CH₂)₇CH₃ | (1-1-34s) |
| OCH₃ | (CH₂)₇CH₃ | (1-1-35s) |
| OCH₂CH₃ | (CH₂)₇CH₃ | (1-1-36s) |
| CH(CH₃)₂ | (CH₂)₇CH₃ | (1-1-37s) |
| C(CH₃)₃ | (CH₂)₇CH₃ | (1-1-38s) |
| N(CH₃)₂ | (CH₂)₇CH₃ | (1-1-39s) |
| F | (CH₂)₇CH₃ | (1-1-40s) |
| Cl | (CH₂)₇CH₃ | (1-1-41s) |
| Br | (CH₂)₇CH₃ | (1-1-42s) |
| CH₃ | Ph | (1-1-32t) |
| (CH₂)₃CH₃ | Ph | (1-1-33t) |
| (CH₂)₇CH₃ | Ph | (1-1-34t) |
| OCH₃ | Ph | (1-1-35t) |
| OCH₂CH₃ | Ph | (1-1-36t) |
| CH(CH₃)₂ | Ph | (1-1-37t) |
| C(CH₃)₃ | Ph | (1-1-38t) |
| N(CH₃)₂ | Ph | (1-1-39t) |
| F | Ph | (1-1-40t) |
| Cl | Ph | (1-1-41t) |
| Br | Ph | (1-1-42t) |

Structure: para-substituted phenyl carbamate

| R | R' | |
|---|----|---|
| CH₃ | CH₃ | (1-1-43p) |
| (CH₂)₃CH₃ | CH₃ | (1-1-44p) |
| (CH₂)₇CH | CH₃ | (1-1-45p) |
| OCH₃ | CH₃ | (1-1-46p) |
| OCH₂CH₃ | CH₃ | (1-1-47p) |
| CH(CH₃)₂ | CH₃ | (1-1-48p) |
| C(CH₃)₃ | CH₃ | (1-1-49p) |
| N(CH₃)₂ | CH₃ | (1-1-50p) |
| F | CH₃ | (1-1-51p) |
| Cl | CH₃ | (1-1-52p) |
| Br | CH₃ | (1-1-53p) |
| CH₃ | CH(CH₃)₂ | (1-1-43q) |
| (CH₂)₃CH₃ | CH(CH₃)₂ | (1-1-44q) |
| (CH₂)₇CH | CH(CH₃)₂ | (1-1-45q) |
| OCH₃ | CH(CH₃)₂ | (1-1-46q) |
| OCH₂CH₃ | CH(CH₃)₂ | (1-1-47q) |
| CH(CH₃)₂ | CH(CH₃)₂ | (1-1-48q) |
| C(CH₃)₃ | CH(CH₃)₂ | (1-1-49q) |
| N(CH₃)₂ | CH(CH₃)₂ | (1-1-50q) |
| F | CH(CH₃)₂ | (1-1-51q) |
| Cl | CH(CH₃)₂ | (1-1-52q) |
| Br | CH(CH₃)₂ | (1-1-53q) |
| CH₃ | C(CH₃)₃ | (1-1-43r) |

-continued

Structure: R-C6H4-NH-C(=O)-O-R' (para-substituted)

| R | R' | |
|---|---|---|
| (CH2)3CH3 | C(CH3)3 | (1-1-44r) |
| (CH2)7CH | C(CH3)3 | (1-1-45r) |
| OCH3 | C(CH3)3 | (1-1-46r) |
| OCH2CH3 | C(CH3)3 | (1-1-47r) |
| CH(CH3)2 | C(CH3)3 | (1-1-48r) |
| C(CH3)3 | C(CH3)3 | (1-1-49r) |
| N(CH3)2 | C(CH3)3 | (1-1-50r) |
| F | C(CH3)3 | (1-1-51r) |
| Cl | C(CH3)3 | (1-1-52r) |
| Br | C(CH3)3 | (1-1-53r) |
| CH3 | (CH2)7CH3 | (1-1-43s) |
| (CH2)3CH3 | (CH2)7CH3 | (1-1-44s) |
| (CH2)7CH | (CH2)7CH3 | (1-1-45s) |
| OCH3 | (CH2)7CH3 | (1-1-46s) |
| OCH2CH3 | (CH2)7CH3 | (1-1-47s) |
| CH(CH3)2 | (CH2)7CH3 | (1-1-48s) |
| C(CH3)3 | (CH2)7CH3 | (1-1-49s) |
| N(CH3)2 | (CH2)7CH3 | (1-1-50s) |
| F | (CH2)7CH3 | (1-1-51s) |
| Cl | (CH2)7CH3 | (1-1-52s) |
| Br | (CH2)7CH3 | (1-1-53s) |
| CH3 | PH | (1-1-43t) |
| (CH2)3CH3 | PH | (1-1-44t) |
| (CH2)7CH | PH | (1-1-45t) |
| OCH3 | PH | (1-1-46t) |
| OCH2CH3 | PH | (1-1-47t) |
| CH(CH3)2 | PH | (1-1-48t) |
| C(CH3)3 | PH | (1-1-49t) |
| N(CH3)2 | PH | (1-1-50t) |
| F | PH | (1-1-51t) |
| Cl | PH | (1-1-52t) |
| Br | PH | (1-1-53t) |

Structure: 2,6-di-R-C6H3-NH-C(=O)-O-R'

| R | R' | |
|---|---|---|
| CH3 | CH3 | (1-1-54p) |
| (CH2)3CH3 | CH3 | (1-1-55p) |
| (CH2)7CH3 | CH3 | (1-1-56p) |
| OCH3 | CH3 | (1-1-57p) |
| OCH2CH3 | CH3 | (1-1-58p) |
| CH(CH3)2 | CH3 | (1-1-59p) |
| C(CH3)3 | CH3 | (1-1-60p) |
| N(CH3)2 | CH3 | (1-1-61p) |
| F | CH3 | (1-1-62p) |
| Cl | CH3 | (1-1-63p) |
| Br | CH3 | (1-1-64p) |
| CH3 | CH(CH3)2 | (1-1-54q) |
| (CH2)3CH3 | CH(CH3)2 | (1-1-55q) |
| (CH2)7CH3 | CH(CH3)2 | (1-1-56q) |
| OCH3 | CH(CH3)2 | (1-1-57q) |
| OCH2CH3 | CH(CH3)2 | (1-1-58q) |
| CH(CH3)2 | CH(CH3)2 | (1-1-59q) |
| C(CH3)3 | CH(CH3)2 | (1-1-60q) |
| N(CH3)2 | CH(CH3)2 | (1-1-61q) |
| F | CH(CH3)2 | (1-1-62q) |
| Cl | CH(CH3)2 | (1-1-63q) |
| Br | CH(CH3)2 | (1-1-64q) |
| CH3 | C(CH3)3 | (1-1-54r) |

-continued

Structure: 2,6-di-R-C6H3-NH-C(=O)-O-R'

| R | R' | |
|---|---|---|
| (CH2)3CH3 | C(CH3)3 | (1-1-55r) |
| (CH2)7CH3 | C(CH3)3 | (1-1-56r) |
| OCH3 | C(CH3)3 | (1-1-57r) |
| OCH2CH3 | C(CH3)3 | (1-1-58r) |
| CH(CH3)2 | C(CH3)3 | (1-1-59r) |
| C(CH3)3 | C(CH3)3 | (1-1-60r) |
| N(CH3)2 | C(CH3)3 | (1-1-61r) |
| F | C(CH3)3 | (1-1-62r) |
| Cl | C(CH3)3 | (1-1-63r) |
| Br | C(CH3)3 | (1-1-64r) |
| CH3 | (CH2)7CH3 | (1-1-54s) |
| (CH2)3CH3 | (CH2)7CH3 | (1-1-55s) |
| (CH2)7CH3 | (CH2)7CH3 | (1-1-56s) |
| OCH3 | (CH2)7CH3 | (1-1-57s) |
| OCH2CH3 | (CH2)7CH3 | (1-1-58s) |
| CH(CH3)2 | (CH2)7CH3 | (1-1-59s) |
| C(CH3)3 | (CH2)7CH3 | (1-1-60s) |
| N(CH3)2 | (CH2)7CH3 | (1-1-61s) |
| F | (CH2)7CH3 | (1-1-62s) |
| Cl | (CH2)7CH3 | (1-1-63s) |
| Br | (CH2)7CH3 | (1-1-64s) |
| CH3 | Ph | (1-1-54t) |
| (CH2)3CH3 | Ph | (1-1-55t) |
| (CH2)7CH3 | Ph | (1-1-56t) |
| OCH3 | Ph | (1-1-57t) |
| OCH2CH3 | Ph | (1-1-58t) |
| CH(CH3)2 | Ph | (1-1-59t) |
| C(CH3)3 | Ph | (1-1-60t) |
| N(CH3)2 | Ph | (1-1-61t) |
| F | Ph | (1-1-62t) |
| Cl | Ph | (1-1-63t) |
| Br | Ph | (1-1-64t) |

Structure: 3,4-di-R-C6H3-NH-C(=O)-O-R'

| R | R' | |
|---|---|---|
| CH3 | CH3 | (1-1-65p) |
| (CH2)3CH3 | CH3 | (1-1-66p) |
| (CH2)7CH3 | CH3 | (1-1-67p) |
| OCH3 | CH3 | (1-1-68p) |
| OCH2CH3 | CH3 | (1-1-69p) |
| CH(CH3)2 | CH3 | (1-1-70p) |
| C(CH3)3 | CH3 | (1-1-71p) |
| N(CH3)2 | CH3 | (1-1-72p) |
| F | CH3 | (1-1-73p) |
| Cl | CH3 | (1-1-74p) |
| Br | CH3 | (1-1-75p) |
| CH3 | CH(CH3)2 | (1-1-65q) |
| (CH2)3CH3 | CH(CH3)2 | (1-1-66q) |
| (CH2)7CH3 | CH(CH3)2 | (1-1-67q) |
| OCH3 | CH(CH3)2 | (1-1-68q) |
| OCH2CH3 | CH(CH3)2 | (1-1-69q) |
| CH(CH3)2 | CH(CH3)2 | (1-1-70q) |
| C(CH3)3 | CH(CH3)2 | (1-1-71q) |
| N(CH3)2 | CH(CH3)2 | (1-1-72q) |
| F | CH(CH3)2 | (1-1-73q) |
| Cl | CH(CH3)2 | (1-1-74q) |
| Br | CH(CH3)2 | (1-1-75q) |

-continued

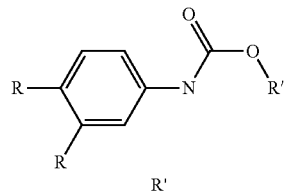

| R | R' | |
|---|----|---|
| CH₃ | C(CH₃)₃ | (1-1-65r) |
| (CH₂)₃CH₃ | C(CH₃)₃ | (1-1-66r) |
| (CH₂)₇CH₃ | C(CH₃)₃ | (1-1-67r) |
| OCH₃ | C(CH₃)₃ | (1-1-68r) |
| OCH₂CH₃ | C(CH₃)₃ | (1-1-69r) |
| CH(CH₃)₂ | C(CH₃)₃ | (1-1-70r) |
| C(CH₃)₃ | C(CH₃)₃ | (1-1-71r) |
| N(CH₃)₂ | C(CH₃)₃ | (1-1-72r) |
| F | C(CH₃)₃ | (1-1-73r) |
| Cl | C(CH₃)₃ | (1-1-74r) |
| Br | C(CH₃)₃ | (1-1-75r) |
| CH₃ | (CH₂)₇CH₃ | (1-1-65s) |
| (CH₂)₃CH₃ | (CH₂)₇CH₃ | (1-1-66s) |
| (CH₂)₇CH₃ | (CH₂)₇CH₃ | (1-1-67s) |
| OCH₃ | (CH₂)₇CH₃ | (1-1-68s) |
| OCH₂CH₃ | (CH₂)₇CH₃ | (1-1-69s) |
| CH(CH₃)₂ | (CH₂)₇CH₃ | (1-1-70s) |
| C(CH₃)₃ | (CH₂)₇CH₃ | (1-1-71s) |
| N(CH₃)₂ | (CH₂)₇CH₃ | (1-1-72s) |
| F | (CH₂)₇CH₃ | (1-1-73s) |
| Cl | (CH₂)₇CH₃ | (1-1-74s) |
| Br | (CH₂)₇CH₃ | (1-1-75s) |
| CH₃ | Ph | (1-1-65t) |
| (CH₂)₃CH₃ | Ph | (1-1-66t) |
| (CH₂)₇CH₃ | Ph | (1-1-67t) |
| OCH₃ | Ph | (1-1-68t) |
| OCH₂CH₃ | Ph | (1-1-69t) |
| CH(CH₃)₂ | Ph | (1-1-70t) |
| C(CH₃)₃ | Ph | (1-1-71t) |
| N(CH₃)₂ | Ph | (1-1-72t) |
| F | Ph | (1-1-73t) |
| Cl | Ph | (1-1-74t) |
| Br | Ph | (1-1-75t) |

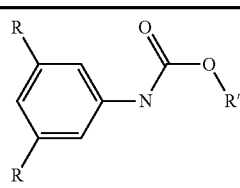

| R | R' | |
|---|----|---|
| CH₃ | CH₃ | (1-1-76p) |
| (CH₂)₃CH₃ | CH₃ | (1-1-77p) |
| (CH₂)₇CH₃ | CH₃ | (1-1-78p) |
| OCH₃ | CH₃ | (1-1-79p) |
| OCH₂CH₃ | CH₃ | (1-1-80p) |
| CH(CH₃)₂ | CH₃ | (1-1-81p) |
| C(CH₃)₃ | CH₃ | (1-1-82p) |
| N(CH₃)₂ | CH₃ | (1-1-83p) |
| F | CH₃ | (1-1-84p) |
| Cl | CH₃ | (1-1-85p) |
| Br | CH₃ | (1-1-86p) |
| CH₃ | CH(CH₃)₂ | (1-1-76q) |
| (CH₂)₃CH₃ | CH(CH₃)₂ | (1-1-77q) |
| (CH₂)₇CH₃ | CH(CH₃)₂ | (1-1-78q) |
| OCH₃ | CH(CH₃)₂ | (1-1-79q) |
| OCH₂CH₃ | CH(CH₃)₂ | (1-1-80q) |
| CH(CH₃)₂ | CH(CH₃)₂ | (1-1-81q) |
| C(CH₃)₃ | CH(CH₃)₂ | (1-1-82q) |
| N(CH₃)₂ | CH(CH₃)₂ | (1-1-83q) |
| F | CH(CH₃)₂ | (1-1-84q) |
| Cl | CH(CH₃)₂ | (1-1-85q) |

-continued

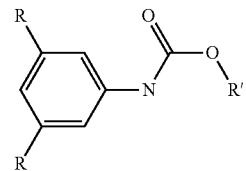

| R | R' | |
|---|----|---|
| Br | CH(CH₃)₂ | (1-1-86q) |
| CH₃ | C(CH₃)₃ | (1-1-76r) |
| (CH₂)₃CH₃ | C(CH₃)₃ | (1-1-77r) |
| (CH₂)₇CH₃ | C(CH₃)₃ | (1-1-78r) |
| OCH₃ | C(CH₃)₃ | (1-1-79r) |
| OCH₂CH₃ | C(CH₃)₃ | (1-1-80r) |
| CH(CH₃)₂ | C(CH₃)₃ | (1-1-81r) |
| C(CH₃)₃ | C(CH₃)₃ | (1-1-82r) |
| N(CH₃)₂ | C(CH₃)₃ | (1-1-83r) |
| F | C(CH₃)₃ | (1-1-84r) |
| Cl | C(CH₃)₃ | (1-1-85r) |
| Br | C(CH₃)₃ | (1-1-86r) |
| CH₃ | (CH₂)₇CH₃ | (1-1-76s) |
| (CH₂)₃CH₃ | (CH₂)₇CH₃ | (1-1-77s) |
| (CH₂)₇CH₃ | (CH₂)₇CH₃ | (1-1-78s) |
| OCH₃ | (CH₂)₇CH₃ | (1-1-79s) |
| OCH₂CH₃ | (CH₂)₇CH₃ | (1-1-80s) |
| CH(CH₃)₂ | (CH₂)₇CH₃ | (1-1-81s) |
| C(CH₃)₃ | (CH₂)₇CH₃ | (1-1-82s) |
| N(CH₃)₂ | (CH₂)₇CH₃ | (1-1-83s) |
| F | (CH₂)₇CH₃ | (1-1-84s) |
| Cl | (CH₂)₇CH₃ | (1-1-85s) |
| Br | (CH₂)₇CH₃ | (1-1-86s) |
| CH₃ | Ph | (1-1-76t) |
| (CH₂)₃CH₃ | Ph | (1-1-77t) |
| (CH₂)₇CH₃ | Ph | (1-1-78t) |
| OCH₃ | Ph | (1-1-79t) |
| OCH₂CH₃ | Ph | (1-1-80t) |
| CH(CH₃)₂ | Ph | (1-1-81t) |
| C(CH₃)₃ | Ph | (1-1-82t) |
| N(CH₃)₂ | Ph | (1-1-83t) |
| F | Ph | (1-1-84t) |
| Cl | Ph | (1-1-85t) |
| Br | Ph | (1-1-86t) |

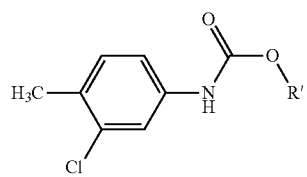

| R' = CH₃ | (1-1-87p) |
|---|---|
| CH(CH₃)₂ | (1-1-87q) |
| C(CH₃)₃ | (1-1-87r) |
| (CH₂)₇CH₃ | (1-1-87s) |
| Ph | (1-1-87t) |

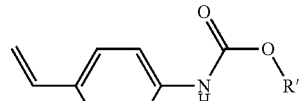

| R' = CH₃ | (1-1-88p) |
|---|---|
| CH(CH₃)₂ | (1-1-88q) |
| C(CH₃)₃ | (1-1-88r) |
| (CH₂)₇CH₃ | (1-1-88s) |
| Ph | (1-1-88t) |

-continued

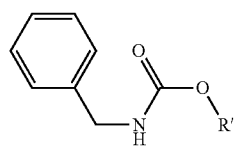

| R′ = | CH₃ | (1-1-89p) |
| --- | --- | --- |
| | CH(CH₃)₂ | (1-1-89q) |
| | C(CH₃)₃ | (1-1-89r) |
| | (CH₂)₇CH₃ | (1-1-89s) |
| | Ph | (1-1-89t) |

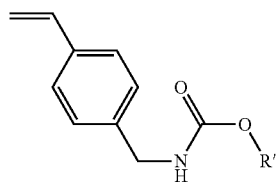

| R′ = | CH₃ | (1-1-90p) |
| --- | --- | --- |
| | CH(CH₃)₂ | (1-1-90q) |
| | C(CH₃)₃ | (1-1-90r) |
| | (CH₂)₇CH₃ | (1-1-90s) |
| | Ph | (1-1-90t) |

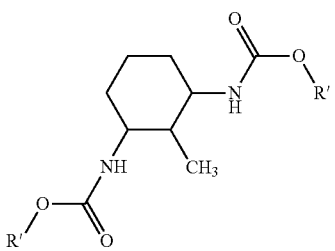

| R | R′ | |
| --- | --- | --- |
| —CH₂— | CH₃ | (1-2-1p) |
| —CH₂CH₂— | CH₃ | (1-2-2p) |
| —CH₂(CH₂)₂CH₂— | CH₃ | (1-2-3p) |
| —CH₂(CH₂)₄CH₂— | CH₃ | (1-2-4p) |
| —CH₂(CH₂)₆CH₂— | CH₃ | (1-2-5p) |
| —CH₂(CH₂)₈CH₂— | CH₃ | (1-2-6p) |
| —CH₂(CH₂)₁₀CH₂— | CH₃ | (1-2-7p) |
| —CH₂— | (CH₃)₂CH | (1-2-1q) |
| —CH₂CH₂— | (CH₃)₂CH | (1-2-2q) |
| —CH₂(CH₂)₂CH₂— | (CH₃)₂CH | (1-2-3q) |
| —CH₂(CH₂)₄CH₂— | (CH₃)₂CH | (1-2-4q) |
| —CH₂(CH₂)₆CH₂— | (CH₃)₂CH | (1-2-5q) |
| —CH₂(CH₂)₈CH₂— | (CH₃)₂CH | (1-2-6q) |
| —CH₂(CH₂)₁₀CH₂— | (CH₃)₂CH | (1-2-7q) |
| —CH₂— | (CH₃)₃C | (1-2-1r) |
| —CH₂CH₂— | (CH₃)₃C | (1-2-2r) |
| —CH₂(CH₂)₂CH₂— | (CH₃)₃C | (1-2-3r) |
| —CH₂(CH₂)₄CH₂— | (CH₃)₃C | (1-2-4r) |
| —CH₂(CH₂)₆CH₂— | (CH₃)₃C | (1-2-5r) |
| —CH₂(CH₂)₈CH₂— | (CH₃)₃C | (1-2-6r) |
| —CH₂(CH₂)₁₀CH₂— | (CH₃)₃C | (1-2-7r) |
| —CH₂— | CH₃(CH₃)₇ | (1-2-1s) |
| —CH₂CH₂— | CH₃(CH₃)₇ | (1-2-2s) |
| —CH₂(CH₂)₂CH₂— | CH₃(CH₃)₇ | (1-2-3s) |
| —CH₂(CH₂)₄CH₂— | CH₃(CH₃)₇ | (1-2-4s) |
| —CH₂(CH₂)₆CH₂— | CH₃(CH₃)₇ | (1-2-5s) |
| —CH₂(CH₂)₈CH₂— | CH₃(CH₃)₇ | (1-2-6s) |
| —CH₂(CH₂)₁₀CH₂— | CH₃(CH₃)₇ | (1-2-7s) |
| —CH₂— | Ph | (1-2-1t) |
| —CH₂CH₂— | Ph | (1-2-2t) |
| —CH₂(CH₂)₂CH₂— | Ph | (1-2-3t) |
| —CH₂(CH₂)₄CH₂— | Ph | (1-2-4t) |
| —CH₂(CH₂)₆CH₂— | Ph | (1-2-5t) |
| —CH₂(CH₂)₈CH₂— | Ph | (1-2-6t) |
| —CH₂(CH₂)₁₀CH₂— | Ph | (1-2-7t) |

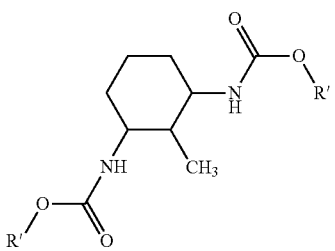

| R′ = | CH₃ | (1-2-8p) |
| --- | --- | --- |
| | (CH₃)₂CH | (1-2-8q) |
| | (CH₃)₃C | (1-2-8r) |
| | CH₃(CH₂)₇ | (1-2-8s) |
| | Ph | (1-2-8t) |

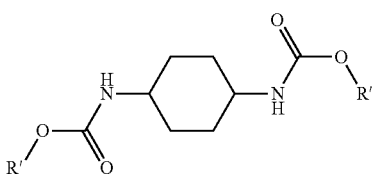

| R′ = | CH₃ | (1-2-9p) |
| --- | --- | --- |
| | (CH₃)₂CH | (1-2-9q) |
| | (CH₃)₃C | (1-2-9r) |
| | CH₃(CH₂)₇ | (1-2-9s) |
| | Ph | (1-2-9t) |

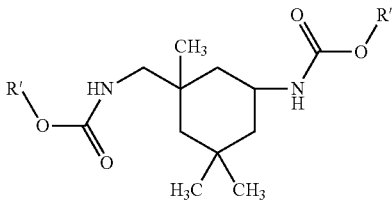

| R′ = | CH₃ | (1-2-10p) |
| --- | --- | --- |
| | (CH₃)₂CH | (1-2-10q) |
| | (CH₃)₃C | (1-2-10r) |
| | CH₃(CH₂)₇ | (1-2-10s) |
| | Ph | (1-2-10t) |

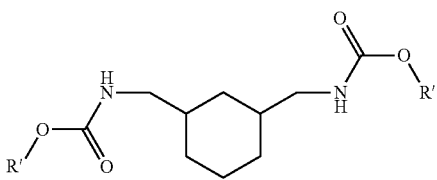

| R′ = | CH₃ | (1-2-11p) |
| --- | --- | --- |
| | (CH₃)₂CH | (1-2-11q) |
| | (CH₃)₃C | (1-2-11r) |
| | CH₃(CH₂)₇ | (1-2-11s) |
| | Ph | (1-2-11t) |

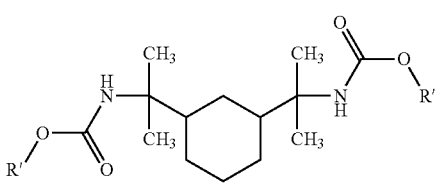

| R′ = | CH₃ | (1-2-12p) |
| --- | --- | --- |
| | (CH₃)₂CH | (1-2-12q) |
| | (CH₃)₃C | (1-2-12r) |
| | CH₃(CH₂)₇ | (1-2-12s) |
| | Ph | (1-2-12t) |

-continued

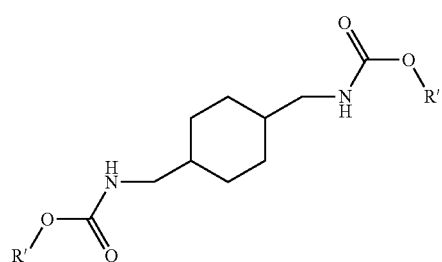

R' = CH₃ (1-2-13p)
(CH₃)₂CH (1-2-13q)
(CH₃)₃C (1-2-13r)
CH₃(CH₂)₇ (1-2-13s)
Ph (1-2-13t)

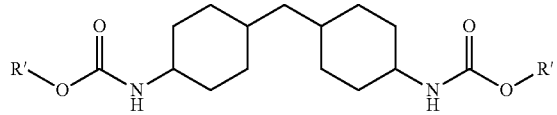

R' = CH₃ (1-2-14p)
(CH₃)₂CH (1-2-14q)
(CH₃)₃C (1-2-14r)
CH₃(CH₂)₇ (1-2-14s)
Ph (1-2-14t)

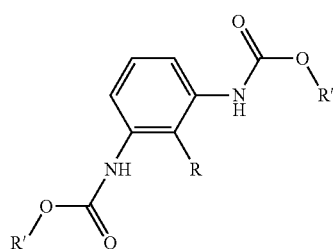

| R | R' | |
|---|---|---|
| H | CH₃ | (1-2-15p) |
| H | CH(CH₃)₂ | (1-2-15q) |
| H | C(CH₃)₃ | (1-2-15r) |
| H | (CH₂)₇CH₃ | (1-2-15s) |
| H | Ph | (1-2-15t) |
| CH₃ | CH₃ | (1-2-16p) |
| CH₃ | CH(CH₃)₂ | (1-2-16q) |
| CH₃ | C(CH₃)₃ | (1-2-16r) |
| CH₃ | (CH₂)₇CH₃ | (1-2-16s) |
| CH₃ | Ph | (1-2-16t) |

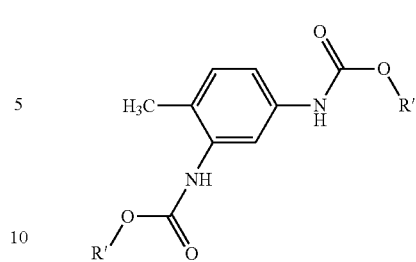

R' = CH₃ (1-2-17p)
(CH₃)₂CH (1-2-17q)
(CH₃)₃C (1-2-17r)
CH₃(CH₂)₇ (1-2-17s)
Ph (1-2-17t)

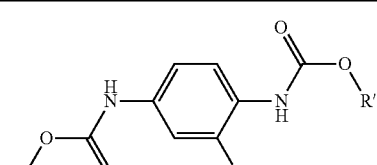

| R | R' | |
|---|---|---|
| H | CH₃ | (1-2-18p) |
| H | CH(CH₃)₂ | (1-2-18q) |
| H | C(CH₃)₃ | (1-2-18r) |
| H | (CH₂)₇CH₃ | (1-2-18s) |
| H | Ph | (1-2-18t) |
| CH₃ | CH₃ | (1-2-19p) |
| CH₃ | CH(CH₃)₂ | (1-2-19q) |
| CH₃ | C(CH₃)₃ | (1-2-19r) |
| CH₃ | (CH₂)₇CH₃ | (1-2-19s) |
| CH₃ | Ph | (1-2-19t) |

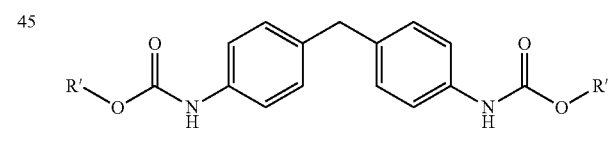

R' = CH₃ (1-2-20 p)
(CH₃)₂CH (1-2-20 q)
(CH₃)₃C (1-2-20 r)
CH₃(CH₂)₇ (1-2-20 s)
Ph (1-2-20 t)

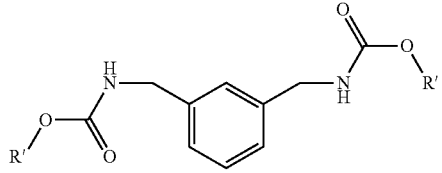

R' = CH₃ (1-2-21 p)
(CH₃)₂CH (1-2-21 q)
(CH₃)₃C (1-2-21 r)
CH₃(CH₂)₇ (1-2-21 s)
Ph (1-2-21 t)

-continued

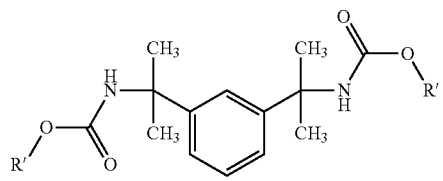

R' = CH₃ (1-2-22 p)
(CH₃)₂CH (1-2-22 q)
(CH₃)₃C (1-2-22 r)
CH₃(CH₂)₇ (1-2-22 s)
Ph (1-2-22 t)

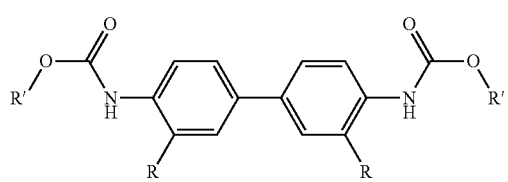

| R | R' | |
|---|---|---|
| CH₃ | CH₃ | (1-2-23p) |
| CH₃ | CH(CH₃)₂ | (1-2-23q) |
| CH₃ | C(CH₃)₃ | (1-2-23r) |
| CH₃ | (CH₂)₇CH₃ | (1-2-23s) |
| CH₃ | Ph | (1-2-23t) |
| CH₂CH₃ | CH₃ | (1-2-24p) |
| CH₂CH₃ | CH(CH₃)₂ | (1-2-24q) |
| CH₂CH₃ | C(CH₃)₃ | (1-2-24r) |
| CH₂CH₃ | (CH₂)₇CH₃ | (1-2-24s) |
| CH₂CH₃ | Ph | (1-2-24t) |
| OCH₃ | CH₃ | (1-2-25p) |
| OCH₃ | CH(CH₃)₂ | (1-2-25q) |
| OCH₃ | C(CH₃)₃ | (1-2-25r) |
| OCH₃ | (CH₂)₇CH₃ | (1-2-25s) |
| OCH₃ | Ph | (1-2-25t) |

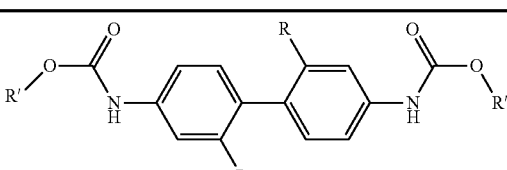

| R | R' | |
|---|---|---|
| CH₃ | CH₃ | (1-2-26p) |
| CH₃ | CH(CH₃)₂ | (1-2-26q) |
| CH₃ | C(CH₃)₃ | (1-2-26r) |
| CH₃ | (CH₂)₇CH₃ | (1-2-26s) |
| CH₃ | Ph | (1-2-26t) |
| CF₃ | CH₃ | (1-2-27p) |
| CF₃ | CH(CH₃)₂ | (1-2-27q) |
| CF₃ | C(CH₃)₃ | (1-2-27r) |
| CF₃ | (CH₂)₇CH₃ | (1-2-27s) |
| CF₃ | Ph | (1-2-27t) |

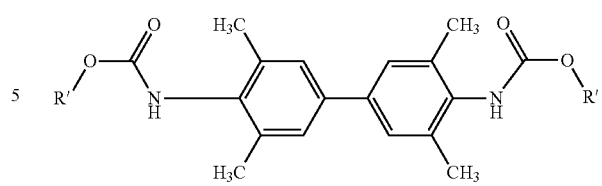

R' = CH₃ (1-2-28p)
(CH₃)₂CH (1-2-28q)
(CH₃)₃C (1-2-28r)
CH₃(CH₂)₇ (1-2-28s)
Ph (1-2-28t)

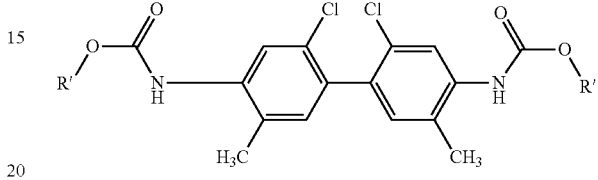

R' = CH₃ (1-2-29p)
(CH₃)₂CH (1-2-29q)
(CH₃)₃C (1-2-29r)
CH₃(CH₂)₇ (1-2-29s)
Ph (1-2-29t)

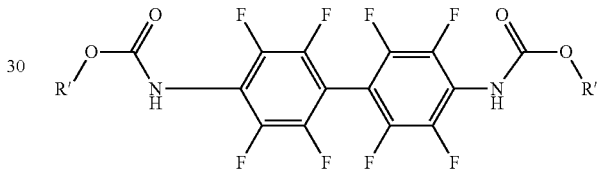

R' = CH₃ (1-2-30p)
(CH₃)₂CH (1-2-30q)
(CH₃)₃C (1-2-30r)
CH₃(CH₂)₇ (1-2-30s)
Ph (1-2-30t)

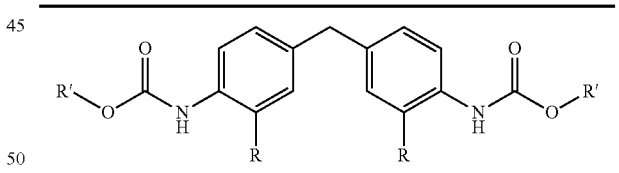

| R | R' | |
|---|---|---|
| CH₃ | CH₃ | (1-2-31p) |
| CH₃ | CH(CH₃)₂ | (1-2-31q) |
| CH₃ | C(CH₃)₃ | (1-2-31r) |
| CH₃ | (CH₃)₇CH₃ | (1-2-31s) |
| CH₃ | Ph | (1-2-31t) |
| Cl | CH₃ | (1-2-32p) |
| Cl | CH(CH₃)₂ | (1-2-32q) |
| Cl | C(CH₃)₃ | (1-2-32r) |
| Cl | (CH₃)₇CH₃ | (1-2-32s) |
| Cl | Ph | (1-2-32t) |

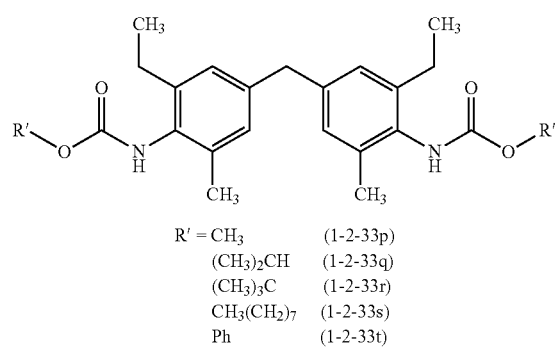

R' = CH₃ (1-2-33p)
(CH₃)₂CH (1-2-33q)
(CH₃)₃C (1-2-33r)
CH₃(CH₂)₇ (1-2-33s)
Ph (1-2-33t)

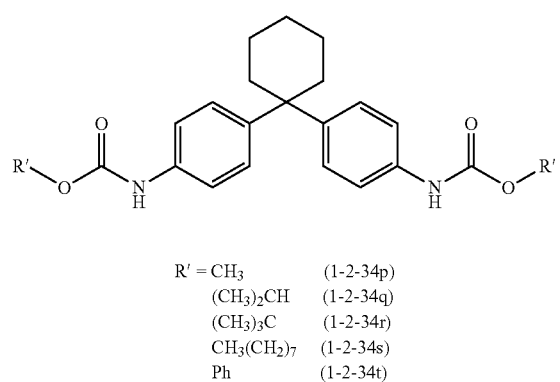

R' = CH₃ (1-2-34p)
(CH₃)₂CH (1-2-34q)
(CH₃)₃C (1-2-34r)
CH₃(CH₂)₇ (1-2-34s)
Ph (1-2-34t)

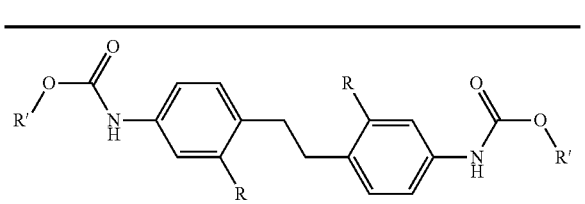

| R | R' | |
|---|---|---|
| H | CH₃ | (1-2-35p) |
| H | CH(CH₃)₂ | (1-2-35q) |
| H | C(CH₃)₃ | (1-2-35r) |
| H | (CH₂)₇CH₃ | (1-2-35s) |
| H | Ph | (1-2-35t) |
| CH₃ | CH₃ | (1-2-36p) |
| CH₃ | CH(CH₃)₂ | (1-2-36q) |
| CH₃ | C(CH₃)₃ | (1-2-36r) |
| CH₃ | (CH₂)₇CH₃ | (1-2-36s) |
| CH₃ | Ph | (1-2-36t) |

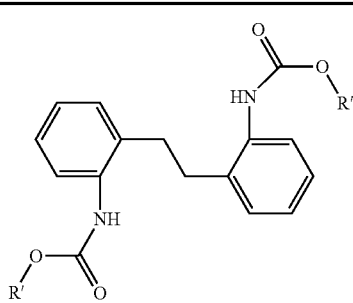

R' = CH₃ (1-2-37p)
(CH₃)₂CH (1-2-37q)
(CH₃)₃C (1-2-37r)
CH₃(CH₂)₇ (1-2-37s)
Ph (1-2-37t)

-continued

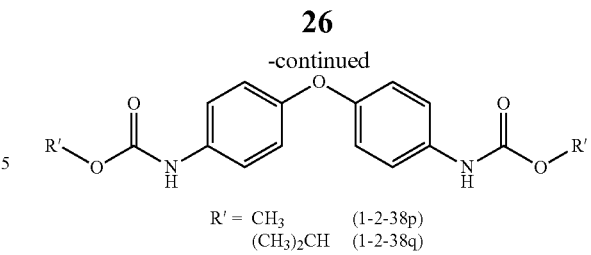

R' = CH₃ (1-2-38p)
(CH₃)₂CH (1-2-38q)
(CH₃)₃C (1-2-38r)
CH₃(CH₂)₇ (1-2-38s)
Ph (1-2-38t)

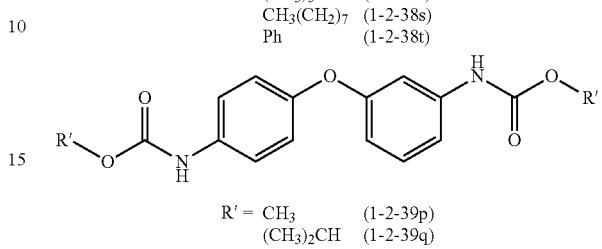

R' = CH₃ (1-2-39p)
(CH₃)₂CH (1-2-39q)
(CH₃)₃C (1-2-39r)
CH₃(CH₂)₇ (1-2-39s)
Ph (1-2-39t)

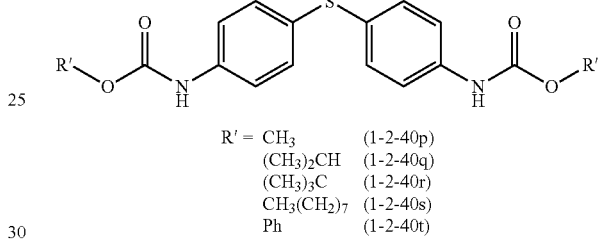

R' = CH₃ (1-2-40p)
(CH₃)₂CH (1-2-40q)
(CH₃)₃C (1-2-40r)
CH₃(CH₂)₇ (1-2-40s)
Ph (1-2-40t)

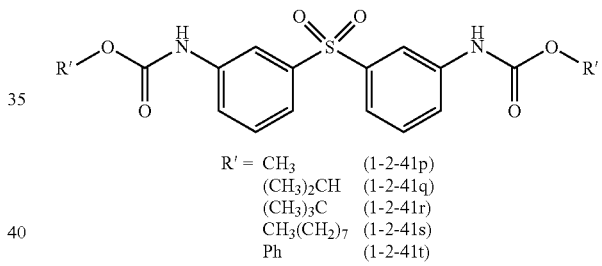

R' = CH₃ (1-2-41p)
(CH₃)₂CH (1-2-41q)
(CH₃)₃C (1-2-41r)
CH₃(CH₂)₇ (1-2-41s)
Ph (1-2-41t)

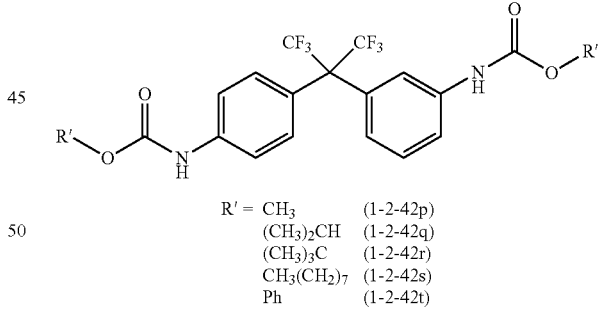

R' = CH₃ (1-2-42p)
(CH₃)₂CH (1-2-42q)
(CH₃)₃C (1-2-42r)
CH₃(CH₂)₇ (1-2-42s)
Ph (1-2-42t)

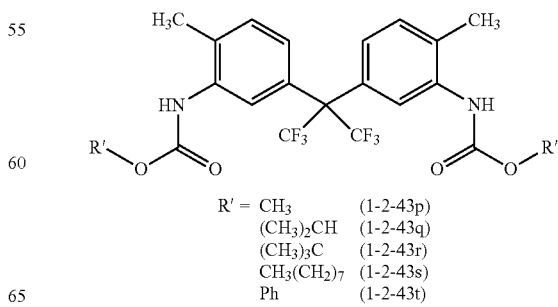

R' = CH₃ (1-2-43p)
(CH₃)₂CH (1-2-43q)
(CH₃)₃C (1-2-43r)
CH₃(CH₂)₇ (1-2-43s)
Ph (1-2-43t)

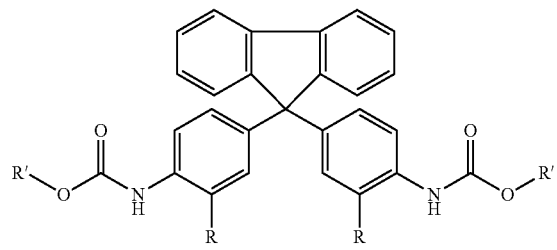
| R | R' | |
|---|---|---|
| H | CH₃ | (1-2-44p) |
| H | CH(CH₃)₂ | (1-2-44q) |
| H | C(CH₃)₃ | (1-2-44r) |
| H | (CH₂)₇CH₃ | (1-2-44s) |
| H | Ph | (1-2-44t) |
| CH₃ | CH₃ | (1-2-45p) |
| CH₃ | CH(CH₃)₂ | (1-2-45q) |
| CH₃ | C(CH₃)₃ | (1-2-45r) |
| CH₃ | (CH₂)₇CH₃ | (1-2-45s) |
| CH₃ | Ph | (1-2-45t) |
| F | CH₃ | (1-2-46p) |
-continued
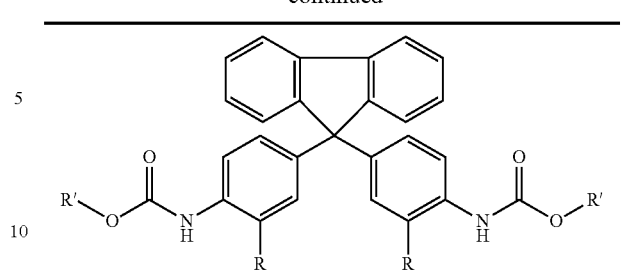
| R | R' | |
|---|---|---|
| F | CH(CH₃)₂ | (1-2-46q) |
| F | C(CH₃)₃ | (1-2-46r) |
| F | (CH₂)₇CH₃ | (1-2-46s) |
| F | Ph | (1-2-46t) |
| Cl | CH₃ | (1-2-47p) |
| Cl | CH(CH₃)₂ | (1-2-47q) |
| Cl | C(CH₃)₃ | (1-2-47r) |
| Cl | (CH₂)₇CH₃ | (1-2-47s) |
| Cl | Ph | (1-2-47t) |
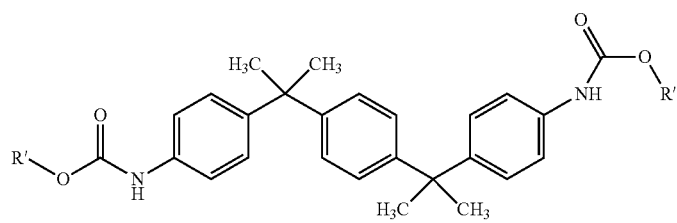
R' = CH₃ (1-2-48p)
(CH₃)₂CH (1-2-48q)
(CH₃)₃C (1-2-48r)
CH₃(CH₂)₇ (1-2-48s)
Ph (1-2-48t)
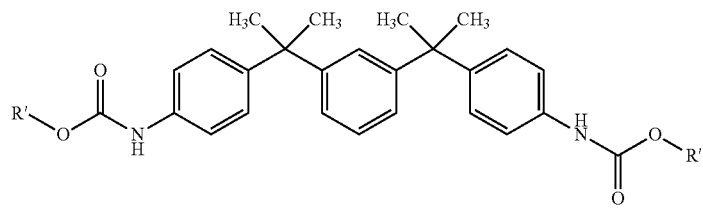
R' = CH₃ (1-2-49p)
(CH₃)₂CH (1-2-49q)
(CH₃)₃C (1-2-49r)
CH₃(CH₂)₇ (1-2-49s)
Ph (1-2-49t)
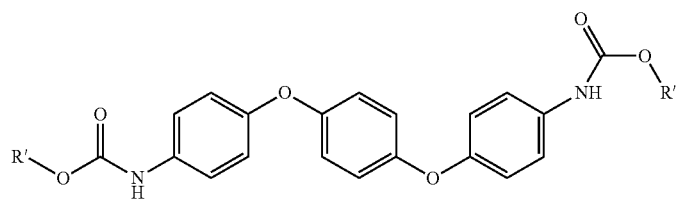
R' = CH₃ (1-2-50p)
(CH₃)₂CH (1-2-50q)
(CH₃)₃C (1-2-50r)
CH₃(CH₂)₇ (1-2-50s)
Ph (1-2-50t)

-continued
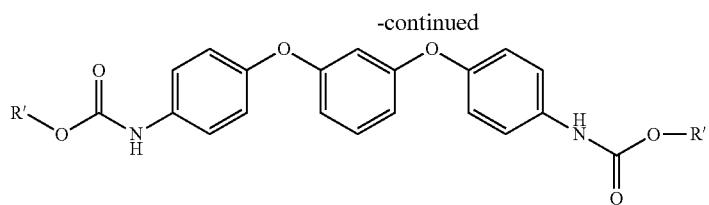
R' = CH₃ (1-2-51p)
(CH₃)₂CH (1-2-51q)
(CH₃)₃C (1-2-51r)
CH₃(CH₂)₇ (1-2-51s)
Ph (1-2-51t)
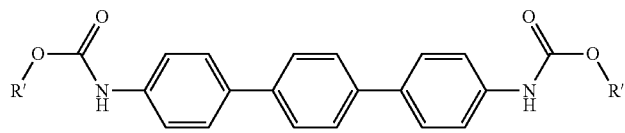
R' = CH₃ (1-2-52p)
(CH₃)₂CH (1-2-52q)
(CH₃)₃C (1-2-52r)
CH₃(CH₂)₇ (1-2-52s)
Ph (1-2-52t)
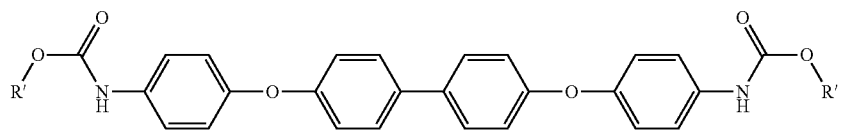
R' = CH₃ (1-2-53p)
(CH₃)₂CH (1-2-53q)
(CH₃)₃C (1-2-53r)
CH₃(CH₂)₇ (1-2-53s)
Ph (1-2-53t)
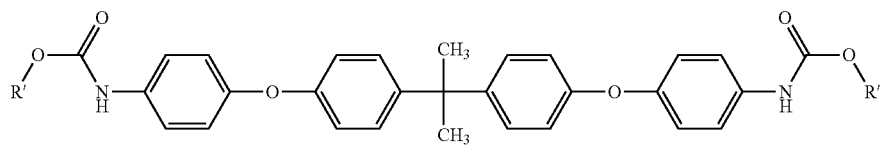
R' = CH₃ (1-2-54p)
(CH₃)₂CH (1-2-54q)
(CH₃)₃C (1-2-54r)
CH₃(CH₂)₇ (1-2-54s)
Ph (1-2-54t)
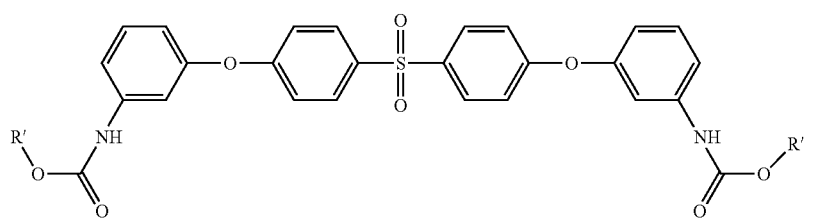
R' = CH₃ (1-2-55p)
(CH₃)₂CH (1-2-55q)
(CH₃)₃C (1-2-55r)
CH₃(CH₂)₇ (1-2-55s)
Ph (1-2-55t)

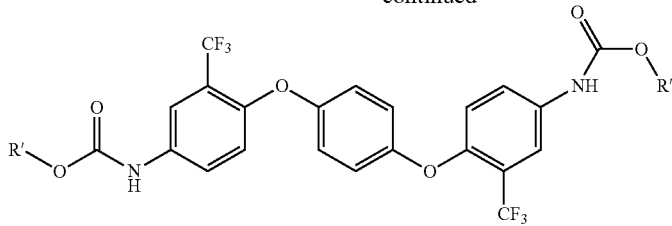

R′ = CH₃ (1-2-56p)
(CH₃)₂CH (1-2-56q)
(CH₃)₃C (1-2-56r)
CH₃(CH₂)₇ (1-2-56s)
Ph (1-2-56t)

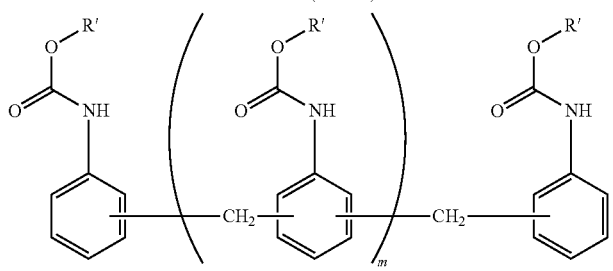

R′ = CH₃ (1-3-1p)
(CH₃)₂CH (1-3-1q)
(CH₃)₃C (1-3-1r)
CH₃(CH₂)₇ (1-3-1s)
Ph (1-3-1t)

(In Formulas (1-3-1p) to (1-3-1t), m is as defined above.)

Preferable examples of the urethane compound (1) include compounds represented by Formulas (1-1-30p), (1-1-30q), (1-1-30r), (1-1-30s), (1-1-30t), (1-1-41p), (1-1-41q), (1-1-41r), (1-1-41s), (1-1-41t), (1-1-45p), (1-1-45q), (1-1-45r), (1-1-45s), (1-1-45t), (1-1-46p), (1-1-46q), (1-1-46r), (1-1-46s), (1-1-46t), (1-1-48p), (1-1-48q), (1-1-48r), (1-1-48s), (1-1-48t), (1-1-52p), (1-1-52q), (1-1-52r), (1-1-52s), (1-1-52t), (1-1-59p), (1-1-59q), (1-1-59r), (1-1-59s), (1-1-59t), (1-1-88p), (1-1-88q), (1-1-88r), (1-1-88s), (1-1-88t), (1-1-89p), (1-1-89q), (1-1-89r), (1-1-89s), (1-1-89t), (1-1-90p), (1-1-90q), (1-1-90r), (1-1-90s), (1-1-90t), (1-2-20p), (1-2-20q), (1-2-20r), (1-2-20s), (1-2-20t), (1-2-41p), (1-2-41q), (1-2-41r), (1-2-41s), (1-2-41t), (1-2-48p), (1-2-48q), (1-2-48r), (1-2-48s), (1-2-48s), (1-2-49p), (1-2-49q), (1-2-49r), (1-2-49s), (1-2-49t), (1-2-51p), (1-2-51q), (1-2-51r), (1-2-51s), (1-2-51t), (1-2-54p), (1-2-54q), (1-2-54r), (1-2-54s), and (1-2-54t). Particularly preferable are compounds represented by Formulas (1-1-30r), (1-1-41r), (1-1-45r), (1-1-46r), (1-1-48r), (1-1-52p), (1-1-52q), (1-1-52r), (1-1-52s), (1-1-52t), (1-1-59r), (1-1-88r), (1-1-89r), (1-1-90r), (1-2 20r), (1-2-41r), (1-2-48r), (1-2-49r), (1-2-51r), and (1-2-54r).

Examples of the method for producing the urethane compound represented by Formula (1) include, but are not limited to, the following methods. Specifically, in the method for producing the amidate compound of the present invention, a urethane compound represented by Formula (1) is obtained by any one of the following methods, and the obtained urethane compound represented by Formula (1) is then reacted with a carboxylate compound represented by Formula (2).

Method I: A method comprising reacting an amine compound represented by Formula (4) below with a carbonyl compound represented by any one of Formulas (5a), (5b), and (5c) below (hereinafter referred to as carbonyl compound (5)).

Formula (4):

$$A\!-\![NH_2]_n \qquad (4)$$

(wherein A and n are as defined above).

Formula 5(a)

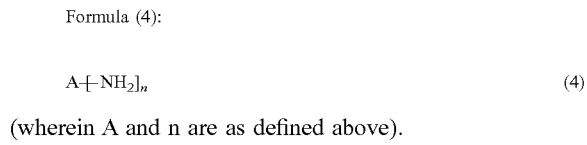

(wherein R¹ is as defined above).

Formula 5(b)

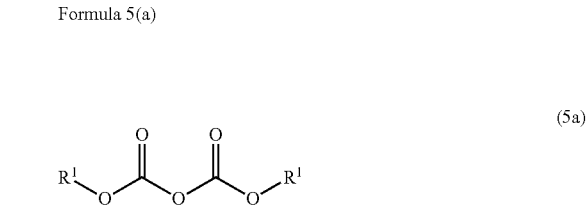

(wherein R¹ is as defined above).

Formula 5(c)

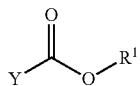

(5c)

(wherein R¹ is as defined above; and Y represents a halogen atom).

Method II: A method comprising reacting an amine compound represented by Formula (4) with phosgene, and then reacting the obtained reaction product with an alcohol compound.

Method III: A method comprising reacting an amine compound represented by Formula (4) with urea and an alcohol compound.

Method IV: A method comprising reacting an isocyanate compound represented by Formula (6) below with an alcohol compound represented by Formula (7) below.

Formula (6):

$$A\text{-}[\text{NCO}]_n \quad (6)$$

(wherein A and n are as defined above).

Formula (7):

$$R^1\text{—OH} \quad (7)$$

(wherein R¹ is as defined above).

The raw material compounds used in Method I, Method II, Method III, and Method IV can be known compounds, or compounds that can be produced by known organic synthesis methods.

Among these, Method I and Method IV are preferable in terms of ease of handling reagents, ease of reaction, ease of obtaining raw materials, etc. Method I and Method IV are described in detail below.

Method I is described.

In Formula (4), A and n are as defined above. Preferable examples of the amine compound represented by Formula (4) (hereinafter referred to as amine compound (4)) are amine compounds represented by any one of Formulas (4-1), (4-2), and (4-3) below. Amine compounds represented by Formula (4-1) or Formula (4-2) are particularly preferable.

Formula (4-1):

$$R^6\text{—NH}_2 \quad (4\text{-}1)$$

(wherein R⁶ is as defined above).

Formula (4-2):

$$H_2N\text{—}R^7\text{—}NH_2 \quad (4\text{-}2)$$

(wherein R⁷ is as defined above).

Formula (4-3):

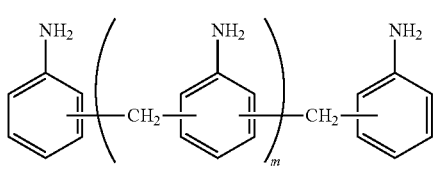

(4-3)

(wherein m is as defined above).

In Formula (4-1), R⁶ is as defined above.

In Formula (4-2), R⁷ is as defined above.

In Formula (4-3), m is as defined above.

Specific examples of the amine compound (4) are described below. However, the present invention is not limited thereto. In the specific examples below, Et represents ethyl, Pr represents n-propyl, and Bu represents n-butyl.

(4-1-1)

(4-1-2)

(4-1-3)

(4-1-4)

(4-1-5)

(4-1-6)

(4-1-7)

(4-1-8)

(4-1-9)

(4-1-10)

(4-1-11)

(4-1-12)

(4-1-13)

(4-1-14)

(4-1-15)

(4-1-16)

(4-1-17)

-continued

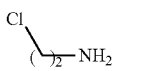 (4-1-18)

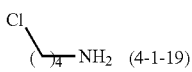 (4-1-19)

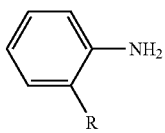

| R = | H | (4-1-20) |
|---|---|---|
| | CH$_3$ | (4-1-21) |
| | (CH$_2$)$_3$CH$_3$ | (4-1-22) |
| | (CH$_2$)$_7$CH$_3$ | (4-1-23) |
| | OCH$_3$ | (4-1-24) |
| | OCH$_2$CH$_3$ | (4-1-25) |
| | CH(CH$_3$)$_2$ | (4-1-26) |
| | C(CH$_3$)$_3$ | (4-1-27) |
| | N(CH$_3$)$_2$ | (4-1-28) |
| | F | (4-1-29) |
| | Cl | (4-1-30) |
| | Br | (4-1-31) |

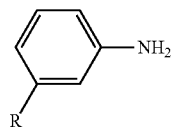

| R = CH$_3$ | (4-1-32) | R = CH$_3$ | (4-1-43) |
|---|---|---|---|
| (CH$_2$)$_3$CH$_3$ | (4-1-33) | (CH$_2$)$_3$CH$_3$ | (4-1-44) |
| (CH$_2$)$_7$CH$_3$ | (4-1-34) | (CH$_2$)$_7$CH$_3$ | (4-1-45) |
| OCH$_3$ | (4-1-35) | OCH$_3$ | (4-1-46) |
| OCH$_2$CH$_3$ | (4-1-36) | OCH$_2$CH$_3$ | (4-1-47) |
| CH(CH$_3$)$_2$ | (4-1-37) | CH(CH$_3$)$_2$ | (4-1-48) |
| C(CH$_3$)$_3$ | (4-1-38) | C(CH$_3$)$_3$ | (4-1-49) |
| N(CH$_3$)$_2$ | (4-1-39) | N(CH$_3$)$_2$ | (4-1-50) |
| F | (4-1-40) | F | (4-1-51) |
| Cl | (4-1-41) | Cl | (4-1-52) |
| Br | (4-1-42) | Br | (4-1-53) |

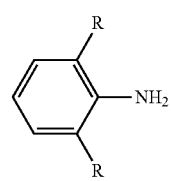

| R = CH$_3$ | (4-1-54) | R = CH$_3$ | (4-1-65) |
|---|---|---|---|
| (CH$_2$)$_3$CH$_3$ | (4-1-55) | (CH$_2$)$_3$CH$_3$ | (4-1-66) |
| (CH$_2$)$_7$CH$_3$ | (4-1-56) | (CH$_2$)$_7$CH$_3$ | (4-1-67) |
| OCH$_3$ | (4-1-57) | OCH$_3$ | (4-1-68) |
| OCH$_2$CH$_3$ | (4-1-58) | OCH$_2$CH$_3$ | (4-1-69) |
| CH(CH$_3$)$_2$ | (4-1-59) | CH(CH$_3$)$_2$ | (4-1-70) |
| C(CH$_3$)$_3$ | (4-1-60) | C(CH$_3$)$_3$ | (4-1-71) |
| N(CH$_3$)$_2$ | (4-1-61) | N(CH$_3$)$_2$ | (4-1-72) |
| F | (4-1-62) | F | (4-1-73) |
| Cl | (4-1-63) | Cl | (4-1-74) |
| Br | (4-1-64) | Br | (4-1-75) |

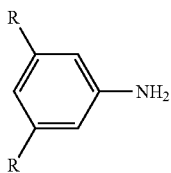

| R = CH$_3$ | (4-1-76) |
|---|---|
| (CH$_2$)$_3$CH$_3$ | (4-1-77) |
| (CH$_2$)$_7$CH$_3$ | (4-1-78) |
| OCH$_3$ | (4-1-79) |
| OCH$_2$CH$_3$ | (4-1-80) |
| CH(CH$_3$)$_2$ | (4-1-81) |
| C(CH$_3$)$_3$ | (4-1-82) |
| N(CH$_3$)$_2$ | (4-1-83) |
| F | (4-1-84) |
| Cl | (4-1-85) |
| Br | (4-1-86) |

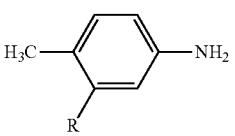 (4-1-87)

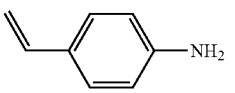 (4-1-88)

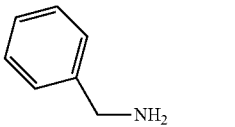 (4-1-89)

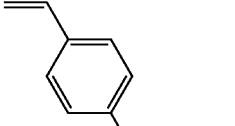 (4-1-90)

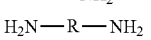
H$_2$N—R—NH$_2$

| R = | —CH$_2$— | (4-2-1) |
|---|---|---|
| | —CH$_2$CH$_2$— | (4-2-2) |
| | —CH$_2$(CH$_2$)$_2$CH$_2$— | (4-2-3) |
| | —CH$_2$(CH$_2$)$_4$CH$_2$— | (4-2-4) |
| | —CH$_2$(CH$_2$)$_6$CH$_2$— | (4-2-5) |
| | —CH$_2$(CH$_2$)$_8$CH$_2$— | (4-2-6) |
| | —CH$_2$(CH$_2$)$_{10}$CH$_2$— | (4-2-7) |

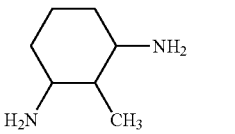 (4-2-8)

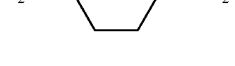 (4-2-9)

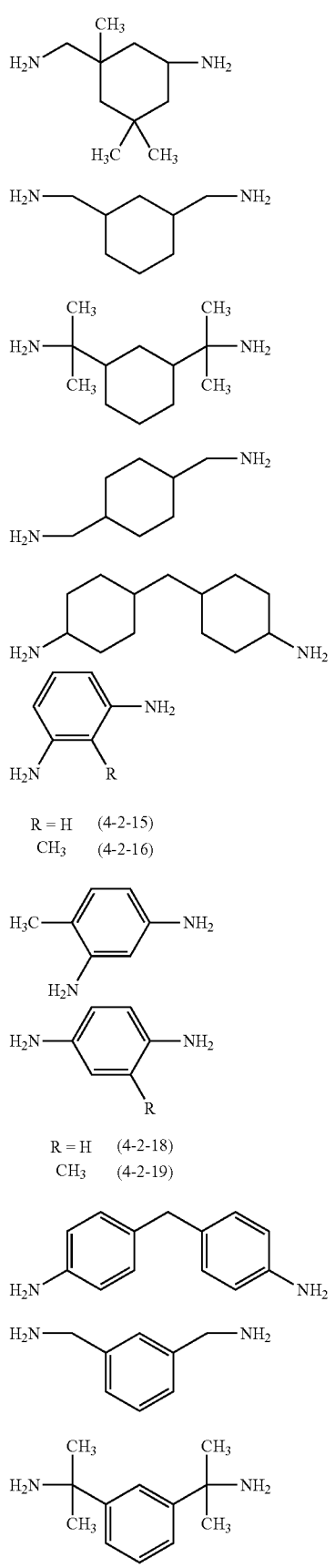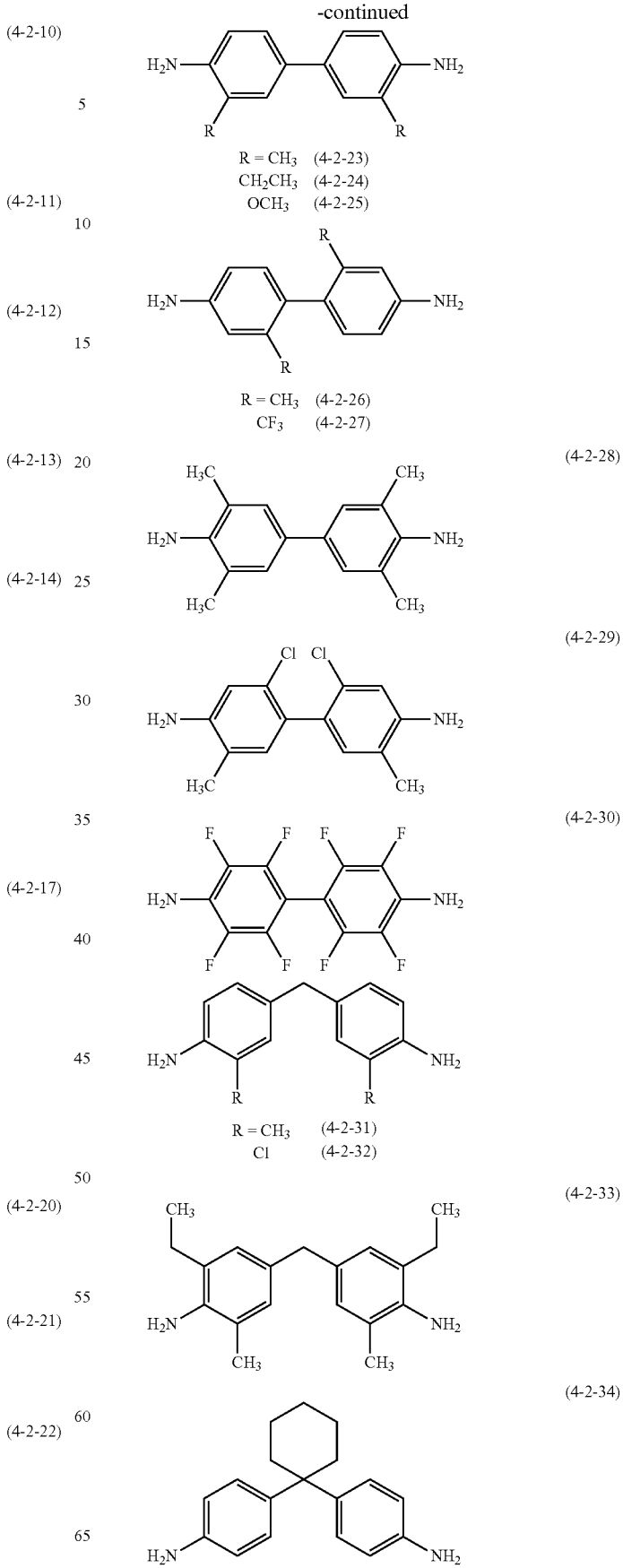

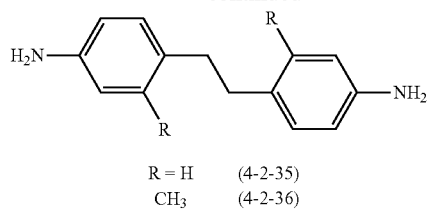
R = H (4-2-35)
CH₃ (4-2-36)
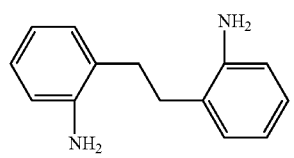
(4-2-37)
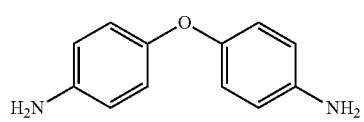
(4-2-38)
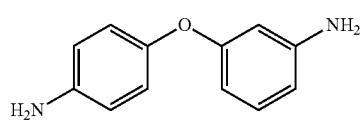
(4-2-39)
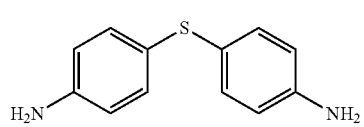
(4-2-40)
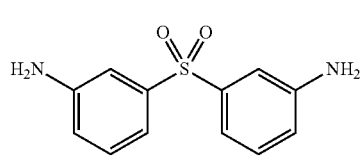
(4-2-41)
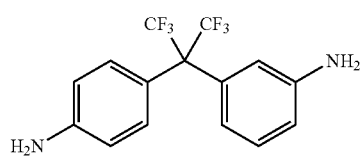
(4-2-42)
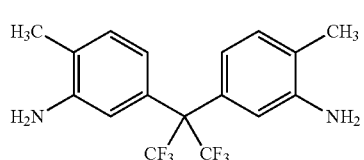
(4-2-43)
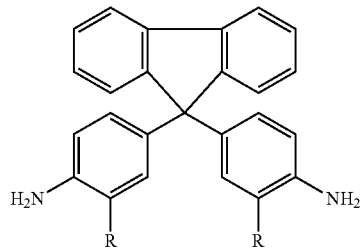
R = H (4-2-44)
CH₃ (4-2-45)
F (4-2-46)
Cl (4-2-47)
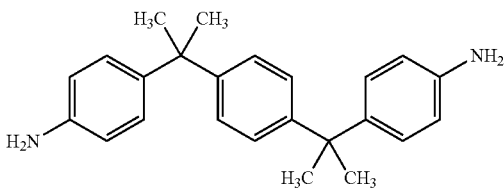
(4-2-48)
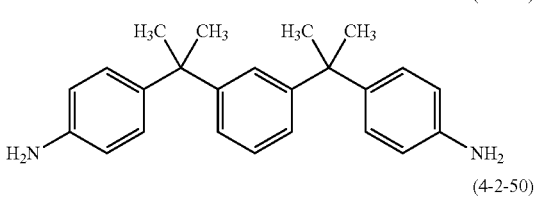
(4-2-49)
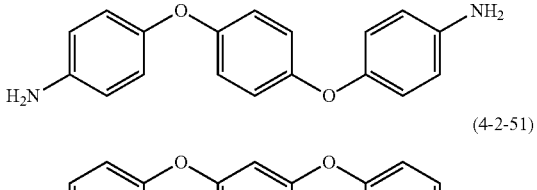
(4-2-50)
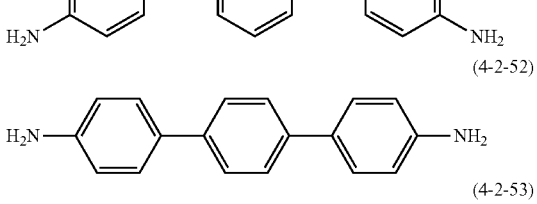
(4-2-51)
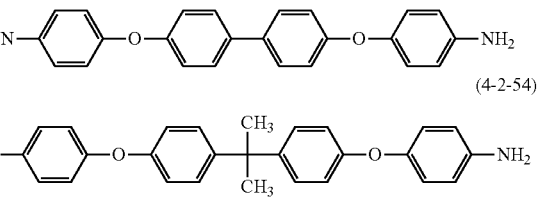
(4-2-52)
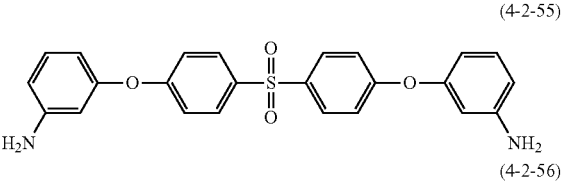
(4-2-53)
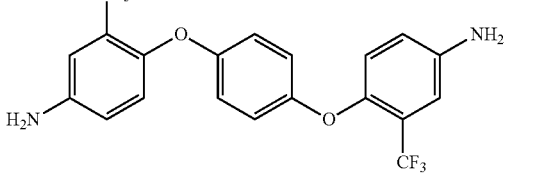
(4-2-54)
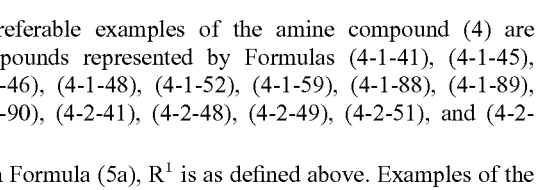
(4-2-55)
(4-2-56)
Preferable examples of the amine compound (4) are compounds represented by Formulas (4-1-41), (4-1-45), (4-1-46), (4-1-48), (4-1-52), (4-1-59), (4-1-88), (4-1-89), (4-1-90), (4-2-41), (4-2-48), (4-2-49), (4-2-51), and (4-2-54).
In Formula (5a), $R^1$ is as defined above. Examples of the carbonyl compound represented by Formula (5a) include di-t-butyl dicarbonate, dibenzyl dicarbonate, di-t-amyl dicarbonate, and diaryl dicarbonate; and preferably di-t-butyl dicarbonate and dibenzyl dicarbonate.

In Formula (5b), $R^1$ is as defined above. Examples of the carbonyl compound represented by Formula (5b) include dimethyl carbonate, diethyl carbonate, dipropyl carbonate, dibutyl carbonate, dipentyl carbonate, dihexyl carbonate, diphenyl carbonate, dibenzyl carbonate, and the like; and preferably dimethyl carbonate, diethyl carbonate, dipropyl carbonate, dibutyl carbonate, diphenyl carbonate, and dibenzyl carbonate.

In Formula (5c), $R^1$ is as defined above, and Y represents a halogen atom. Examples of the halogen atom include fluorine, chlorine, bromine, and iodine. The halogen atom is preferably chlorine. Examples of the carbonyl compound represented by Formula (5c) include methyl chloroformate, ethyl chloroformate, propyl chloroformate, isopropyl chloroformate, 2-methoxyethyl chloroformate, butyl chloroformate, isobutyl chloroformate, amyl chloroformate, heptyl chloroformate, hexyl chloroformate, nonyl chloroformate, n-octyl chloroformate, decyl chloroformate, dodecyl chloroformate, hexadecyl chloroformate, phenyl chloroformate, 2-naphthyl chloroformate, and benzyl chloroformate; and preferably methyl chloroformate, ethyl chloroformate, propyl chloroformate, isopropyl chloroformate, butyl chloroformate, n-octyl chloroformate, phenyl chloroformate, and benzyl chloroformate.

Among carbonyl compounds represented by Formula (5a), Formula (5b), and Formula (5c), carbonyl compounds represented by Formula (5a) or Formula (5b) are preferable in terms of ease of availability and ease of reaction. Carbonyl compounds represented by Formula (5a) are particularly preferable.

The amount of carbonyl compound (5) used is generally 1 mole or more, preferably 1 to 6 moles, per mole of amino groups in the amine compound (4).

When the amine compound (4) is reacted with the carbonyl compound (5), a base catalyst may be used, if necessary. Examples of the base catalyst include organic bases, such as triethylamine and dimethylaminopyridine; and inorganic bases, such as potassium hydroxide, sodium hydroxide, and sodium hydrogen carbonate. Triethylamine is preferable.

The optimal reaction temperature varies depending on the raw materials, solvents, etc., used, but is generally room temperature or higher, and preferably 20 to 250° C. In this specification, room temperature generally means about 20° C.

A solvent may or may not be used. When a solvent is used, the solvent used is not particularly limited, as long as it does not affect the reaction. Specific examples of solvents include aromatic hydrocarbon solvents, such as toluene, benzene, and xylene; hydrocarbon solvents, such as methylcyclohexane, cyclohexane, n-hexane, n-heptane, and octane; halogenated hydrocarbon solvents, such as dichloromethane and chloroform; ether solvents, such as diethyl ether, tetrahydrofuran (hereinafter abbreviated as THF), and 1,4-dioxane; alcohol solvents, such as methanol and ethanol; N,N-dimethylformamide, acetonitrile, and the like. Ether solvents and alcohol solvents are preferable, and tetrahydrofuran and methanol are particularly preferable. The amount of solvent used is generally 50 parts by weight or less, and preferably 0.1 to 10 parts by weight, per part by weight of the amine compound (4).

If necessary, the reaction may be performed in an inert gas atmosphere that does not affect the reaction, such as nitrogen, argon, or helium.

After completion of the reaction, the urethane compound (1) can be isolated by subjecting the unreacted carbonyl compound to treatment with an amine compound, such as diethanolamine, washing with water or a weak acidic aqueous solution, concentration of the reaction mixture, or the like. If necessary, the urethane compound (1) may be purified by recrystallization etc.

Method IV is described.

In Formula (6), A and n are as defined above. Preferable examples of the isocyanate compound represented by Formula (6) (hereinafter referred to as isocyanate compound (6)) include isocyanate compounds represented by any one of Formulas (6-1), (6-2), and (6-3). Isocyanate compounds represented by Formula (6-1) or Formula (6-2) are particularly preferable.

Formula (6-1):

$$R^6\text{—NCO} \quad (6\text{-}1)$$

(wherein $R^6$ is as defined above).

Formula (6-2):

$$\text{OCN—}R^7\text{—NCO} \quad (6\text{-}2)$$

(wherein $R^7$ is as defined above).

Formula (6-3)

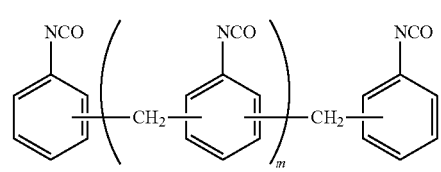

(6-3)

(wherein m is as defined above).

In Formula (6-1), $R^6$ is as defined above.
In Formula (6-2), $R^7$ is as defined above.
In Formula (6-3), m is as defined above.

Specific examples of the isocyanate compound (6) are described below. However, the present invention is not limited thereto. In the specific examples below, Et represents ethyl, Pr represents n-propyl, and Bu represents n-butyl.

$$H_3C\text{—NCO} \quad (6\text{-}1\text{-}1)$$

$$Et\text{—NCO} \quad (6\text{-}1\text{-}2)$$

$$Pr\text{—NCO} \quad (6\text{-}1\text{-}3)$$

$$\begin{array}{c} H_3C \\ \phantom{H_3C}\diagdown \\ \phantom{H_3C}\phantom{\diagdown}\text{—NCO} \\ \phantom{H_3C}\diagup \\ H_3C \end{array} \quad (6\text{-}1\text{-}4)$$

$$Bu\text{—NCO} \quad (6\text{-}1\text{-}5)$$

$$\begin{array}{c} \phantom{H_3C\text{—}}CH_3 \\ H_3C\text{—}{\overset{|}{\underset{|}{C}}}\text{—NCO} \\ \phantom{H_3C\text{—}}CH_3 \end{array} \quad (6\text{-}1\text{-}6)$$

$$H_3C\underset{4}{\diagdown}\text{—NCO} \quad (6\text{-}1\text{-}7)$$

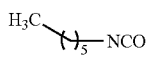 (6-1-8)

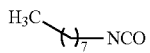 (6-1-9)

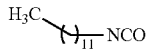 (6-1-10)

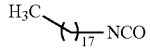 (6-1-11)

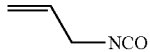 (6-1-12)

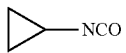 (6-1-13)

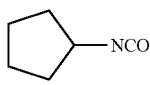 (6-1-14)

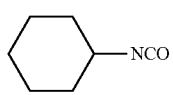 (6-1-15)

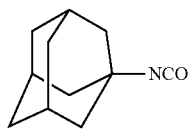 (6-1-16)

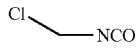 (6-1-17)

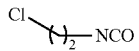 (6-1-18)

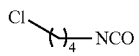 (6-1-19)

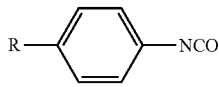

R = H           (6-1-20)
CH$_3$          (6-1-21)
(CH$_2$)$_3$CH$_3$ (6-1-22)
(CH$_2$)$_7$CH$_3$ (6-1-23)
OCH$_3$         (6-1-24)
OCH$_2$CH$_3$   (6-1-25)
CH(CH$_3$)$_2$  (6-1-26)
C(CH$_3$)$_3$   (6-1-27)
N(CH$_3$)$_2$   (6-1-28)
F               (6-1-29)
Cl              (6-1-30)
Br              (6-1-31)

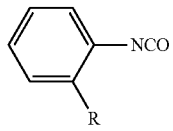

R = CH$_3$        (6-1-32)
(CH$_2$)$_3$CH$_3$ (6-1-33)
(CH$_2$)$_7$CH$_3$ (6-1-34)
OCH$_3$           (6-1-35)
OCH$_2$CH$_3$     (6-1-36)
CH(CH$_3$)$_2$    (6-1-37)
C(CH$_3$)$_3$     (6-1-38)
N(CH$_3$)$_2$     (6-1-39)
F                 (6-1-40)
Cl                (6-1-41)
Br                (6-1-42)

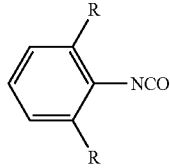

R = CH$_3$         (6-1-43)
(CH$_2$)$_3$CH$_3$ (6-1-44)
(CH$_2$)$_7$CH$_3$ (6-1-45)
OCH$_3$            (6-1-46)
OCH$_2$CH$_3$      (6-1-47)
CH(CH$_3$)$_2$     (6-1-48)
C(CH$_3$)$_3$      (6-1-49)
N(CH$_3$)$_2$      (6-1-50)
F                  (6-1-51)
Cl                 (6-1-52)
Br                 (6-1-53)

R = CH$_3$         (6-1-54)
(CH$_2$)$_3$CH$_3$ (6-1-55)
(CH$_2$)$_7$CH$_3$ (6-1-56)
OCH$_3$            (6-1-57)
OCH$_2$CH$_3$      (6-1-58)
CH(CH$_3$)$_2$     (6-1-59)
C(CH$_3$)$_3$      (6-1-60)
N(CH$_3$)$_2$      (6-1-61)
F                  (6-1-62)
Cl                 (6-1-63)
Br                 (6-1-64)

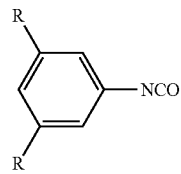

R = CH$_3$         (6-1-65)
(CH$_2$)$_3$CH$_3$ (6-1-66)
(CH$_2$)$_7$CH$_3$ (6-1-67)
OCH$_3$            (6-1-68)
OCH$_2$CH$_3$      (6-1-69)
CH(CH$_3$)$_2$     (6-1-70)
C(CH$_3$)$_3$      (6-1-71)
N(CH$_3$)$_2$      (6-1-72)
F                  (6-1-73)
Cl                 (6-1-74)
Br                 (6-1-75)

R = CH$_3$         (6-1-76)
(CH$_2$)$_3$CH$_3$ (6-1-77)
(CH$_2$)$_7$CH$_3$ (6-1-78)
OCH$_3$            (6-1-79)
OCH$_2$CH$_3$      (6-1-80)
CH(CH$_3$)$_2$     (6-1-81)
C(CH$_3$)$_3$      (6-1-82)
N(CH$_3$)$_2$      (6-1-83)
F                  (6-1-84)
Cl                 (6-1-85)
Br                 (6-1-86)

(6-1-87)

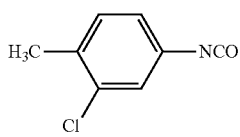

(6-1-88)

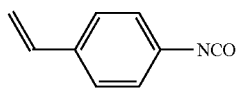

(6-1-89)

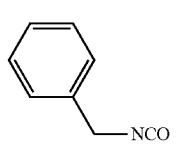

(6-1-90)

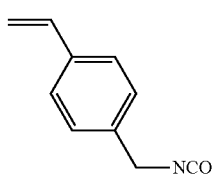

OCN—R—NCO
R =
—CH₂—   (6-2-1)
—CH₂CH₂—   (6-2-2)
—CH₂(CH₂)₂CH₂—   (6-2-3)
—CH₂(CH₂)₄CH₂—   (6-2-4)
—CH₂(CH₂)₆CH₂—   (6-2-5)
—CH₂(CH₂)₈CH₂—   (6-2-6)
—CH₂(CH₂)₁₀CH₂—   (6-2-7)

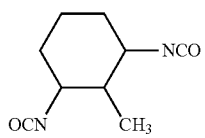
(6-2-8)

(6-2-9)

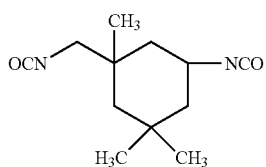
(6-2-10)

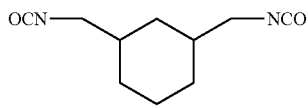
(6-2-11)

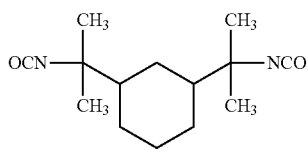
(6-2-12)

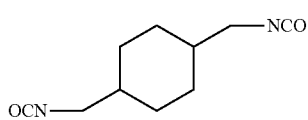
(6-2-13)

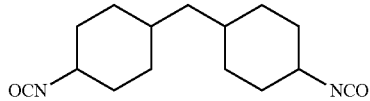
(6-2-14)

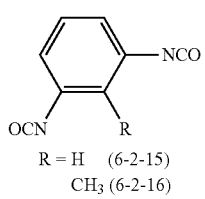
R = H  (6-2-15)
CH₃  (6-2-16)

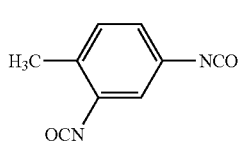
(6-2-17)

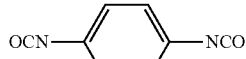
R = H  (6-2-18)
CH₃  (6-2-19)

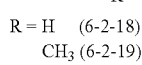
(6-2-20)

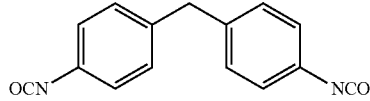
(6-2-21)

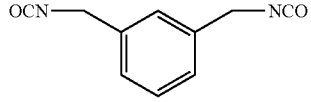
(6-2-22)

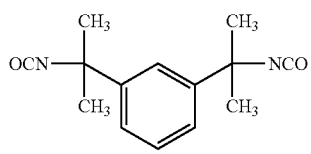

Preferable examples of the isocyanate compound (6) include compounds represented by Formulas (6-1-5), (6-1-20), (6-1-30), (6-1-52), (6-2-17), and (6-2-20).

In Formula (7), $R^1$ is as defined above. Examples of the alcohol compound represented by Formula (7) (hereinafter referred to as alcohol compound (7)) include aliphatic alcohols, such as methanol, ethanol, isopropanol, t-butanol, n-octanol, methoxyethanol, and ethoxyethanol; aromatic alcohols, such as benzyl alcohol; and phenols, such as phenol. Methanol, ethanol, isopropanol, t-butanol, n-octanol, and phenol are preferable.

The amount of the alcohol compound (7) used is generally 1 mole or more, and preferably 1 to 70 moles, per mole of isocyanate groups in the isocyanate compound (6).

The optimal reaction temperature for reacting the isocyanate compound (6) with the alcohol compound (7) varies depending on the raw materials, solvents, etc., used, but is generally room temperature or higher, and preferably 20 to 200° C.

When the isocyanate compound (6) is reacted with the alcohol compound (7), a catalyst may be used, if necessary. Examples of catalysts include organometallic compounds containing at least one metal element selected from the group consisting of tin, iron, lead, bismuth, mercury, titanium, hafnium, and zirconium; amine compounds; and the like. Preferable examples of organometallic compounds include tin carboxylate, dialkyltin oxide, and bismuth carboxylate; and more preferably dibutyltin dilaurate. Preferable examples of amine compounds include 1,4-diazabicyclo[2.2.2]octane, N,N,N',N'',N''-pentamethyldiethylenetriamine, and bis(2-dimethylaminoethyl) ether.

A solvent may or may not be used. The alcohol compound (7) can also be used as a solvent by using an excess of the alcohol compound (7). When a solvent is further used, in addition to the alcohol compound (7), the solvent used is not particularly limited, as long as it does not affect the reaction. Specific examples of the solvent include aromatic hydrocarbon solvents, such as toluene, benzene and xylene; hydrocarbon solvents, such as methylcyclohexane, cyclohexane, n-hexane, n-heptane, and octane; halogenated hydrocarbon solvents, such as dichloromethane and chloroform; ether solvents, such as diethyl ether and THF; and the like. Toluene is preferable. When such a solvent is used, the amount of solvent is generally 50 parts by weight or less, preferably 0.1 to 10 parts by weight, per part by weight of the isocyanate compound (6).

If necessary, the reaction may be performed in an inert gas atmosphere that does not affect the reaction, such as nitrogen, argon, or helium.

After completion of the reaction, the urethane compound (1) can be isolated by concentrating the reaction mixture. If necessary, the obtained urethane compound (1) can be purified by, for example, washing with any solvent, or recrystallization.

Next, the carboxylate compound represented by formula (2) (hereinafter referred to as carboxylate compound (2)) is described.

In Formula (2), $R^2$, $R^3$, $R^4$, and $R^5$ each independently represent a hydrocarbon group that may contain a heteroatom. Some or all of $R^2$, $R^3$, $R^4$, and $R^5$ may be bonded together to form a ring structure. For example, $R^2$ and $R^3$; $R^2$ and $R^4$; $R^2$ and $R^5$; $R^3$ and $R^4$; $R^3$ and $R^5$; $R^4$ and $R^5$; or $R^2$, $R^3$, $R^4$, and $R^5$ may be bonded together to form a ring structure. Examples of the hydrocarbon group that may contain a heteroatom include methyl, ethyl, propyl, isopropyl, n-butyl, s-butyl, t-butyl, n-pentyl, n-hexyl, n-octyl, n-decyl, n-dodecyl, allyl, benzyl, cyclohexyl, adamantyl, phenyl, 2,6-diisopropylphenyl, 2,4,6-trimethylphenyl, 2-methoxyethyl, 2-ethoxyethyl, 2-(dimethylamino)ethyl, and the like; preferably methyl, ethyl, propyl, isopropyl, t-butyl, n-octyl, cyclopentyl, cyclohexyl, and 2,4,6-trimethylphenyl; more preferably methyl, ethyl, isopropyl, t-butyl, n-octyl, and phenyl; and particularly preferably methyl, isopropyl, t-butyl, n-octyl, and phenyl. X is a nitrogen atom, an oxygen atom, or a sulfur atom; and preferably a nitrogen atom. When X represents a nitrogen atom, a is 1. When X represents an oxygen atom or a sulfur atom, a is 0. In other words, when X is an oxygen atom or a sulfur atom, there is no $R^5$.

In the present invention, it is preferable in view of ease of availability that $R^3$ and $R^4$ in the carboxylate compound represented by Formula (2) are bound to each other to form a ring structure. Preferred examples of the carboxylate compound (2) that forms a ring include carboxylate compounds represented by any one of the following Formulas (2-1), (2-2), and (2-3). Carboxylate compounds represented by Formula (2-1) are particularly preferable.

Formula (2-1)

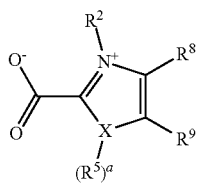

(2-1)

(wherein $R^2$, $R^5$, X, and a are as defined above; and $R^8$ and $R^9$ each represent a hydrogen atom, or a $C_{1-6}$ hydrocarbon group that may contain a heteroatom).

Formula (2-2)

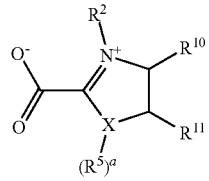

(2-2)

(wherein $R^2$, $R^5$, X, and a are as defined above; and $R^{10}$ and $R^{11}$ each represent a hydrogen atom, or a $C_{1-6}$ hydrocarbon group that may contain a heteroatom).

Formula (2-3)

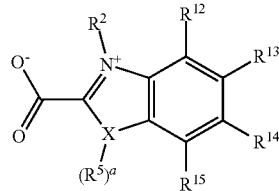

(2-3)

(wherein $R^2$, $R^5$, X, and a are as defined above; and $R^{12}$, $R^{13}$, $R^{14}$, and $R^{15}$ each represent a hydrogen atom, or a $C_{1-6}$ hydrocarbon group that may contain a heteroatom).

In Formula (2-1), $R^2$, $R^5$, X, and a are as defined above. Re and $R^9$ each independently represent a hydrogen atom, or a $C_1$-$C_6$ hydrocarbon group that may contain a heteroatom. Preferably, $R^8$ and $R^9$ each represent a hydrogen atom. Examples of the $C_1$-$C_6$ hydrocarbon group that may contain a heteroatom include methyl, ethyl, propyl, isopropyl, n-butyl, s-butyl, t-butyl, pentyl, hexyl, cyclohexyl, phenyl, 2-methoxyethyl, 2-ethoxyethyl, 2-(dimethylamino)ethyl, and the like. Methyl is preferable.

Specific examples of carboxylate compounds represented by Formula (2-1) include 1,3-dimethylimidazolium-2-carboxylate, 1-ethyl-3-methylimidazolium-2-carboxylate, 1-methyl-3-propylimidazolium-2-carboxylate, 1-methyl-3-isopropylimidazolium-2-carboxylate, 1-butyl-3-methylimidazolium-2-carboxylate, 1-tert-butyl-3-methylimidazolium-2-carboxylate, 1-methyl-3-pentylimidazolium-2-carboxylate, 1-hexyl-3-methylimidazolium-2-carboxylate, 1-heptyl-3-methylimidazolium-2-carboxylate, 1-methyl-3-octylimidazolium-2-carboxylate, 1-methyl-3-nonylimidazolium-2-carboxylate, 1-decyl-3-methylimidazolium-2-carboxylate, 1-allyl-3-methylimidazolium-2-carboxylate, 1-benzyl-3-methyl imidazolium-2-carboxylate, 1-(2-methoxyethyl)-3-methylimidazolium-2-carboxylate, 1-(2-ethoxyethyl)-3-methyl imidazolium-2-carboxylate, 1-(2-dimethylaminoethyl)-3-methylimidazolium-2-carboxylate, 1,3,4,5-tetramethylimidazolium-2-carboxylate, 3-methyloxazolium-2-carboxylate, 3,5-dimethyloxazolium-2-carboxylate, 3,4,5-trimethyloxazolium-2-carboxylate, 3-methylthiazolium-2-carboxylate, 3,4-dimethylthiazolium-2-carboxylate, 3,5-dimethylthiazolium-2-carboxylate, 3,4,5-trimethylthiazolium-2-carboxylate, and the like; preferably 1,3-dimethylimidazolium-2-carboxylate, 1-ethyl-3-methylimidazolium-2-carboxylate, 1-methyl-3-propylimidazolium-2-carboxylate, 1-butyl-3-methylimidazolium-2-carboxylate, and 1-methyl-3-octylimidazolium-2-carboxylate; and particularly preferably 1,3-dimethylimidazolium-2-carboxylate and 1-methyl-3-octylimidazolium-2-carboxylate.

In Formula (2-2), $R^2$, $R^5$, X, and a are as defined above. $R^{10}$ and $R^{11}$ independently represent a hydrogen atom, or a $C_1$-$C_6$ hydrocarbon group that may contain a heteroatom. Preferably, $R^{10}$ and $R^{11}$ each represent a hydrogen atom. Examples of the $C_1$-$C_6$ hydrocarbon group that may contain a heteroatom include methyl, ethyl, propyl, isopropyl, n-butyl, s-butyl, t-butyl, pentyl, hexyl, cyclohexyl, phenyl, 2-methoxyethyl, 2-ethoxyethyl, 2-(dimethylamino)ethyl, and the like. Methyl is preferable.

Specific examples of carboxylate compounds represented by Formula (2-2) include 1,3-dimethylimidazolinium-2-carboxylate, 1-ethyl-3-methylimidazolinium-2-carboxylate, 1-methyl-3-propylimidazolinium-2-carboxylate, 1-butyl-3-methylimidazolinium-2-carboxylate, 1-methyl-3-pentylimidazolinium-2-carboxylate, 1-hexyl-3-methylimidazolinium-2-carboxylate, 1-heptyl-3-methylimidazolinium-2-carboxylate, 1-methyl-3-octylimidazolinium-2-carboxylate, 1-methyl-3-nonylimidazolinium-2-carboxylate, 1-decyl-3-methylimidazolinium-2-carboxylate, 1-allyl-3-methylimidazolinium-2-carboxylate, 1-benzyl-3-methylimidazolinium-2-carboxylate, 1-(2-methoxyethyl)-3-methylimidazolinium-2-carboxylate, 1-(2-ethoxyethyl)-3-methylimidazolinium-2-carboxylate, 1-(2-dimethylaminoethyl)-3-methylimidazolinium-2-carboxylate, 1,3,4,5-tetramethylimidazolinium-2-carboxyrate, 3-methyloxazolinium-2-carboxylate, 3,4-dimethyloxazolinium-2-carboxylate, 3,5-dimethyloxazolinium-2-carboxylate, 3,4,5-trimethyloxazolinium-2-carboxylate, 3-methylthiazolinium-2-carboxylate, 3,4-dimethylthiazolinium-2-carboxylate, 3,5-dimethylthiazolinium-2-carboxylate, 3,4,5-trimethylthiazolinium-2-carboxylate, and the like; preferably 1,3-dimethylimidazolinium-2-carboxylate, 1-ethyl-3-methyl imidazolinium-2-carboxylate, 1-methyl-3-propylimidazolinium-2-carboxylate, 1-butyl-3-methylimidazolinium-2-carboxylate, and 1-methyl-3-octylimidazolinium-2-carboxylate; and particularly preferably 1,3-dimethylimidazolinium-2-carboxylate and 1-methyl-3-octylimidazolinium-2-carboxylate.

In Formula (2-3), $R^2$, $R^5$, X, and a are as defined above. $R^{12}$, $R^{13}$, $R^{14}$, and $R^{15}$ independently represent a hydrogen atom, or a $C_1$-$C_6$ hydrocarbon group that may contain a heteroatom. Preferably, $R^{12}$, $R^{13}$, $R^{14}$, and $R^{15}$ represent a hydrogen atom. Examples of the $C_1$-$C_6$ hydrocarbon group that may contain a heteroatom include methyl, ethyl, propyl, isopropyl, n-butyl, s-butyl, t-butyl, pentyl, hexyl, cyclohexyl, phenyl, 2-methoxyethyl, 2-ethoxyethyl, 2-(dimethylamino)ethyl, and the like. Methyl is preferable.

Specific examples of carboxylate compounds represented by Formula (2-3) include 1,3-dimethylbenzimidazolium-2-carboxylate, 1-ethyl-3-methylbenzimidazolium-2-carboxylate, 1-methyl-3-propylbenzimidazolium-2-carboxylate, 1-butyl-3-methylbenzimidazolium-2-carboxylate, 1-methyl-3-pentylbenzimidazolium-2-carboxylate, 1-hexyl-3-methylbenzimidazolium-2-carboxylate, 1-heptyl-3-methylbenzimidazolium-2-carboxylate, 1-methyl-3-octylbenzimidazolium-2-carboxylate, 1-methyl-3-nonylbenzimidazolium-2-carboxylate, 1-decyl-3-methylbenzimidazolium-2-carboxylate, 1-allyl-3-methylbenzimidazolium-2-carboxylate, 1-benzyl-3-methylbenzimidazolium-2-carboxylate, 1,3,6-trimethylbenzimidazolium-2-carboxylate, 1-acetyl-3,6-dimethylbenzimidazolium-2-carboxylate, 1,3,6,7-tetramethylbenzimidazolium-2-carboxylate, 1,3-dibenzyl-6,7-dimethylbenzimidazolium-2-carboxylate, 3-methylbenzoxazolium-2-carboxylate, 3-methylbenzothiazolium-2-carboxylate, and the like; preferably 1,3-dimethylbenzimidazolium-2-carboxylate, 1-ethyl-3-methylbenzimidazolium-2-carboxylate, 1-methyl-3-propylbenzimidazolium-2-carboxylate, and 1-butyl-3-methylbenzimidazolium-2-carboxylate; and particularly preferably 1,3-dimethylbenzimidazolium-2-carboxylate.

The carboxylate compound (2) can be produced by various methods. Examples of production methods include, but are not limited to, the following methods.

Method (V): A method comprising reacting a nitrogen-containing organic compound represented by Formula (8) below (hereinafter referred to as nitrogen-containing organic compound (8)) with a dialkyl carbonate compound represented by Formula (9) (hereinafter referred to as dialkyl carbonate compound (9)).

Formula (8)

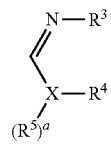

(wherein $R^3$, $R^4$, $R^5$, X, and a are as defined above).

Formula (9)

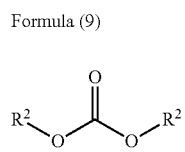

(wherein $R^2$ is as defined above).

Method VI: A method comprising allowing a strong base to act on a carbene precursor, such as 1,3-dialkylimidazolium chloride, to obtain a carbene compound; and adding carbon dioxide to the obtained carbene compound.

The raw material compounds used in Method V and Method VI can be known compounds, or compounds that can be produced by known organic synthesis methods.

Among these, Method V is preferable in terms of ease of handling reagents, ease of reaction, ease of obtaining raw materials, etc. Method V is explained in detail below.

In Formula (8), $R^3$, $R^4$, $R^5$, X, and a are as defined above. In the present invention, it is preferable in terms of ease of availability that $R^3$ and $R^4$ in Formula (8) are bonded together to form a ring structure. Preferable examples of the nitrogen-containing organic compound (8) that forms a ring include nitrogen-containing organic compounds represented by any one of the following Formulas (8-1), (8-2), and (8-3). Nitrogen-containing organic compounds represented by Formula (8-1) are particularly preferable.

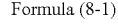
Formula (8-1)

(wherein $R^5$, $R^8$, $R^9$, X, and a are as defined above).

Formula (8-2)

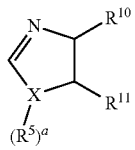

(8-2)

(wherein $R^5$, $R^{10}$, $R^{11}$, X, and a are as defined above).

Formula (8-3)

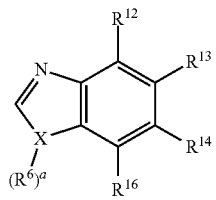

(8-3)

(wherein $R^5$, $R^{12}$, $R^{13}$, $R^{14}$, $R^{15}$, X, and a are as defined above).

In Formula (8-1), $R^5$, $R^8$, $R^9$, X, and a are as defined above. Specific examples of nitrogen-containing compounds represented by Formula (8-1) include 1-methylimidazole, 1-ethylimidazole, 1-propylimidazole, 1-isopropylimidazole, 1-butylimidazole, 1-tert-butylimidazole, 1-pentylimidazole, 1-hexylimidazole, 1-heptylimidazole, 1-octylimidazole, 1-nonylimidazole, 1-decylimidazole, 1-allylimidazole, 1-benzylimidazole, 1-(2-methoxyethyl) imidazole, 1-(2-ethoxyethyl) imidazole, 1-(2-dimethylaminoethyl)imidazole, 1,4,5-trimethylimidazole, oxazole, 5-methyloxazole, 4,5-dimethyloxazole, thiazole, 4-methylthiazole, 5-methylthiazole, 4,5-dimethylthiazole, and the like; preferably 1-methylimidazole, 1-ethylimidazole, 1-propylimidazole, 1-butylimidazole, and 1-octylimidazole; and particularly preferably 1-methylimidazole and 1-octylimidazole.

In Formula (8-2), $R^5$, $R^{10}$, $R^{11}$, X, and a are as defined above. Specific examples of nitrogen-containing compounds represented by Formula (8-2) include 1-methylimidazoline, 1-ethylimidazoline, 1-propylimidazoline, 1-isopropylimidazoline, 1-butylimidazoline, 1-tert-butylimidazoline, 1-pentylimidazoline, 1-hexylimidazoline, 1-heptylimidazoline, 1-octylimidazoline, 1-nonylimidazoline, 1-decylimidazoline, 1-allylimidazoline, 1-benzylimidazoline, 1-(2-methoxyethyl)imidazoline, 1-(2-ethoxyethyl) imidazoline, 1-(2-dimethylaminoethyl) imidazoline, 1,4,5-trimethylimidazoline, oxazoline, 4-methyloxazoline, 5-methyloxazoline, 4,5-dimethyloxazoline, thiazoline, 4-methylthiazoline, 5-methylthiazoline, 4,5-dimethylthiazoline, and the like; preferably 1-methylimidazoline, 1-ethylimidazoline, 1-propylimidazoline, 1-butylimidazoline, and 1-octylimidazoline; and particularly preferably 1-methylimidazoline and 1-octylimidazoline.

In Formula (8-3), $R^5$, $R^{12}$, $R^{13}$, $R^{14}$, $R^{15}$, X, and a are as defined above. Specific examples of nitrogen-containing compounds represented by Formula (8-3) include 1-methylbenzimidazole, 1-ethylbenzimidazole, 1-propylbenzimidazole, 1-butylbenzimidazole, 1-pentylbenzimidazole, 1-hexylbenzimidazole, 1-heptylbenzimidazole, 1-octylbenzimidazole, 1-nonylbenzimidazole, 1-decylbenzimidazole, 1-allylbenzimidazole, 1-benzylbenzimidazole, 1,6-dimethylbenzimidazole, 1-acetyl-6-methylbenzimidazole, 1,6,7-trimethylbenzimidazole, benzoxazole, benzothiazole, and the like; preferably 1-methylbenzimidazole, 1-ethylbenzimidazole, 1-propylbenzimidazole, and 1-butylbenzimidazole; and particularly preferably 1-methylbenzimidazole.

In Formula (9), $R^2$ is as defined above. Specific examples of the dialkyl carbonate compound (9) include dimethyl carbonate, diethyl carbonate, dipropyl carbonate, dibutyl carbonate, dipentyl carbonate, dihexyl carbonate, and the like; preferably dimethyl carbonate, diethyl carbonate, dipropyl carbonate, and dibutyl carbonate; and particularly preferably dimethyl carbonate.

The amount of the dialkyl carbonate compound (9) used is generally 1 mole or more, preferably 1 to 6 moles, per mole of the nitrogen-containing organic compound (8).

The optimal reaction temperature varies depending on the raw materials, solvents, etc., used, but is generally room temperature or higher, and preferably 20 to 200° C.

A solvent may or may not be used. When a solvent is used, the solvent used is not particularly limited, as long as it does not affect the reaction. Specific examples of solvents include monohydric alcohol solvents such as methanol, ethanol, propanol, butanol, pentanol, hexanol, 1-methoxy-2-propanol, and ethoxyethanol; polyol solvents such as ethylene glycol, propylene glycol, and diethylene glycol; and glycol monoalkyl ether solvents such as dipropylene glycol mono-n-butyl ether, dipropylene glycol monomethyl ether, tripropylene glycol monomethyl ether, propylene glycol mono-n-propyl ether, dipropylene glycol mono-n-propyl ether, propylene glycol mono-n-butyl ether, tripropylene glycol mono-n-butyl ether, propylene glycol monomethyl ether, and diethylene glycol monoethyl ether. Monohydric alcohol solvents are preferable, and methanol is particularly preferable. When a solvent is used, the amount of solvent used is generally 50 parts by weight or less, preferably 10 parts by weight or less, and more preferably 0.1 to 10 parts by weight, per part by weight of the nitrogen-containing organic compound (8).

If necessary, the reaction may be performed in an inert gas atmosphere that does not affect the reaction, such as nitrogen, argon, or helium.

After completion of the reaction, the carboxylate compound (2) can be isolated by concentrating the reaction mixture and removing the solvent. When an unreacted nitrogen-containing organic compound (8) and/or dialkyl carbonate compound (9) remains in the reaction mixture, these compounds can also be removed by concentrating the reaction mixture. Alternatively, the reaction mixture containing the carboxylate compound (2) can be directly used for the reaction with the urethane compound (1) without isolating the carboxylate compound (2) from the reaction mixture. This method does not require a concentration step and simplifies the production process; therefore, it is advantageous for industrial production. Accordingly, in the present invention, it is preferable to use the reaction mixture as it for the reaction with the urethane compound (1).

The amidate compound represented by Formula (3) is described below.

A, $R^2$, $R^3$, $R^4$, $R^5$, X, n, and a in Formula (3) are as defined above. Preferable examples of the amidate compound represented by Formula (3) (hereinafter referred to as amidate compound (3)) include amidate compounds represented by any one of Formulas (3-1), (3-2), and (3-3). Amidate compounds represented by Formula (3-1) or Formula (3-2) are particularly preferable.

Formula (3-1)

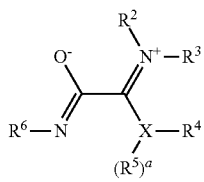

(3-1)

(wherein R², R³, R⁴, R⁵, R⁶, X, and a are as defined above).

Formula (3-2)

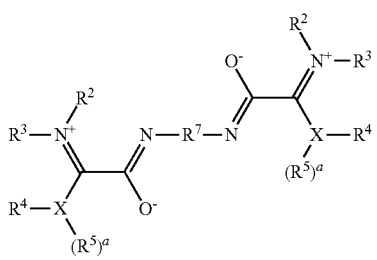

(3-2)

(wherein R², R³, R⁴, R⁵, R⁷, X, and a are as defined above).

Formula (3-3)

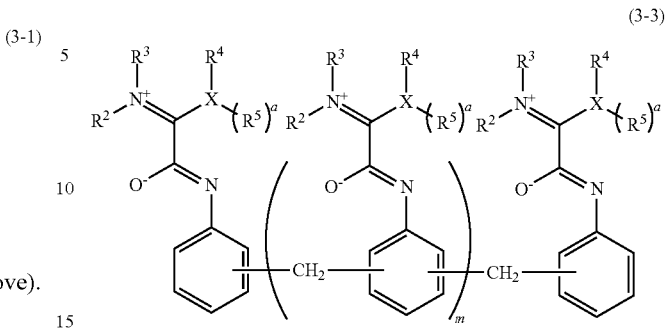

(3-3)

(wherein R², R³, R⁴, R⁵, X, m, and a are as defined above).

In Formula (3-1), R², R³, R⁴, R⁵, R⁶, X, and a are as defined above.

In Formula (3-2), R², R³, R⁴, R⁵, R⁶, R⁷, X, and a are as defined above.

In Formula (3-3), R², R³, R⁴, R⁵, X, m, and a are as defined above.

In Formula (3-1), Formula (3-2), and Formula (3-3), multiple R², R³, R⁴, R⁵, R⁶, and X may be the same as or different from each other.

Specific examples of the amidate compound (3) are described below. However, the present invention is not limited thereto. In the specific examples below, Et represents ethyl, Pr represents n-propyl, and Bu represents n-butyl.

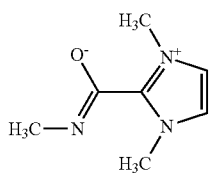

(3-1-1a)

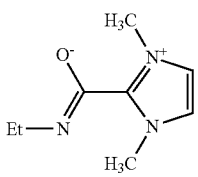

(3-1-2a)

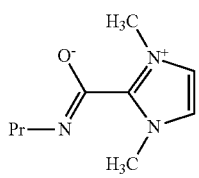

(3-1-3a)

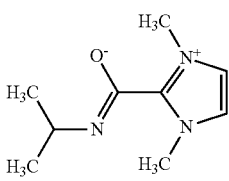

(3-1-4a)

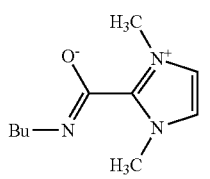

(3-1-5a)

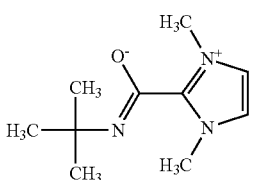

(3-1-6a)

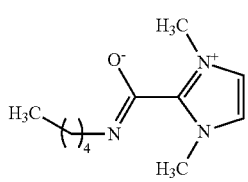

(3-1-7a)

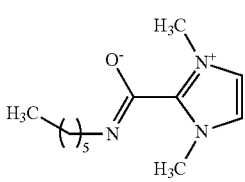

(3-1-8a)

-continued
(3-1-9a) 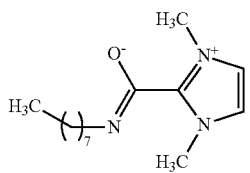
(3-1-10a) 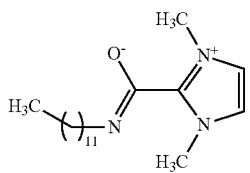
(3-1-11a) 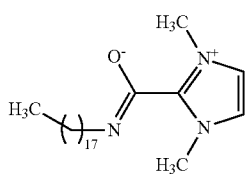
(3-1-12a) 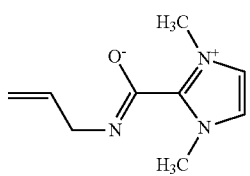
(3-1-13a) 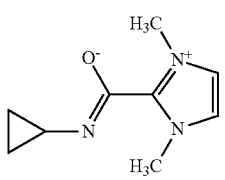
(3-1-14a) 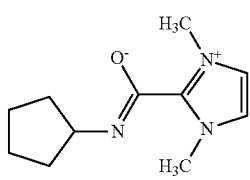
(3-1-15a) 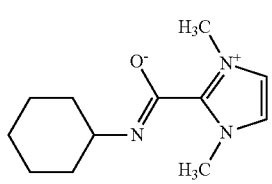
(3-1-16a) 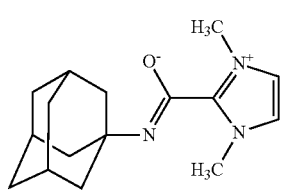
(3-1-17a) 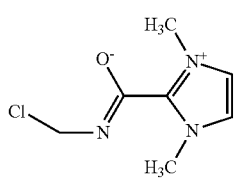
(3-1-18a) 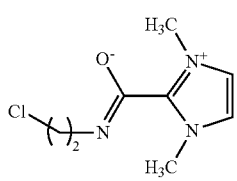
(3-1-19a) 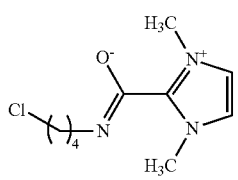
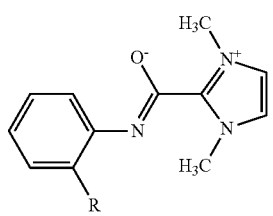
R = H (3-1-20a)
CH$_3$ (3-1-21a)
(CH$_2$)$_3$CH$_3$ (3-1-22a)
(CH$_2$)$_7$CH$_3$ (3-1-23a)
OCH$_3$ (3-1-24a)
OCH$_2$CH$_3$ (3-1-25a)
CH(CH$_3$)$_2$ (3-1-26a)
C(CH$_3$)$_3$ (3-1-27a)
N(CH$_3$)$_2$ (3-1-28a)
F (3-1-29a)
Cl (3-1-30a)
Br (3-1-31a)

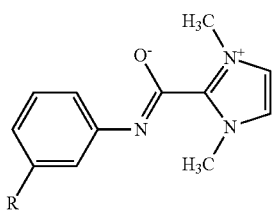

R = CH₃ (3-1-32a)
(CH₂)₃CH₃ (3-1-33a)
(CH₂)₇CH₃ (3-1-34a)
OCH₃ (3-1-35a)
OCH₂CH₃ (3-1-36a)
CH(CH₃)₂ (3-1-37a)
C(CH₃)₃ (3-1-38a)
N(CH₃)₂ (3-1-39a)
F (3-1-40a)
Cl (3-1-41a)
Br (3-1-42a)

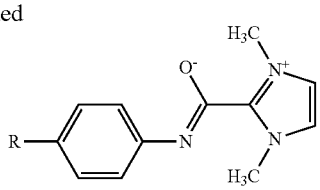

R = CH₃ (3-1-43a)
(CH₂)₃CH₃ (3-1-44a)
(CH₂)₇CH₃ (3-1-45a)
OCH₃ (3-1-46a)
OCH₂CH₃ (3-1-47a)
CH(CH₃)₂ (3-1-48a)
C(CH₃)₃ (3-1-49a)
N(CH₃)₂ (3-1-50a)
F (3-1-51a)
Cl (3-1-52a)
Br (3-1-53a)

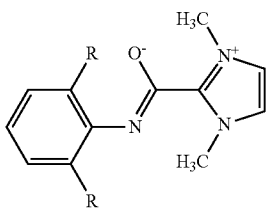

R = CH₃ (3-1-54a)
(CH₂)₃CH₃ (3-1-55a)
(CH₂)₇CH₃ (3-1-56a)
OCH₃ (3-1-58a)
OCH₂CH₃ (3-1-58a)
CH(CH₃)₂ (3-1-59a)
C(CH₃)₃ (3-1-60a)
N(CH₃)₂ (3-1-61a)
F (3-1-62a)
Cl (3-1-63a)
Br (3-1-64a)

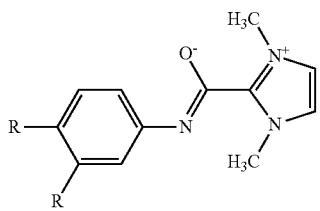

R = CH₃ (3-1-65a)
(CH₂)₃CH₃ (3-1-66a)
(CH₂)₇CH₃ (3-1-67a)
OCH₃ (3-1-68a)
OCH₂CH₃ (3-1-69a)
CH(CH₃)₂ (3-1-70a)
C(CH₃)₃ (3-1-71a)
N(CH₃)₂ (3-1-72a)
F (3-1-73a)
Cl (3-1-74a)
Br (3-1-75a)

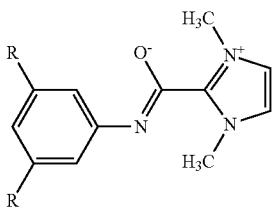

R = CH₃ (3-1-76a)
(CH₂)₃CH₃ (3-1-77a)
(CH₂)₇CH₃ (3-1-78a)
OCH₃ (3-1-79a)
OCH₂CH₃ (3-1-80a)
CH(CH₃)₂ (3-1-81a)
C(CH₃)₃ (3-1-82a)
N(CH₃)₂ (3-1-83a)
F (3-1-84a)
Cl (3-1-85a)
Br (3-1-86a)

(3-1-87a)

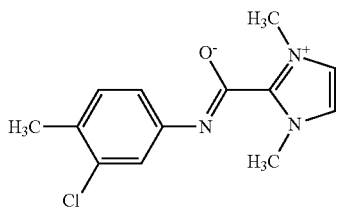

(3-1-88a)

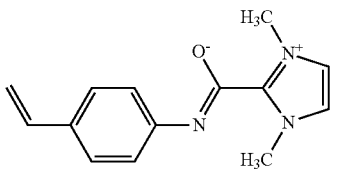

(3-1-89a)

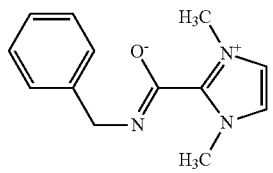

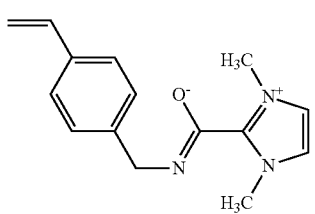 (3-1-90a)
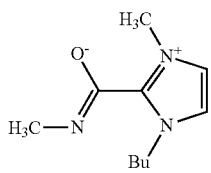 (3-1-1b)
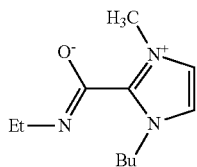 (3-1-2b)
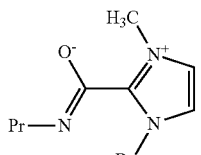 (3-1-3b)
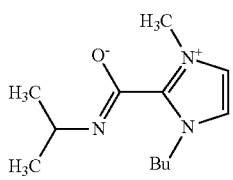 (3-1-4b)
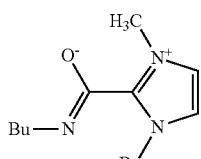 (3-1-5b)
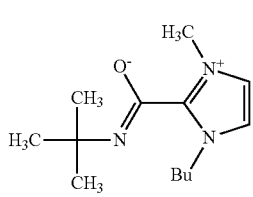 (3-1-6b)
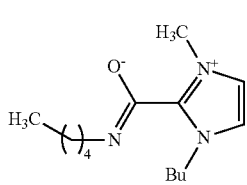 (3-1-7b)
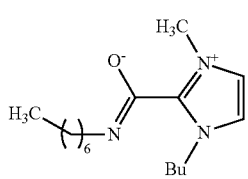 (3-1-8b)
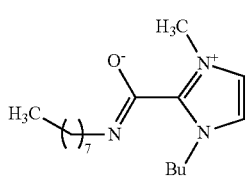 (3-1-9b)
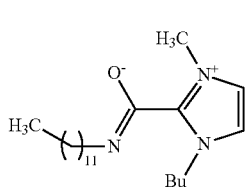 (3-1-10b)
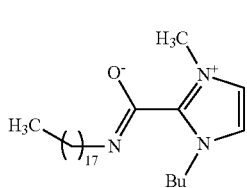 (3-1-11b)
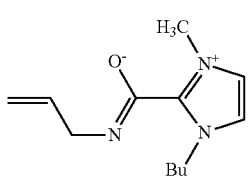 (3-1-12b)
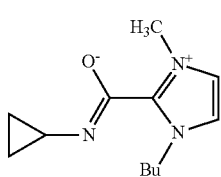 (3-1-13b)
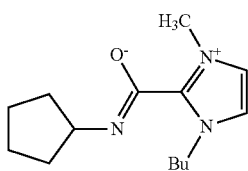 (3-1-14b)
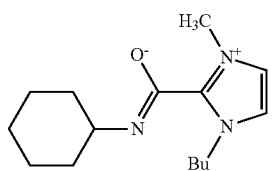 (3-1-15b)

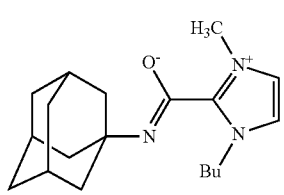
(3-1-16b)
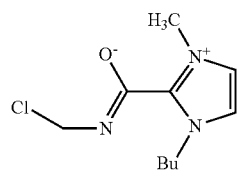
(3-1-17b)
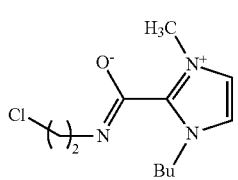
(3-1-18b)
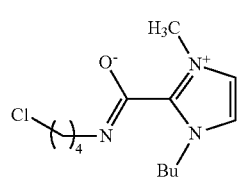
(3-1-19 b)
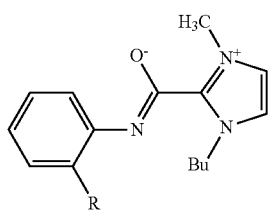
R = H (3-1-20b)
CH₃ (3-1-21b)
(CH₂)₃CH₃ (3-1-22b)
(CH₂)₇CH₃ (3-1-23b)
OCH₃ (3-1-24b)
OCH₂CH₃ (3-1-25b)
CH(CH₃)₂ (3-1-26b)
C(CH₃)₃ (3-1-27b)
N(CH₃)₂ (3-1-28b)
F (3-1-29b)
Cl (3-1-30b)
Br (3-1-31b)
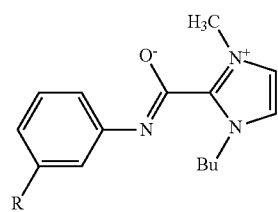
R = CH₃ (3-1-32b)
(CH₂)₃CH₃ (3-1-33b)
(CH₂)₇CH₃ (3-1-34b)
OCH₃ (3-1-35b)
OCH₂CH₃ (3-1-36b)
CH(CH₃)₂ (3-1-37b)
C(CH₃)₃ (3-1-38b)
N(CH₃)₂ (3-1-39b)
F (3-1-40b)
Cl (3-1-41b)
Br (3-1-42b)
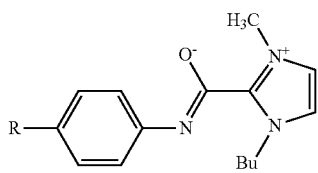
R = CH₃ (3-1-43b)
(CH₂)₃CH₃ (3-1-44b)
(CH₂)₇CH₃ (3-1-45b)
OCH₃ (3-1-46b)
OCH₂CH₃ (3-1-47b)
CH(CH₃)₂ (3-1-48b)
C(CH₃)₃ (3-1-49b)
N(CH₃)₂ (3-1-50b)
F (3-1-51b)
Cl (3-1-52b)
Br (3-1-53b)
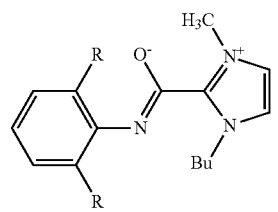
R = CH₃ (3-1-54b)
(CH₂)₃CH₃ (3-1-55b)
(CH₂)₇CH₃ (3-1-56b)
OCH₃ (3-1-57b)
OCH₂CH₃ (3-1-58b)
CH(CH₃)₂ (3-1-59b)
C(CH₃)₃ (3-1-60b)
N(CH₃)₂ (3-1-61b)
F (3-1-62b)
Cl (3-1-63b)
Br (3-1-64b)

-continued
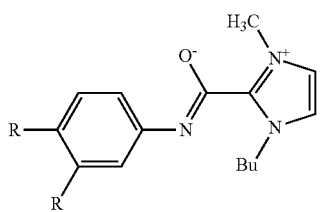
R = CH₃ (3-1-66b)
(CH₂)₃CH₃ (3-1-66b)
(CH₂)₇CH₃ (3-1-67b)
OCH₃ (3-1-68b)
OCH₂CH₃ (3-1-69b)
CH(CH₃)₂ (3-1-70b)
C(CH₃)₃ (3-1-71b)
N(CH₃)₂ (3-1-72b)
F (3-1-73b)
Cl (3-1-74b)
Br (3-1-75b)
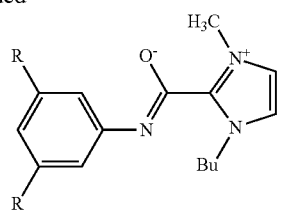
R = CH₃ (3-1-76b)
(CH₂)₃CH₃ (3-1-77b)
(CH₂)₇CH₃ (3-1-78b)
OCH₃ (3-1-79b)
OCH₂CH₃ (3-1-80b)
CH(CH₃)₂ (3-1-81b)
C(CH₃)₃ (3-1-82b)
N(CH₃)₂ (3-1-83b)
F (3-1-84b)
Cl (3-1-85b)
Br (3-1-86b)
(3-1-87b)
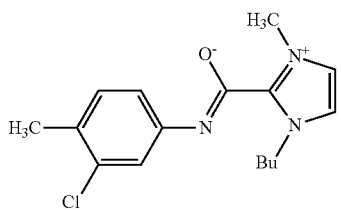
(3-1-88b)
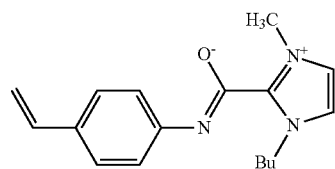
(3-1-89b)
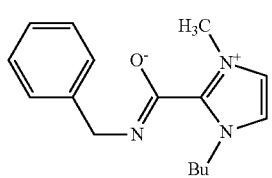
(3-1-90b)
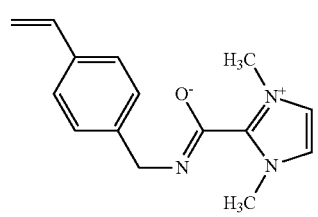
(3-1-1c)
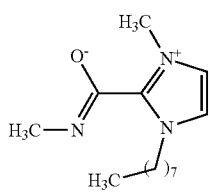
(3-1-2c)
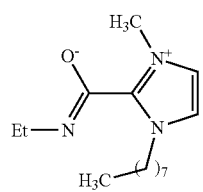
(3-1-3c)
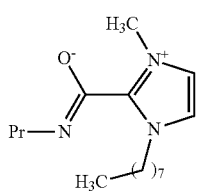
(3-1-4c)
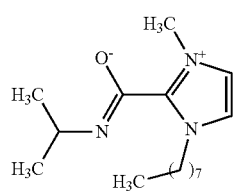
(3-1-5c)
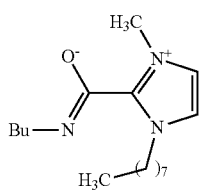
(3-1-6c)
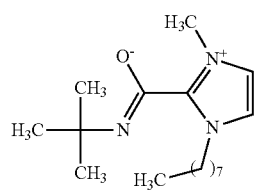

-continued
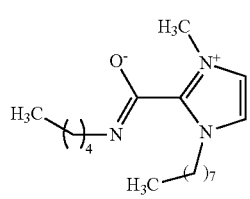 (3-1-7c)
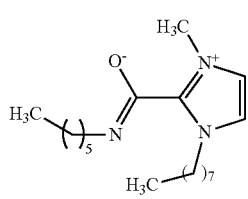 (3-1-8c)
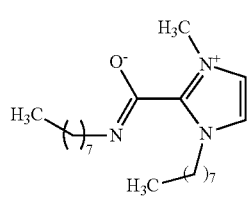 (3-1-9c)
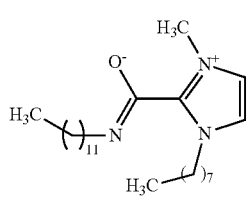 (3-1-10c)
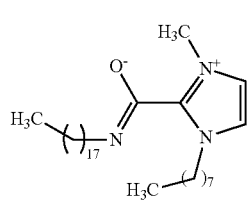 (3-1-11c)
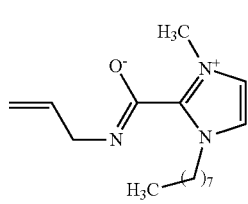 (3-1-12c)
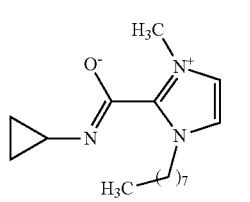 (3-1-13c)
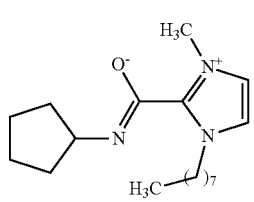 (3-1-14c)
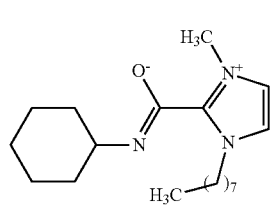 (3-1-15c)
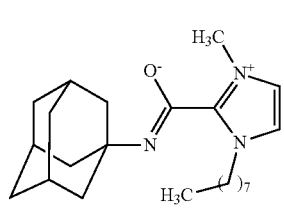 (3-1-16c)
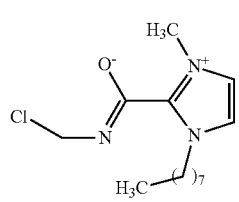 (3-1-17c)
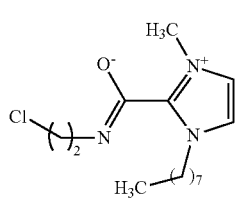 (3-1-158c)

-continued (3-1-19c)

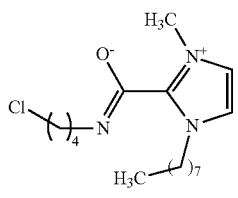

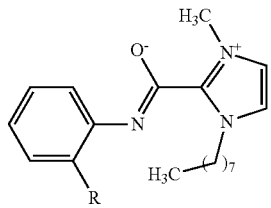

R = H (3-1-20c)
CH₃ (3-1-21c)
(CH₂)₃CH₃ (3-1-22c)
(CH₂)₇CH₃ (3-1-23c)
OCH₃ (3-1-24c)
OCH₂CH₃ (3-1-25c)
CH(CH₃)₂ (3-1-26c)
C(CH₃)₃ (3-1-27c)
N(CH₃)₂ (3-1-28c)
F (3-1-29c)
Cl (3-1-30c)
Br (3-1-31c)

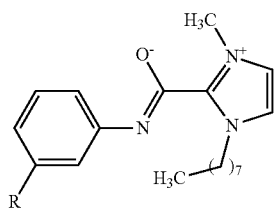

R = CH₃ (3-1-32c)
(CH₂)₃CH₃ (3-1-33c)
(CH₂)₇CH₃ (3-1-34c)
OCH₃ (3-1-35c)
OCH₂CH₃ (3-1-36c)
CH(CH₃)₂ (3-1-37c)
C(CH₃)₃ (3-1-38c)
N(CH₃)₂ (3-1-39c)
F (3-1-40c)
Cl (3-1-41c)
Br (3-1-42c)

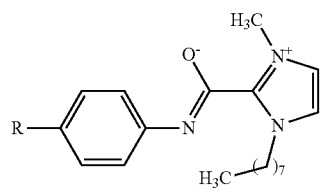

R = CH₃ (3-1-43c)
(CH₂)₃CH₃ (3-1-44c)
(CH₂)₇CH₃ (3-1-45c)
OCH₃ (3-1-46c)
OCH₂CH₃ (3-1-47c)
CH(CH₃)₂ (3-1-48c)
C(CH₃)₃ (3-1-49c)
N(CH₃)₂ (3-1-50c)
F (3-1-51c)
Cl (3-1-52c)
Br (3-1-53c)

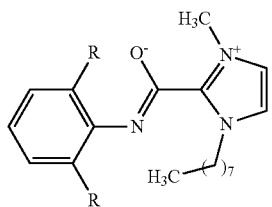

R = CH₃ (3-1-54c)
(CH₂)₃CH₃ (3-1-55c)
(CH₂)₇CH₃ (3-1-56c)
OCH₃ (3-1-58c)
OCH₂CH₃ (3-1-58c)
CH(CH₃)₂ (3-1-59c)
C(CH₃)₃ (3-1-60c)
N(CH₃)₂ (3-1-61c)
F (3-1-62c)
Cl (3-1-63c)
Br (3-1-64c)

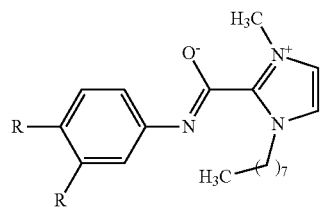

R = CH₃ (3-1-65c)
(CH₂)₃CH₃ (3-1-66c)
(CH₂)₇CH₃ (3-1-67c)
OCH₃ (3-1-68c)
OCH₂CH₃ (3-1-69c)
CH(CH₃)₂ (3-1-70c)
C(CH₃)₃ (3-1-71c)
N(CH₃)₂ (3-1-72c)
F (3-1-73c)
Cl (3-1-74c)
Br (3-1-75c)

-continued
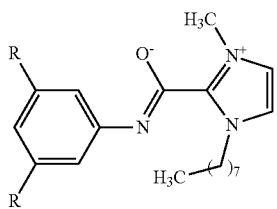 (3-1-87c)
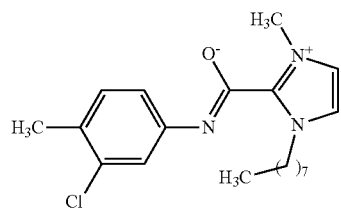
R = CH₃ (3-1-76c)
(CH₂)₃CH₃ (3-1-77c)
(CH₂)₇CH₃ (3-1-78c)
OCH₃ (3-1-79c)
OCH₂CH₃ (3-1-80c)
CH(CH₃)₂ (3-1-81c)
C(CH₃)₃ (3-1-82c)
N(CH₃)₂ (3-1-83cc)
F (3-1-84c)
Cl (3-1-85c)
Br (3-1-86c)
(3-1-88c) 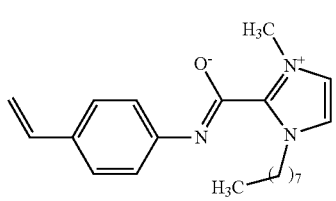
(3-1-89c) 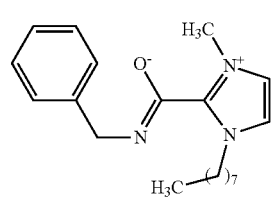
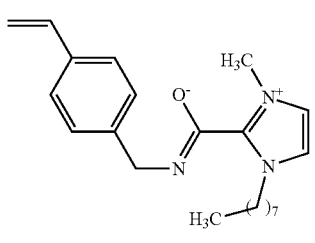 (3-1-90c)
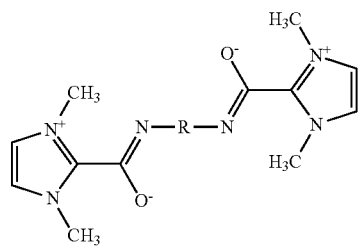
R = —CH₂— (3-2-1a)
—CH₂CH₂— (3-2-2a)
—CH₂(CH₂)₂CH₂— (3-2-3a)
—CH₂(CH₂)₃CH₂— (3-2-4a)
—CH₂(CH₂)₆CH₂— (3-2-5a)
—CH₂(CH₂)₈CH₂— (3-2-6a)
—CH₂(CH₂)₁₀CH₂— (3-2-7a)
(3-2-8a) 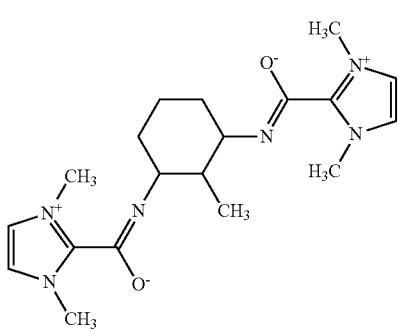
(3-2-9a) 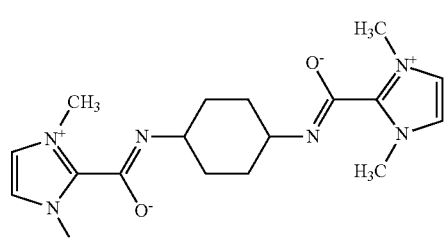

-continued
(3-2-10a)
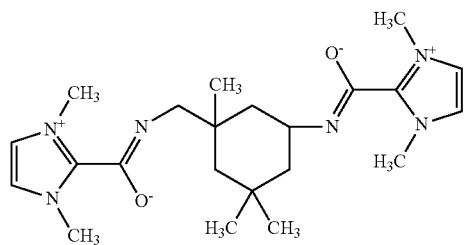
(3-2-11a)
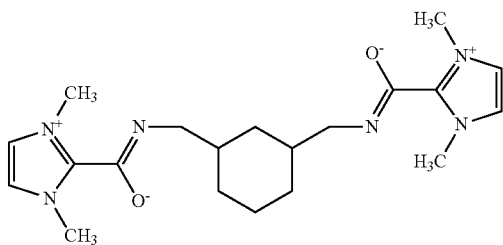
(3-2-12a)
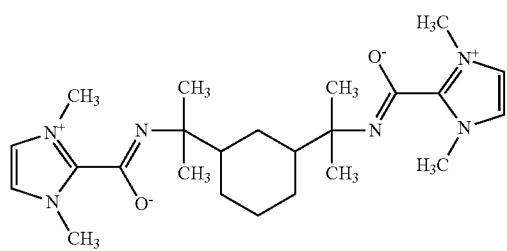
(3-2-13a)
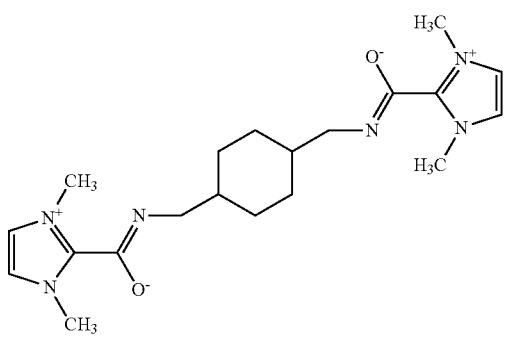
(3-2-14a)
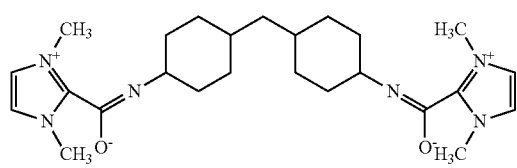
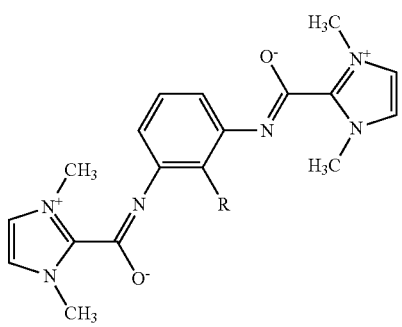
R = H (3-2-15a)
CH$_3$ (3-2-16a)
(3-2-17a)
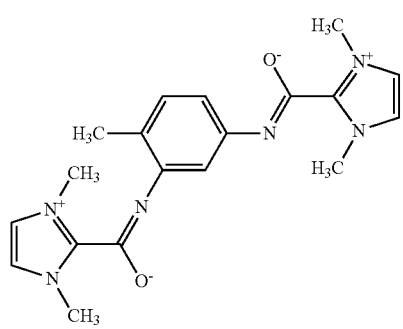
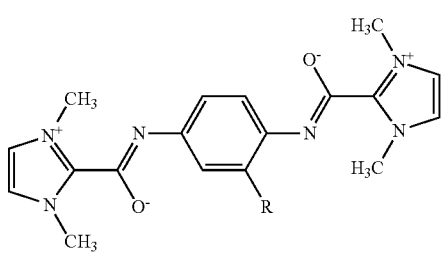
R = H (3-2-18a)
CH$_3$ (3-2-19a)
(3-2-20a)
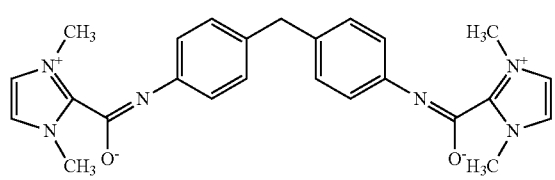
(3-2-21a)
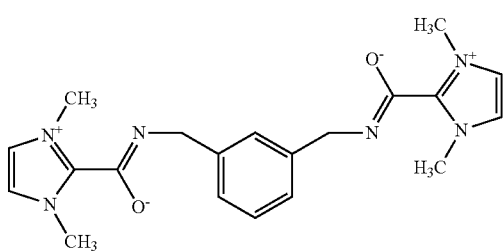

(3-2-22a)
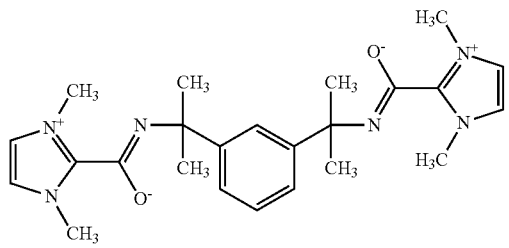
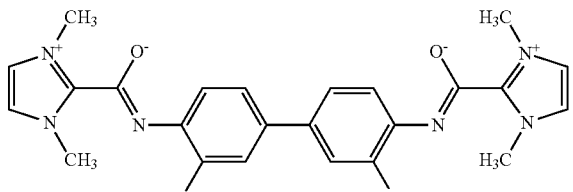
R = CH₃ (3-2-23a)
CH₂CH₃ (3-2-24a)
OCH₃ (3-2-25a)
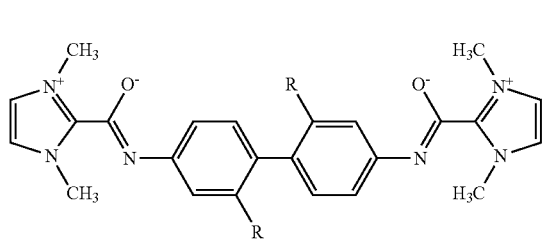
R = CH₃ (3-2-26a)
CF₃ (3-2-27a)
(3-2-28a)
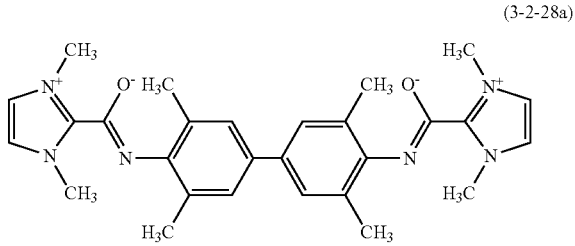
(3-2-29a)
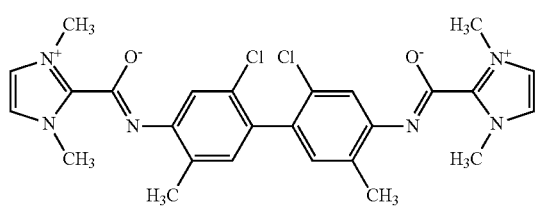
(3-2-30a)
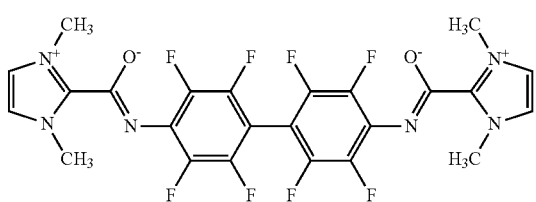
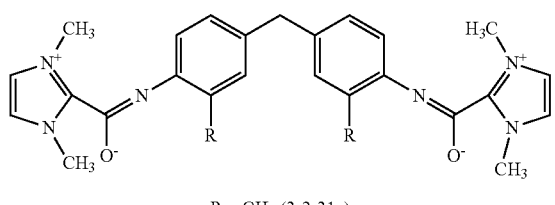
R = CH₃ (3-2-31a)
Cl (3-2-32a)
(3-2-33a)
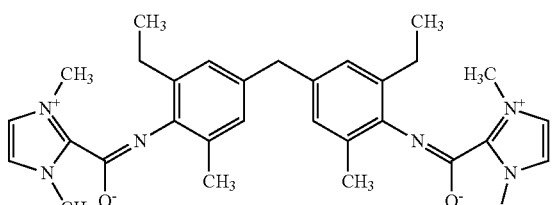
(3-2-34a)
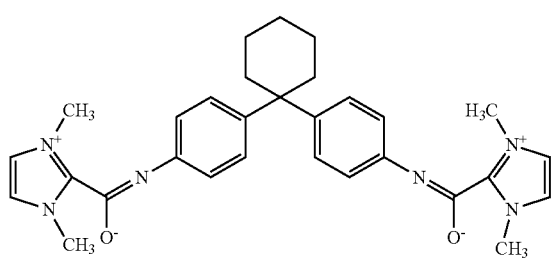
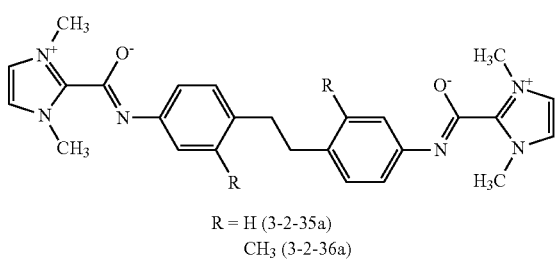
R = H (3-2-35a)
CH₃ (3-2-36a)

(3-2-37a)
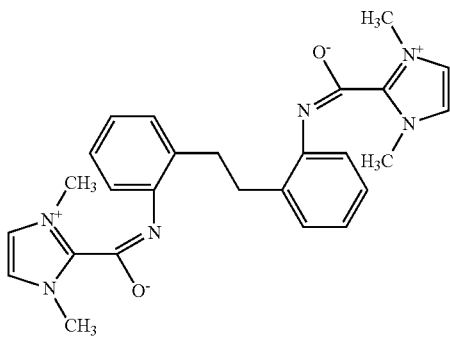
(1-2-39a)
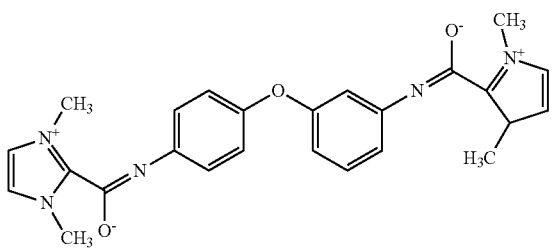
(1-2-41a)
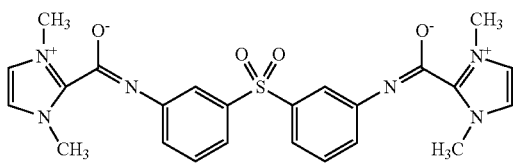
(1-2-43a)
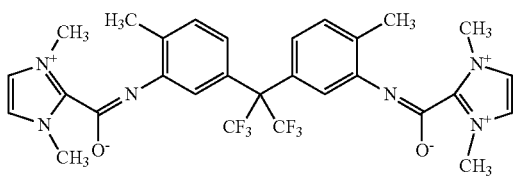
(3-2-38a)
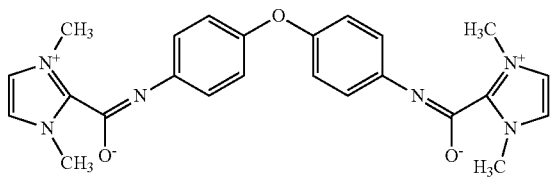
(1-2-40a)
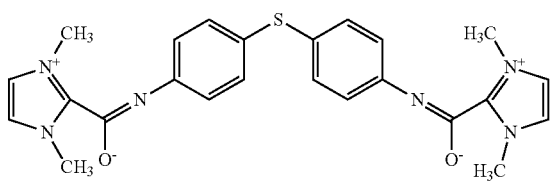
(1-2-42a)
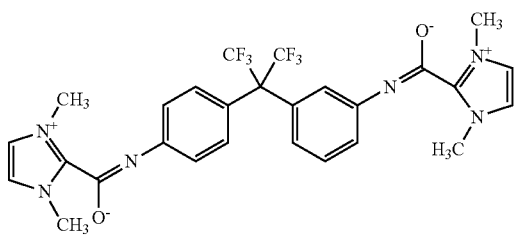
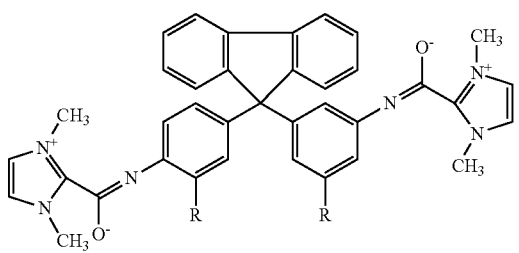
R = H (1-2-44a)
CH₃ (1-2-45a)
F (1-2-46a)
Cl (1-2-47a)
(3-2-48a)
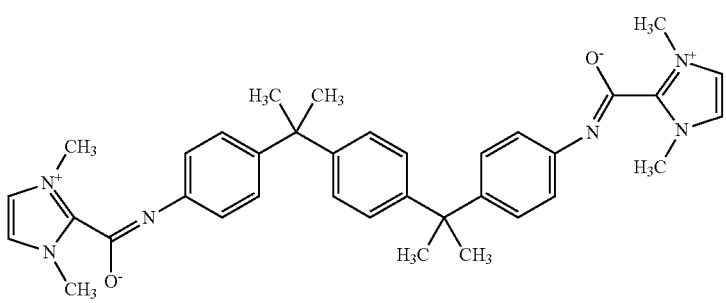

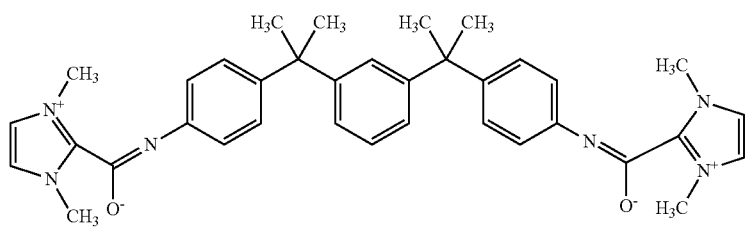
(3-2-49a)
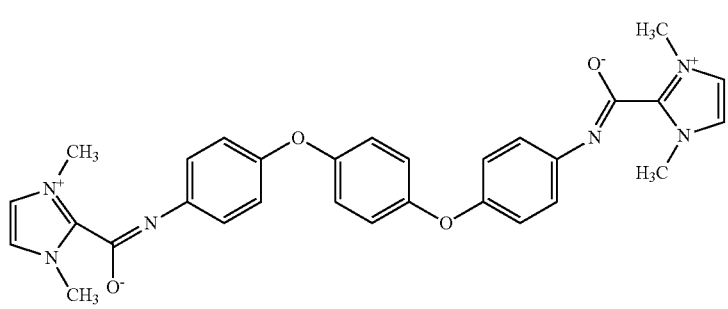
(3-2-50a)
(3-2-51a)
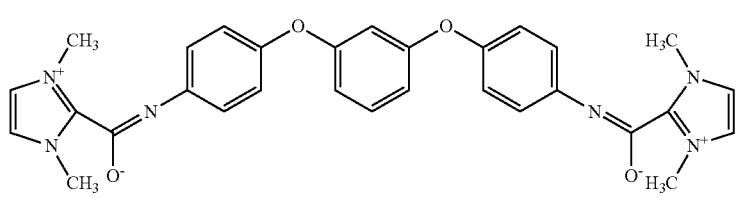
(3-2-52a)
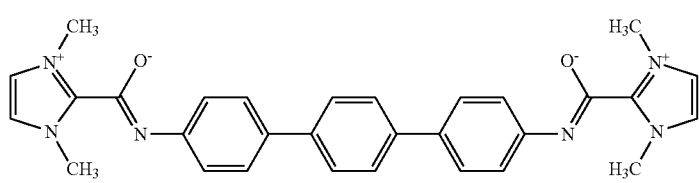
(3-2-53a)
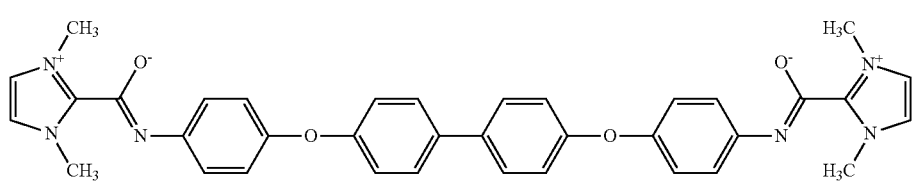
(3-2-54a)
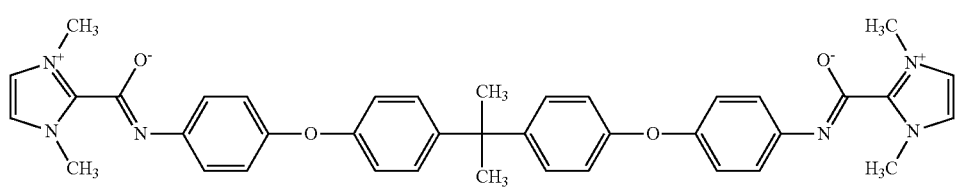
(3-2-55a)
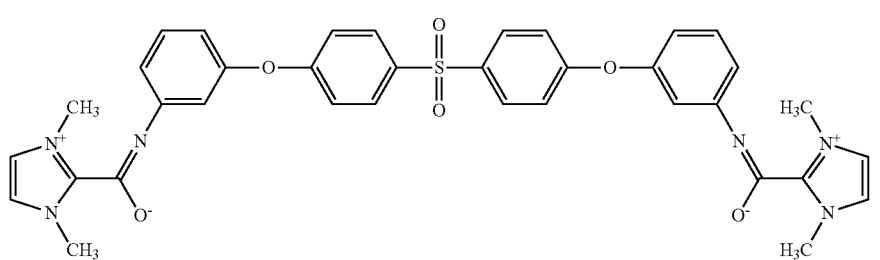

-continued
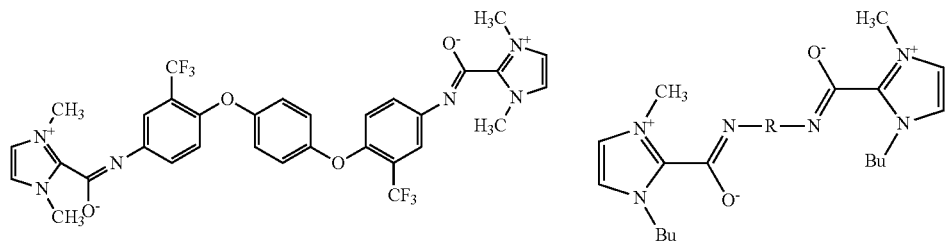
(3-2-56a)
(3-2-1b) R = —CH₂—
—CH₂CH₂— (3-2-2b)
—CH₂(CH₂)₂CH₂— (3-2-3b)
—CH₂(CH₂)₄CH₂— (3-2-4b)
—CH₂(CH₂)₆CH₂— (3-2-5b)
—CH₂(CH₂)₈CH₂— (3-2-6b)
—CH₂(CH₂)₁₀CH₂— (3-2-7b)
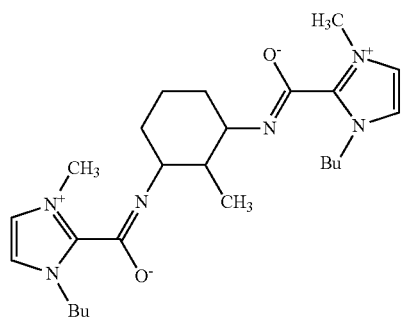
(3-2-8b)
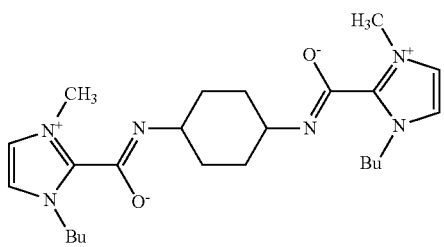
(3-2-9b)
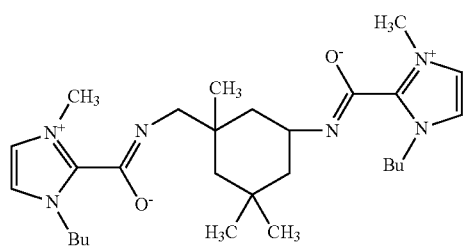
(3-2-10b)
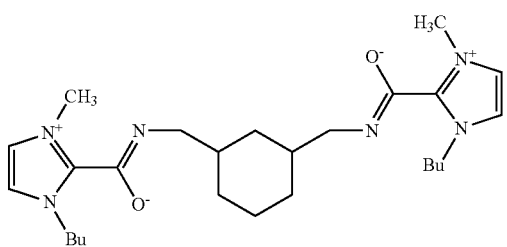
(3-2-11b)
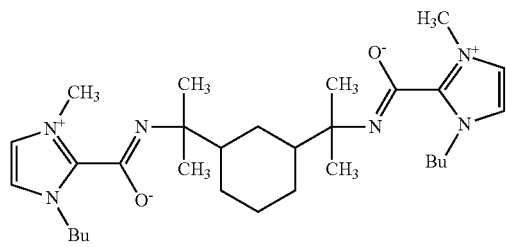
(3-2-12b)
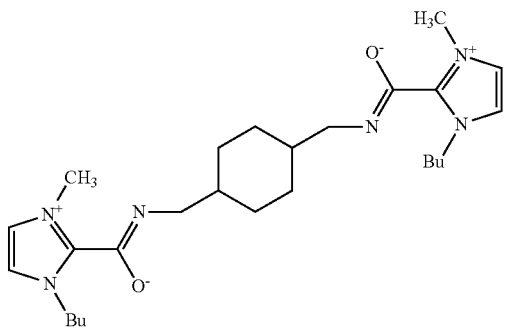
(3-2-13b)

-continued
(3-2-14b)
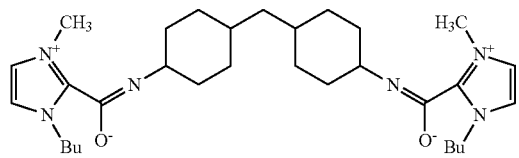
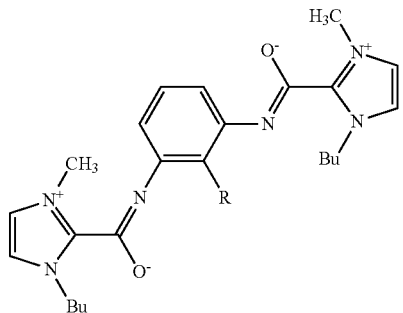
R = H (3-2-15b)
CH₃ (3-2-16b)
(3-2-17b)
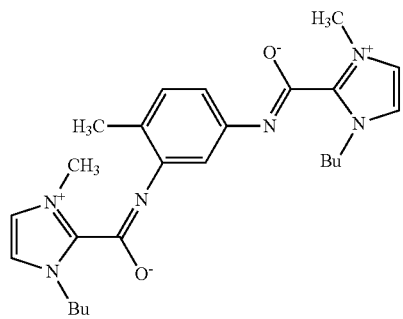
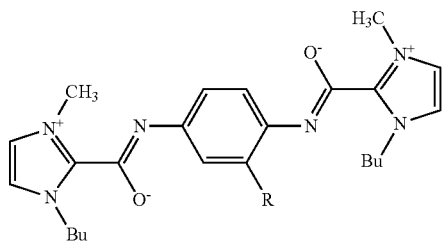
R = H (3-2-18b)
CH₃ (3-2-19b)
(3-2-20b)
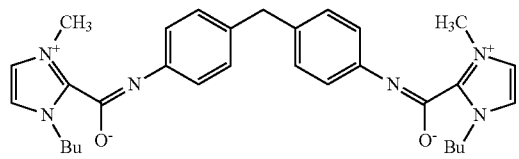
(3-2-21b)
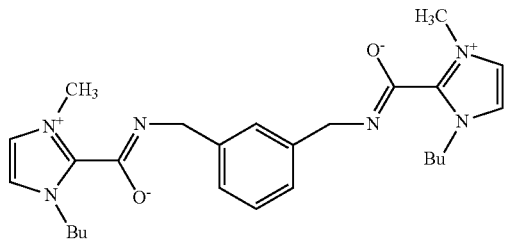
(3-2-22b)
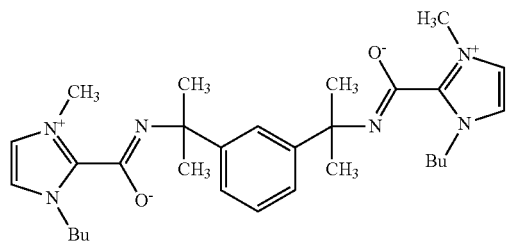
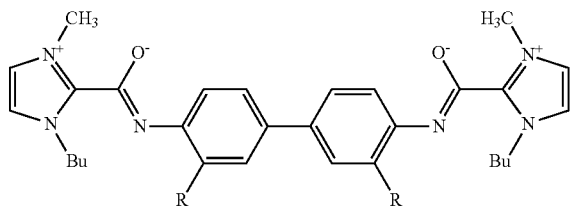
R = CH₃ (3-2-23b)
CH₂CH₃ (3-2-24b)
OCH₃ (3-2-25b)
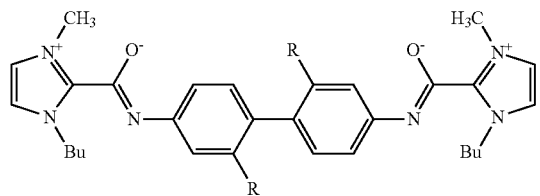
R = CH₃ (3-2-26b)
CF₃ (3-2-27b)
(3-2-28b)
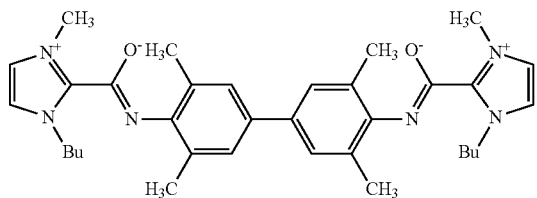

-continued
(3-2-29b)
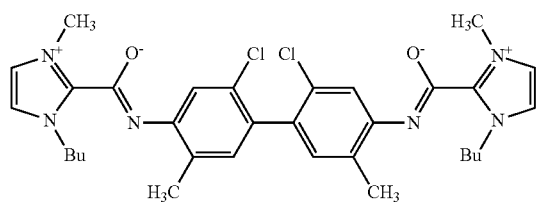
(3-2-30b)
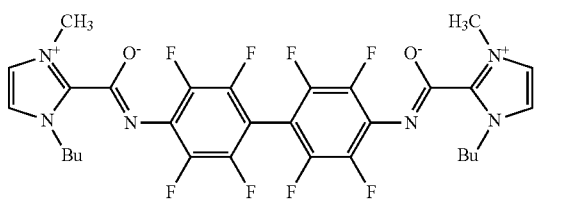
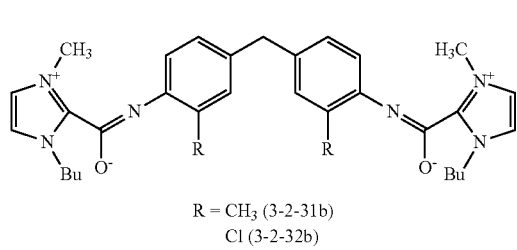
R = CH₃ (3-2-31b)
Cl (3-2-32b)
(3-2-33b)
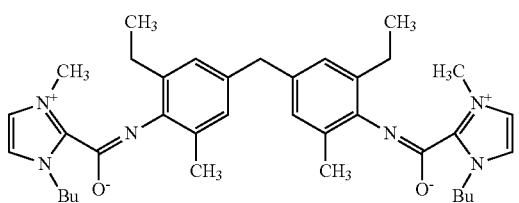
(3-2-34b)
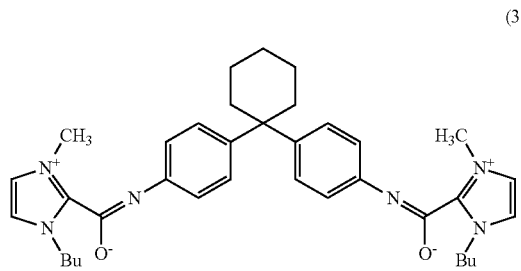
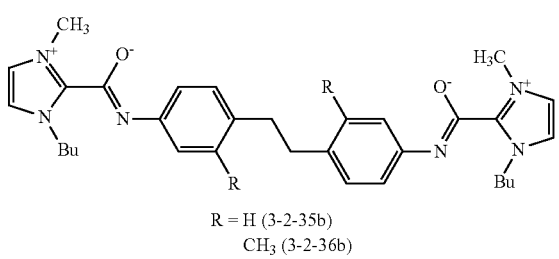
R = H (3-2-35b)
CH₃ (3-2-36b)
(3-2-37b)
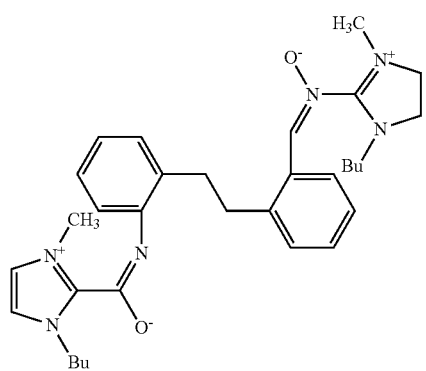
(3-2-38b)
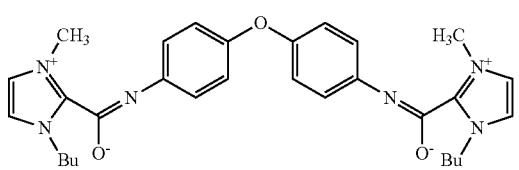
(3-2-39b)
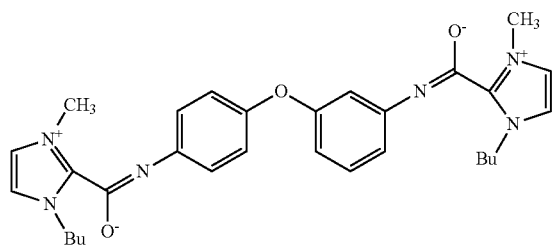
(3-2-40b)
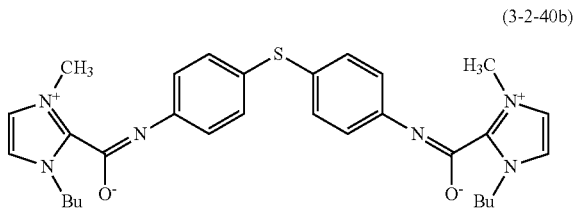

-continued
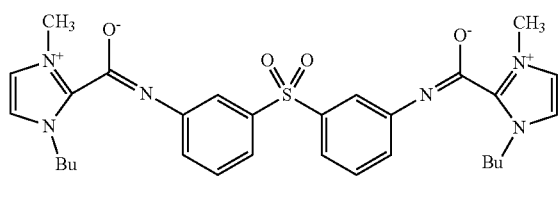
(3-2-41b)
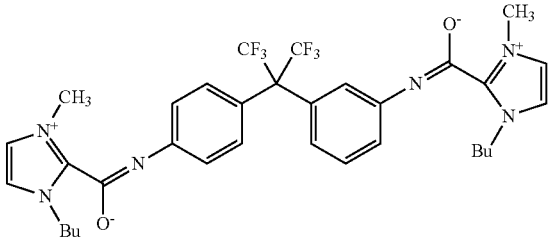
(3-2-42b)
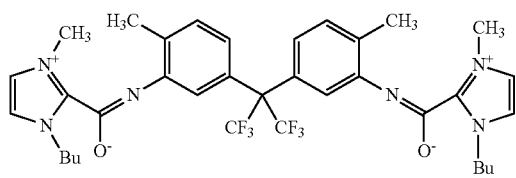
(3-2-43b)
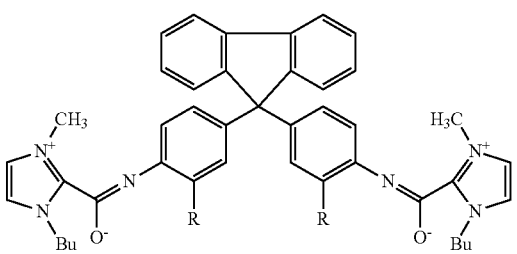
R = H (3-2-44b)
CH₃ (3-2-45b)
F (3-2-46b)
Cl (3-2-47b)
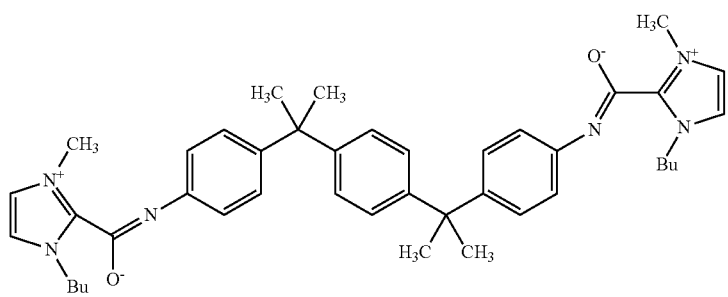
(3-2-48b)
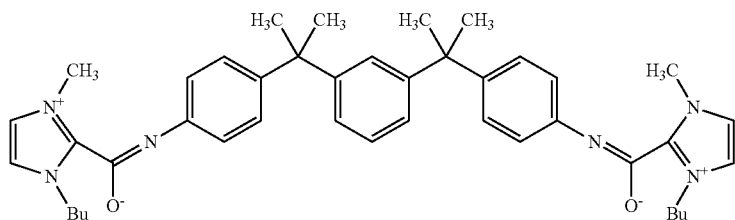
(3-2-49b)
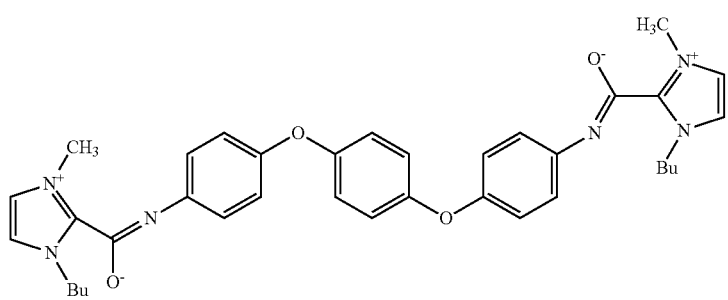
(3-2-50b)

-continued
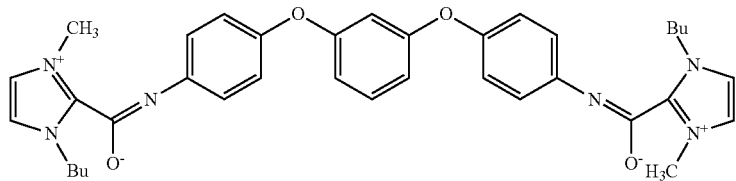
(3-2-51b)
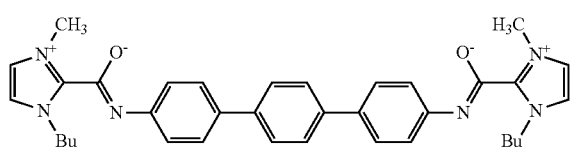
(3-2-52b)
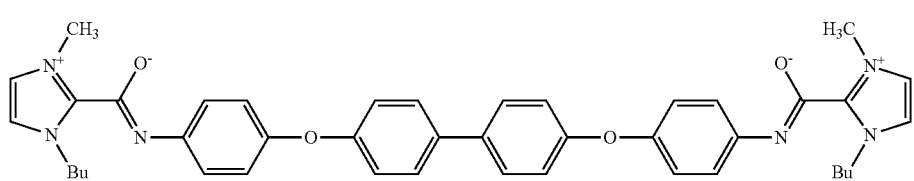
(3-2-53b)
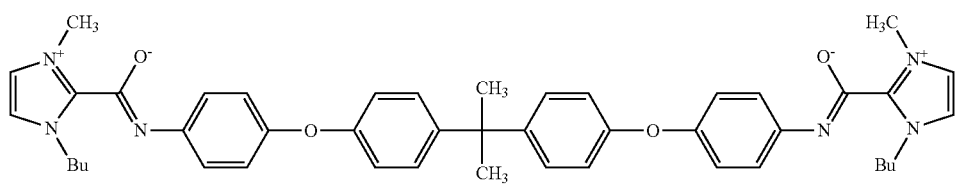
(3-2-54b)
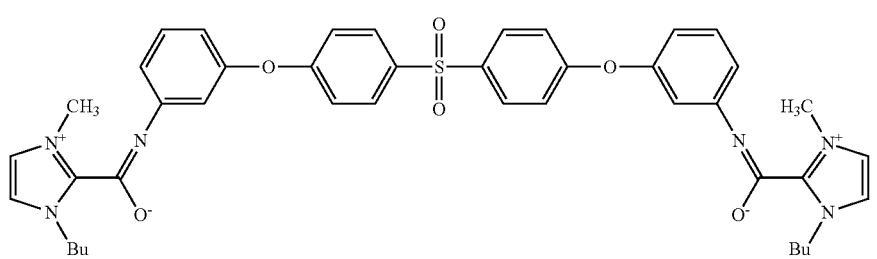
(3-2-55b)
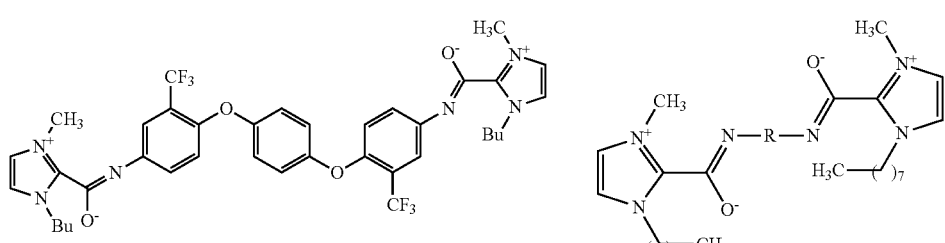
(3-2-56b)
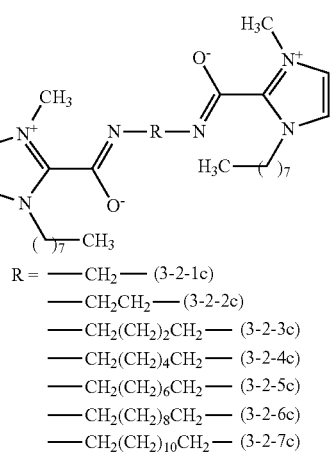
R = —CH₂— (3-2-1c)
—CH₂CH₂— (3-2-2c)
—CH₂(CH₂)₂CH₂— (3-2-3c)
—CH₂(CH₂)₄CH₂— (3-2-4c)
—CH₂(CH₂)₆CH₂— (3-2-5c)
—CH₂(CH₂)₈CH₂— (3-2-6c)
—CH₂(CH₂)₁₀CH₂— (3-2-7c)

-continued
(3-2-8c)
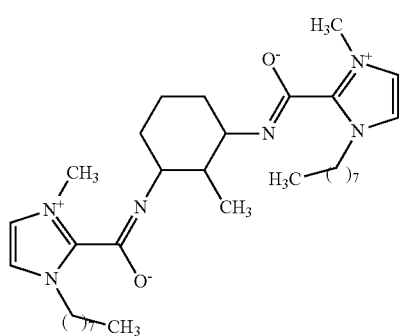
(3-2-9c)
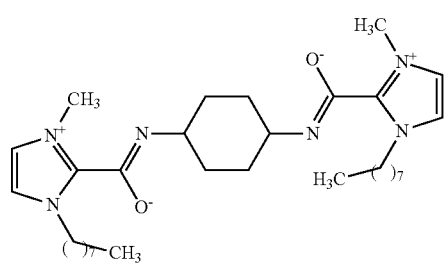
(3-2-10c)
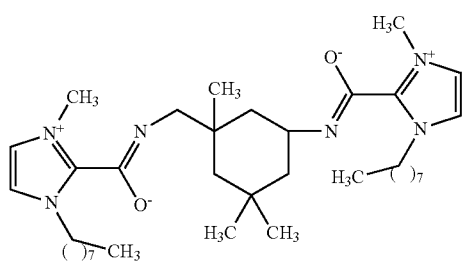
(3-2-11c)
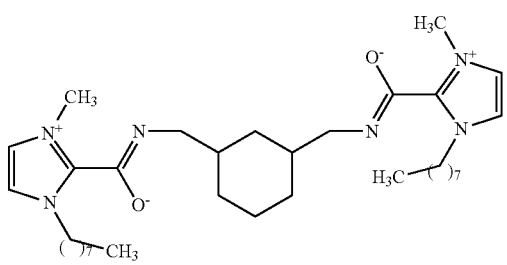
(3-2-12c)
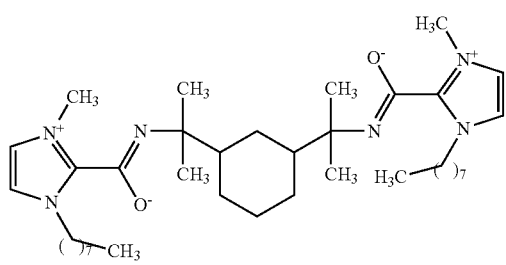
(3-2-13c)
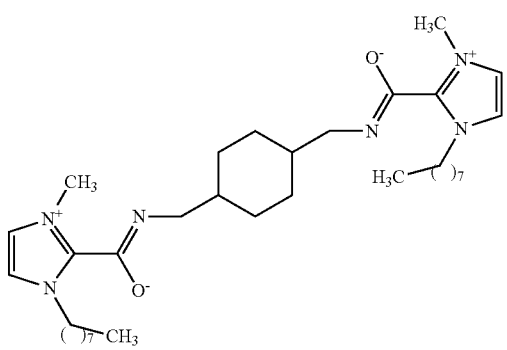
(3-2-14c)
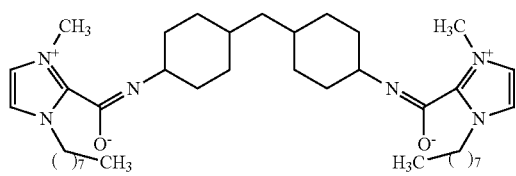
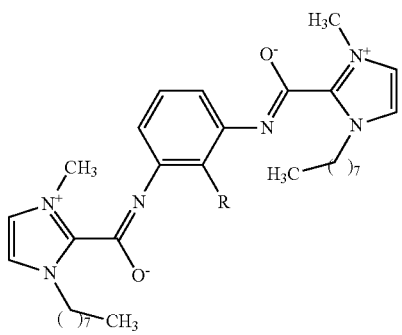
R = H (3-2-15c)
CH$_3$ (3-2-16c)

-continued
(3-2-17c)
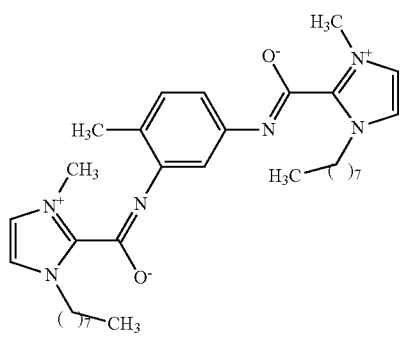
(3-2-18c)(3-2-19c)
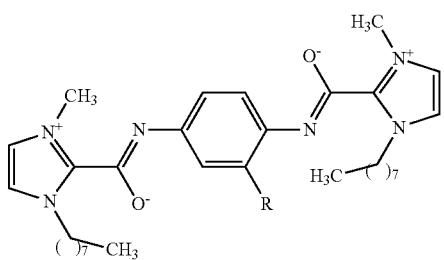
R = H (3-2-18c)
CH₃ (3-2-19c)
(3-2-20c)
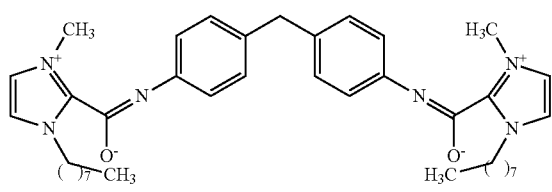
(3-2-21c)
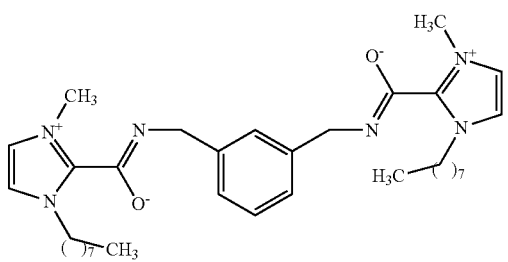
(3-2-22c)
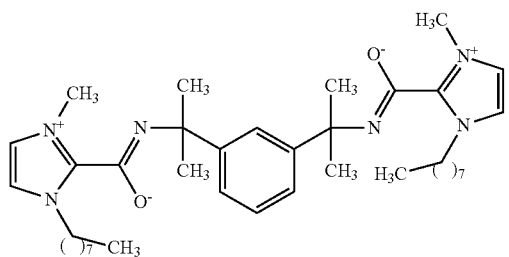
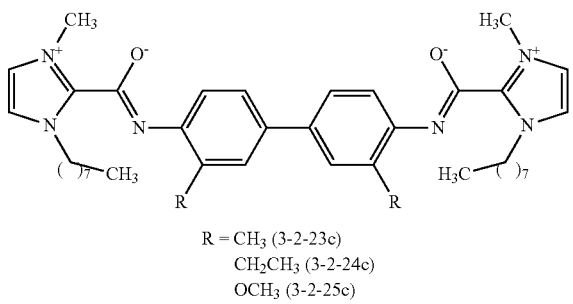
R = CH₃ (3-2-23c)
CH₂CH₃ (3-2-24c)
OCH₃ (3-2-25c)
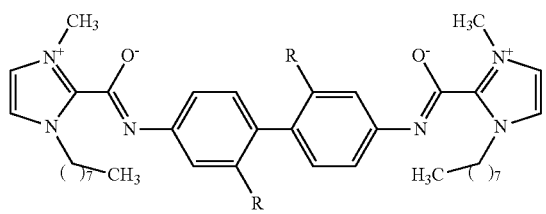
R = CH₃ (3-2-26c)
CF₃ (3-2-27c)
(3-2-28c)
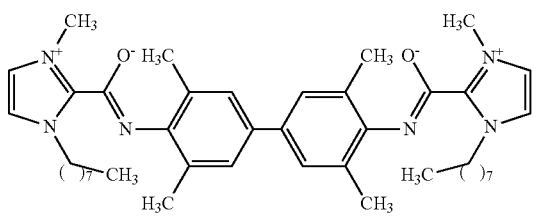
(3-2-29c)
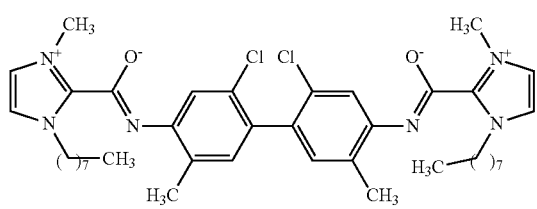
(3-2-30c)
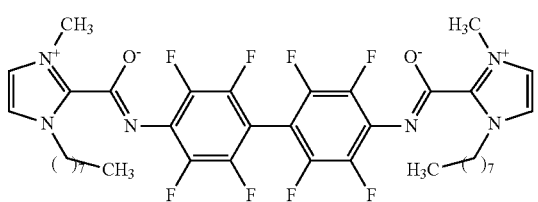

-continued
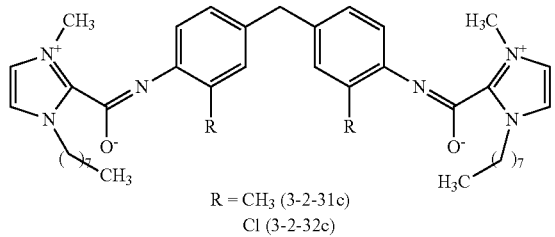
(3-2-33c)
R = CH3 (3-2-31c)
Cl (3-2-32c)
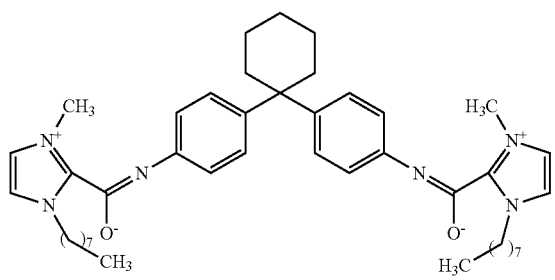
(3-2-34c)
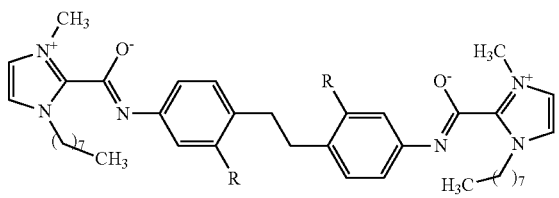
R = H (3-2-35c)
CH3 (3-2-36c)
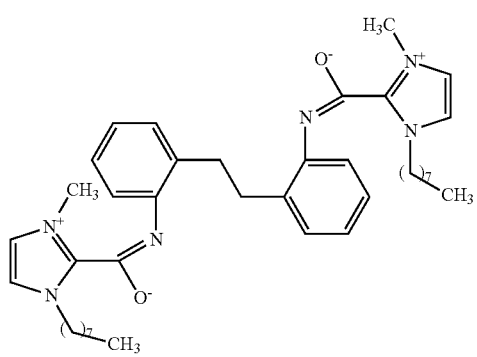
(3-2-37c)
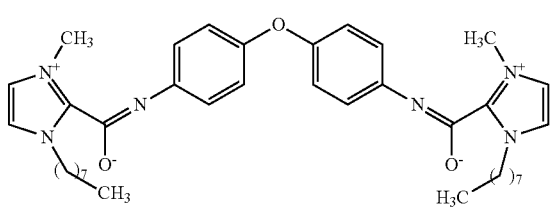
(3-2-38c)
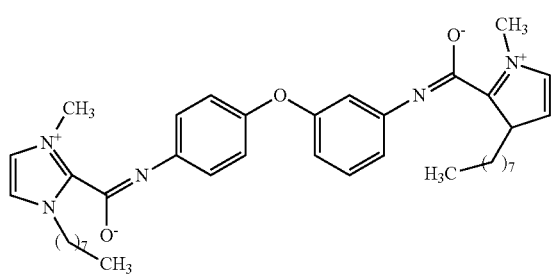
(3-2-39c)
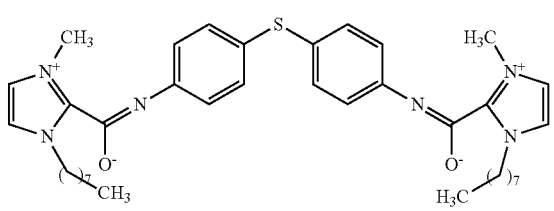
(3-2-40c)
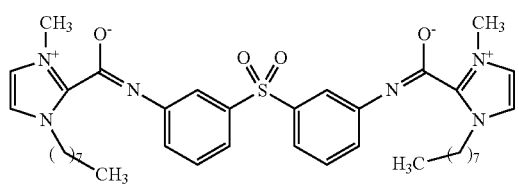
(3-2-41c)
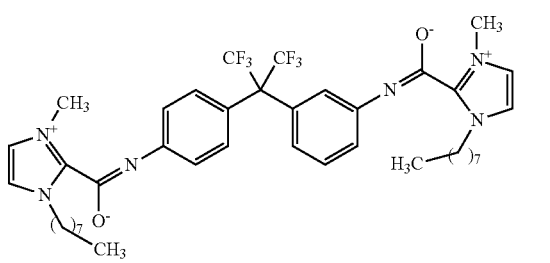
(3-2-42c)

-continued
(3-2-43c)
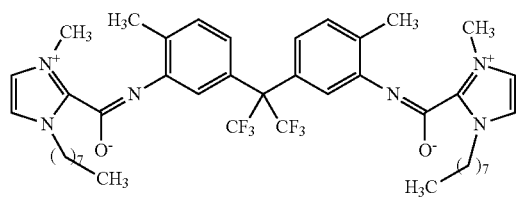
(3-2-44c)
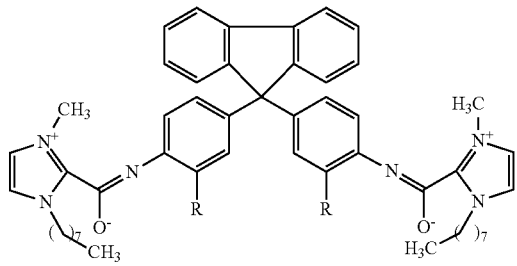
R = H (3-2-44c)
CH₃ (3-2-45c)
F (3-2-46c)
Cl (3-2-47c)
(3-2-48c)
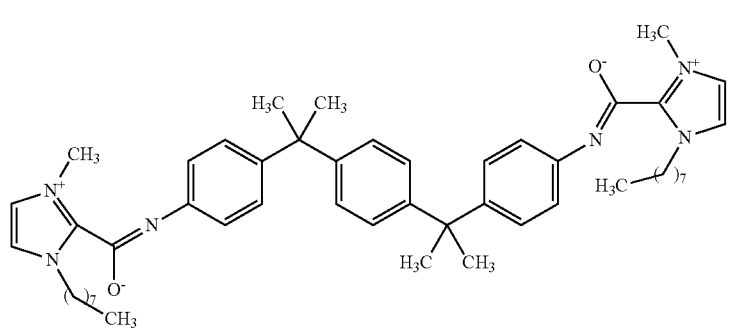
(3-2-49c)
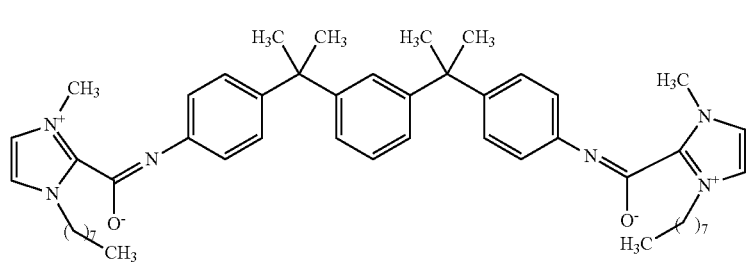
(3-2-50c)
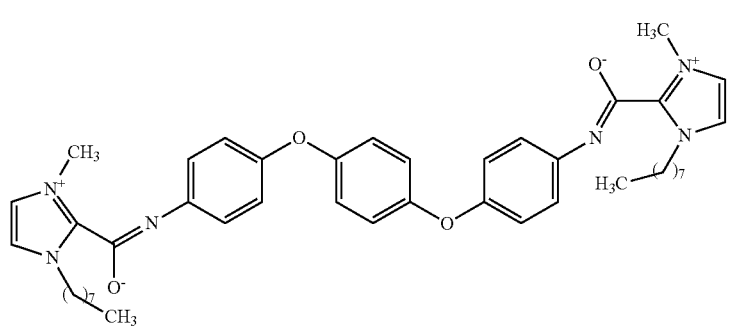
(3-2-51c)
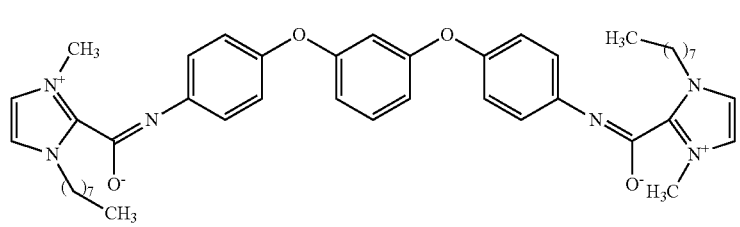

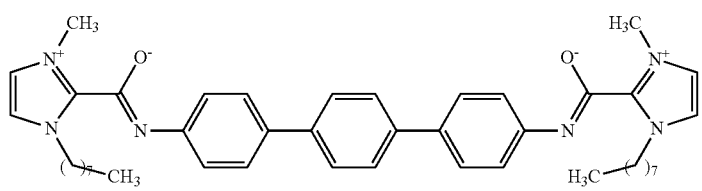
(3-2-52c)
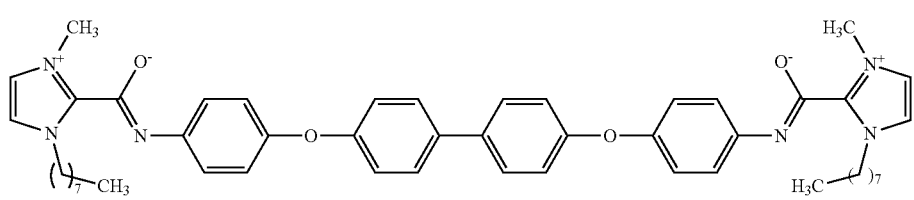
(3-2-53c)
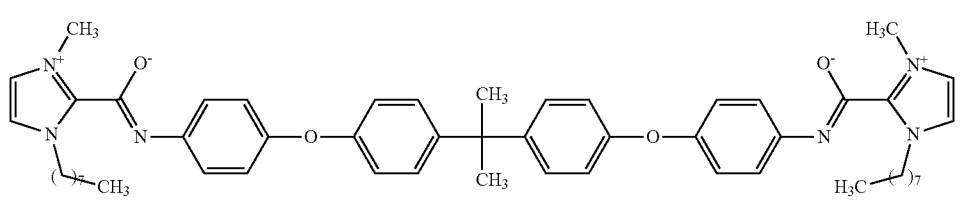
(3-2-54c)
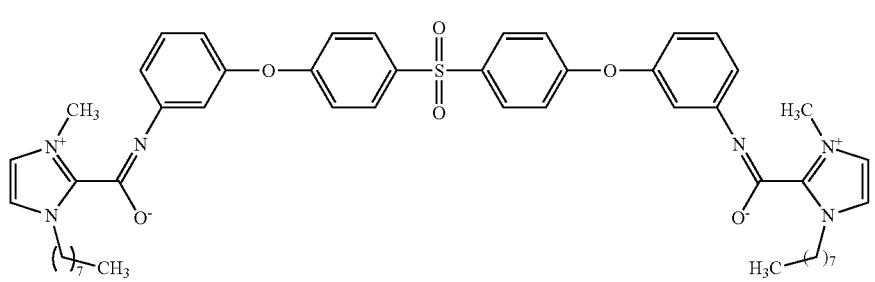
(3-2-55c)
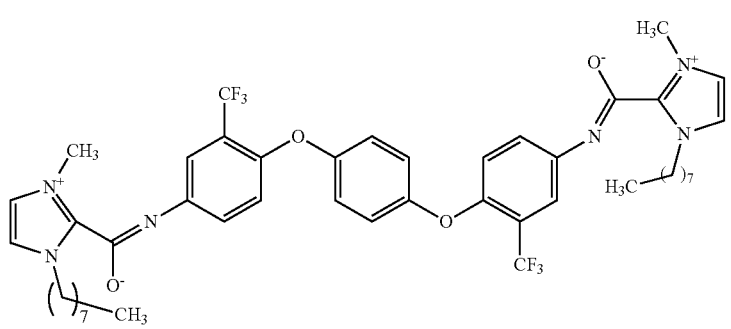
(3-2-56c)
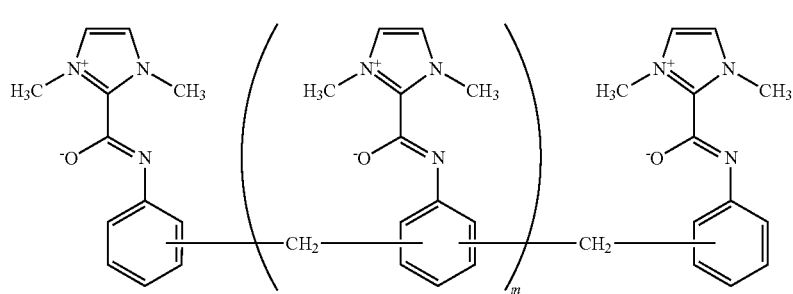
(3-3-1a)

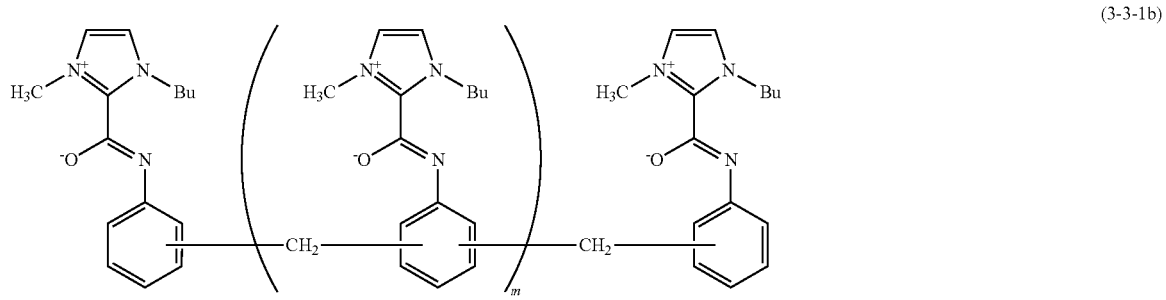

(3-3-1b)

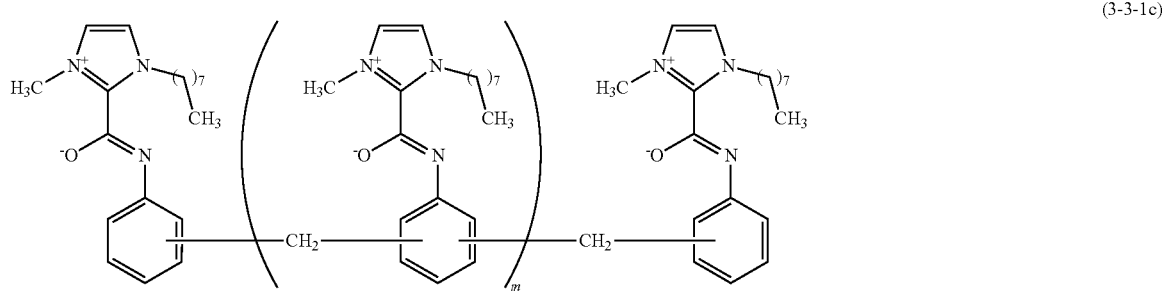

(3-3-1c)

(In Formula (3-3-1a), Formula (3-3-1b), and Formula (3-3-1c), m is as defined above.)

Preferable examples of the amidate compound (3) include compounds represented by Formulas (3-1-30a), (3-1-41a), (3-1-45a), (3-1-46a), (3-1-48a), (3-1-52a), (3-1-59a), (3-1-88a), (3-1-89a), (3-1-90a), (3-2-20a), (3-1-30b), (3-1-41b), (3-1-45b), (3-1-46b), (3-1-48b), (3-1-52b), (3-1-59b), (3-1-88b), (3-1-89b), (3-1-90b), (3-2-20b), (3-1-30c), (3-1-41c), (3-1-45c), (3-1-46c), (3-1-48c), (3-1-52c), (3-1-59c), (3-1-88c), (3-1-89c), (3-1-90c), (3-2-20a), (3-2-38a), (3-2-41a), (3-2-48a), (3-2-49a), (3-2-51a), (3-2-54a), (3-2-20b), (3-2-38b), (3-2-41b), (3-2-48b), (3-2-49b), (3-2-51b), (3-2-54b), (3-2-20c), (3-2-38c), (3-2-41c), (3-2-48c), (3-2-49c), (3-2-51c), and (3-2-54c). Particularly preferable are compounds represented by Formulas (3-1-30a), (3-1-41a), (3-1-45a), (3-1-46a), (3-1-48a), (3-1-52a), (3-1-59a), (3-1-88a), (3-1-89a), (3-1-90a), (3-2-20a), (3-2-41a), (3-2-48a), (3-2-49a), (3-2-51a), (3-2-54a), (3-2-20c), (3-2-48c), (3-2-49c), and (3-2-20c).

When the amidate compound (3) of the present invention can exist as an isomer, such as an enantiomer, a stereoisomer, or a regioisomer, the amidate compound (3) includes a mixture of any isomers, unless the type of isomer is specified. For example, when the amidate compound (3) can exist as an enantiomer, the amidate compound (3) also includes enantiomers separated from a racemic mixture. These isomers can be obtained as single compounds by conventionally known synthesis methods and separation methods (concentration, solvent extraction, column chromatography, recrystallization, etc.).

The amidate compound (3) is considered to be isomerized by resonance. For example, the compound represented by Formula (3) wherein X is a nitrogen atom is considered to have the following resonance structure:

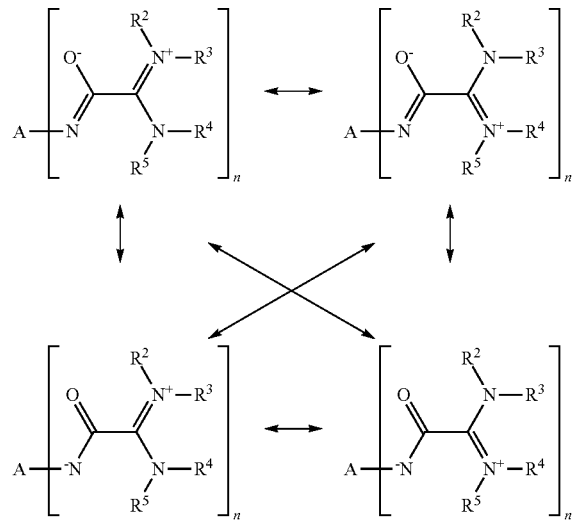

(wherein A, $R^2$, $R^3$, $R^4$, $R^5$, and n are as defined above).

In the reaction between the urethane compound (1) and the carboxylate compound (2), the carboxylate compound (2) is usually reacted with the carboxylate compound (1) in an amount of 0.8 moles or more, preferably 1 to 3 moles, per mole of carbamate groups contained in the urethane compound (1).

The reaction temperature is not particularly limited. Any temperature not exceeding the boiling point of the solvent can be used. The temperature is generally 10° C. or more, preferably 40 to 200° C., and particularly preferably 80 to 150° C.

A solvent may or may not be used in the reaction between the urethane compound (1) and the carboxylate compound (2). Examples of usable solvents include aromatic hydrocarbon solvents, such as toluene, benzene, and xylene; aliphatic hydrocarbon solvents, such as methylcyclohexane, cyclohexane, n-hexane, n-heptane, and octane; halogenated hydrocarbon solvents, such as butyl chloride and 1,2-dichloroethane; halogenated aromatic hydrocarbon solvents, such as chlorobenzene; and the like. Aromatic hydrocarbon solvents and halogenated aromatic hydrocarbon solvents are preferable, and toluene, xylene, and chlorobenzene are particularly preferable. These solvents can be used as a mixture of two or more, if necessary.

When a reaction mixture obtained by reacting the nitrogen-containing organic compound (8) with the dialkyl carbonate compound (9) is used as the carboxylate compound (2), the solvent in the reaction mixture can be directly used as a solvent for the reaction of the urethane compound (1) and the carboxylate compound (2). In this case, the reaction may be performed while adding a solvent, if necessary.

The amount of solvent used is generally 50 parts by weight or less, 0.1 parts by weight or more and 35 parts by weight or less, and more preferably 0.1 to 35 parts by weight, per part by weight of the carboxylate compound (2)

In the reaction of the urethane compound (1) and the carboxylate compound (2), If necessary, the reaction may be performed in an inert gas atmosphere that does not affect the reaction, such as nitrogen, argon, or helium.

After completion of the reaction, the amidate compound (3) can be obtained by removing the solvent by concentration or filtration of the reaction mixture. The obtained amidate compound (3) may be purified by a method, such as recrystallization.

EXAMPLES

The present invention is described in detail below based on Examples; however, the present invention is not limited thereto. In the Examples, a Bruker AV400 was used for $^1$H-NMR measurement, which was performed at 400 MHz.

Production Example 1-1: Synthesis of
1,3-dimethylimidazolium-2-carboxylate

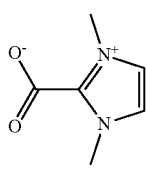

82.1 g (1.0 mol) of 1-methylimidazole, 119.8 g (1.3 mol) of dimethyl carbonate, and 83.1 g of methanol were placed in a 500-mL autoclave purged with nitrogen, and the mixture was stirred at 120° C. for 22 hours. The obtained reaction mixture was cooled to 25° C., and concentrated under reduced pressure, thereby obtaining a white solid. The obtained white solid was washed with toluene, and then dried under reduced pressure, thereby obtaining 47.8 g of a compound represented by the above formula (DMIm-CO$_2$) (yield: 34%). The $^1$H-NMR analysis results of the compound represented by the above formula are shown below.

$^1$H-NMR (CD$_3$OD) δ (ppm)=7.46 (s, 2H), 4.08 (s, 6H)

Production Example 1-2: Synthesis of
1-octyl-3-methylimidazolium-2-carboxylate

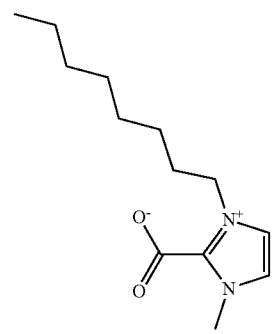 [SMILES: CCCCCCCC[n+]1ccn(C)c1C(=O)[O-]]

25.0 g (139 mol) of 1-octylimidazole, 16.7 g (185 mmol) of dimethyl carbonate, and 25.1 g of methanol were placed in a 180-mL autoclave purged with nitrogen, and the mixture was stirred at 125° C. for 29 hours. The mixture was cooled to room temperature, 8.5 g (94 mmol) of dimethyl carbonate was added thereto, followed by further stirring at 130° C. for 3 hours. The obtained reaction mixture was cooled to 25° C., thereby obtaining 44.0 g of a methanol solution of a compound represented by the above formula (OMIm-CO$_2$) (75 wt %, yield: 99%). The $^1$H-NMR analysis results of the compound represented by the above formula are shown below.

$^1$H-NMR (CD$_3$OD) δ (ppm)=7.67 (s, 1H), 7.61 (s, 1H), 4.22 (t, J=7.2 Hz, 2H), 3.94 (s, 3H), 1.91-1.84 (m, 2H), 1.32-1.26 (m, 10H), 0.85 (t, J=7.2 Hz, 3H)

Production Example 1-3: Synthesis of
p-chloro-N-t-butoxycarbonylaniline

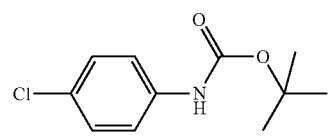

0.20 g (1.6 mmol) of p-chloroaniline, 0.17 g (1.7 mmol) of triethylamine, and 1 mL of THF were placed in a 15-mL test tube purged with nitrogen. While stirring the mixture, 0.38 g (1.7 mmol) of di-t-butyl dicarbonate/1 mL of THF solution was added dropwise. The resulting mixture was stirred at 25° C. for 24 hours, and then further stirred at 40° C. for 18 hours. The obtained reaction mixture was cooled to 25° C., and dried under reduced pressure, thereby obtaining 0.30 g of a compound represented by the above formula (p-chloro-N-t-butoxycarbonylaniline) (yield: 83%). The $^1$H-NMR analysis results of the compound represented by the above formula are shown below.

$^1$H-NMR (CDCl$_3$) δ (ppm)=7.31 (d, J=8.8 Hz, 2H), 7.24 (d, J=8.8 Hz, 2H), 6.45 (s, 1H), 1.51 (s, 9H)

Production Example 1-4: Synthesis of m-chloro-N-t-butoxycarbonylaniline

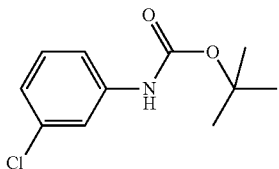

2.0 g (15.7 mmol) of m-chloroaniline, 1.8 g (17.3 mmol) of triethylamine, and 10 mL of THF were placed in a 100-mL test tube purged with nitrogen. While stirring the mixture, 3.4 g (15.7 mmol) of di-t-butyl dicarbonate/10 mL of THF solution was added dropwise. The resulting mixture was stirred at 25° C. for 4 hours, and then further stirred at 40° C. for 24 hours. After the obtained reaction mixture was cooled to 25° C., the solvent was distilled off. Then, 20 mL of toluene was added to the obtained concentrated residue, and the resulting mixture was washed once with 20 mL of 1 M citric acid aqueous solution and once with 20 mL of water. The obtained organic phase was dried over magnesium sulfate, and then dried under reduced pressure, thereby obtaining 1.4 g of a compound represented by the above formula (m-chloro-N-t-butoxycarbonylaniline) (yield: 39%). The $^1$H-NMR analysis results of the compound represented by the above formula are shown below.

$^1$H-NMR (CDCl$_3$) δ (ppm)=7.52 (s, 1H), 7.21-7.14 (m, 2H), 7.00 (dt, J=7.5, 1.7 Hz, 1H), 6.52 (s, 1H), 1.52 (s, 9H)

Production Example 1-5: Synthesis of p-isopropyl-N-t-butoxycarbonylaniline

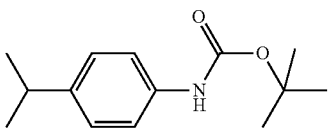 [SMILES: CC(C)c1ccc(NC(=O)OC(C)(C)C)cc1]

1.0 g (7.4 mmol) of p-isopropylaniline, 0.8 g (8.1 mmol) of triethylamine, and 5 mL of THF were placed in a 100-mL test tube purged with nitrogen. While stirring the mixture, 1.8 g (8.1 mmol) of di-t-butyl dicarbonate/5 mL of THF solution was added dropwise, and stirred at 25° C. for 17 hours. The solvent of the obtained reaction mixture was distilled off, and the resulting concentrated residue was washed with 5 mL of heptane. The obtained solid was dried under reduced pressure, thereby obtaining 1.7 g of a compound represented by the above formula (p-isopropyl-N-t-butoxycarbonylaniline) (yield: 98%). The $^1$H-NMR analysis results of the compound represented by the above formula are shown below.

$^1$H-NMR (CDCl$_3$) δ (ppm)=7.26 (d, J=8.3 Hz, 2H), 7.14 (d, J=8.3 Hz, 2H), 6.39 (s, 1H), 2.89-2.82 (m, 1H), 1.51 (s, 9H), 1.22 (d, J=6.8 Hz, 6H)

Production Example 1-6: Synthesis of p-octyl-N-t-butoxycarbonylaniline

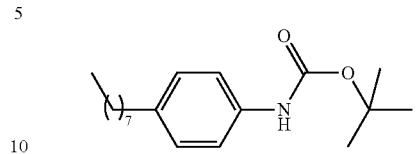

2.0 g (9.7 mmol) of p-n-octylaniline, 1.1 g (10.9 mmol) of triethylamine, and 10 mL of THF were placed in a 100-mL test tube purged with nitrogen. While stirring the mixture, 2.3 g (10.5 mm) of di-t-butyl dicarbonate/10 mL of THF solution was added dropwise, and stirred at 25° C. for 21 hours. The obtained reaction mixture was dried under reduced pressured, thereby obtaining 3.0 g of a compound represented by the above formula (p-octyl-N-t-butoxycarbonylaniline) (yield: 100%). The $^1$H-NMR analysis results of the compound represented by the above formula are shown below.

$^1$H-NMR (CDCl$_3$) δ (ppm)=7.26-7.24 (m, 2H), 7.09 (d, J=8.3 Hz, 2H), 6.39 (s, 1H), 2.54 (t, J=7.7 Hz, 2H), 1.53 (m, 2H), 1.51 (s, 9H), 1.28-1.26 (m, 10H), 0.87 (t, J=6.8 Hz, 3H)

Production Example 1-7: Synthesis of p-methoxy-N-t-butoxycarbonylaniline

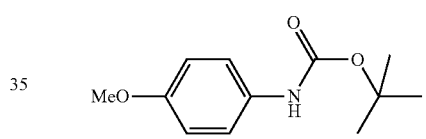

1.0 g (8.1 mmol) of p-anisidine, 0.9 g (8.9 mmol) of triethylamine, and 5 mL of THF were placed in a 100-mL test tube purged with nitrogen. While stirring the mixture, 2.0 g (9.2 mmol) of di-t-butyl dicarbonate/5 mL of THF solution was added dropwise, and stirred at 25° C. for 17 hours. The solvent of the obtained reaction mixture was distilled off, and the resulting concentrated residue was washed with 5 mL of heptane. After washing, the obtained solid was dried under reduced pressure, thereby obtaining 1.6 g of a compound represented by the above formula (p-methoxy-N-t-butoxycarbonylaniline) (yield: 88%). The $^1$H-NMR analysis results of the compound represented by the above formula are shown below.

$^1$H-NMR (CDCl$_3$) δ (ppm)=7.26 (d, J=8.8 Hz, 2H), 6.83 (d, J=8.8 Hz, 2H), 6.33 (s, 1H), 3.78 (s, 3H), 1.51 (s, 9H)

Production Example 1-8: Synthesis of p-vinyl-N-t-butoxycarbonylaniline

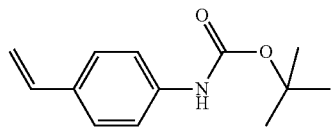 [SMILES: C=Cc1ccc(NC(=O)OC(C)(C)C)cc1]

1.0 g (8.4 mmol) of p-vinylaniline, 0.9 g (8.9 mmol) of triethylamine, and 10 mL of THF were placed in a 50-mL test tube purged with nitrogen, and the resulting mixture was cooled to 0° C. While stirring the mixture, 2.0 g (9.2 mmol) of di-t-butyl dicarbonate/10 mL of THF solution was added dropwise, stirred at 0° C. for 90 hours, and then stirred at 30° C. for 21.5 hours. 0.4 g (4.2 mmol) of diethanolamine was added dropwise to the obtained mixture. After stirring for 1 hour, the obtained reaction mixture was dried under reduced pressure. 20 mL of toluene and 10 mL of water were added to the obtained concentrated residue, and liquid separation was performed. The obtained organic phase was dried under reduced pressure, thereby obtaining 1.8 g of a compound represented by the above formula (p-vinyl-N-t-butoxycarbonylaniline) (yield: 98%). The $^1$H-NMR analysis results of the compound represented by the above formula are shown below.

$^1$H-NMR (DMSO-d6) δ (ppm)=9.42 (s, 1H), 7.44-7.34 (m, 4H), 6.67-6.60 (m, 1H), 5.71-5.66 (m, 1H), 5.14-5.11 (m, 1H), 1.47 (s, 9H)

Production Example 1-9: Synthesis of 2,6-diisopropyl-N-t-butoxycarbonylaniline

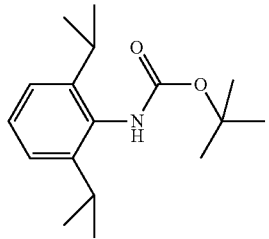 [SMILES: CC(C)c1cccc(C(C)C)c1NC(=O)OC(C)(C)C]

1.0 g (5.6 mmol) of 2,6-diisopropylaniline, 0.6 g (5.6 mmol) of triethylamine, and 5 mL of THF were placed in a 100-mL test tube purged with nitrogen. While stirring the mixture, 1.2 g (5.6 mmol) of di-t-butyl dicarbonate/5 mL of THF solution was added dropwise, and stirred at 25° C. for 21 hours. After the solvent of the obtained reaction mixture was distilled off, 10 mL of toluene was added to the obtained concentrated residue, washed with 15 mL of acetic acid solution (1 g/15 mL) and 10 mL of water, and dried over magnesium sulfate. The obtained organic phase was dried under reduced pressure, thereby obtaining 1.1 g of a compound represented by the above formula (2,6-diisopropyl-N-t-butoxycarbonylaniline) (yield: 71%). The $^1$H-NMR analysis results of the compound represented by the above formula are shown below. The $^1$H-NMR analysis results showed that this compound was a mixture of rotamers.

$^1$H-NMR (CDCl$_3$) δ (ppm)=7.26 (m, 1H), 7.14 (d, J=7.1 Hz, 2H), 5.81 (s, 0.7H), 5.58 (s, 0.3H), 3.18-3.17 (m, 2H), 1.51 (s, 6H), 1.37 (s, 3H), 1.21 (d, J=6.8 Hz, 12H)

Production Example 1-10: Synthesis of N-t-butoxycarbonylbenzylamine

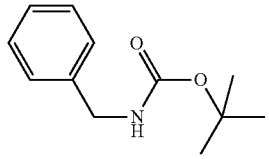

3.1 g (14.2 mmol) of di-t-butyl dicarbonate, 1.6 g (15.8 mmol) of triethylamine, and 10 mL of THF were placed in a 50-mL test tube purged with nitrogen, and a mixture of 1.5 g (14.0 mmol) of benzylamine and 5 mL of THF was added dropwise. After the resulting mixture was stirred at 25° C. for 3 hours, 0.2 g (1.8 mmol) of benzylamine was further added, and the mixture was stirred for 15 hours. After the obtained reaction mixture was concentrated under reduced pressure, a liquid separation operation was carried out, and the obtained organic phase was concentrated under reduced pressure, thereby obtaining 2.8 g of a compound represented by the above formula (N-t-butoxycarbonylbenzylamine) (yield: 85%). The $^1$H-NMR analysis results of the compound represented by the above formula are shown below.

$^1$H-NMR (CDCl$_3$) δ (ppm)=7.35-7.26 (m, 5H), 4.83 (br, 1H), 4.32-4.31 (m, 2H), 1.46 (s, 9H)

Production Example 1-11: Synthesis of p-vinyl-N-t-butoxycarbonylbenzylamine

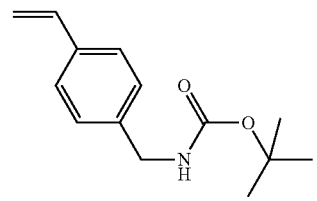 [SMILES: C=Cc1ccc(CNC(=O)OC(C)(C)C)cc1]

1.0 g (7.5 mmol) of p-vinylbenzylamine, 0.8 g (7.9 mmol) of triethylamine, and 10 mL of THF were placed in a 50-mL test tube purged with nitrogen, and the resulting mixture was cooled to 0° C. While stirring the mixture, 1.8 g (8.3 mmol) of di-t-butyl dicarbonate/10 mL of THF solution was added dropwise, and stirred at 25° C. for 47 hours. 0.5 g (4.8 mmol) of diethanolamine was added dropwise to the obtained mixture. After stirring for 1 hour, the obtained reaction mixture was dried under reduced pressure. 20 mL of toluene and 10 mL of water were added to the obtained concentrated residue, and liquid separation was performed. The obtained organic phase was dried under reduced pressure, thereby obtaining 1.8 g of a compound represented by the above formula (p-vinyl-N-t-butoxycarbonylbenzylamine) (yield: 103%). The $^1$H-NMR analysis results of the compound represented by the above formula are shown below.

$^1$H-NMR (DMSO-d6) δ (ppm)=7.42-7.19 (m, 5H), 6.74-6.67 (m, 1H), 5.82-5.77 (m, 1H), 5.23-5.21 (m, 1H), 4.10 (d, J=5.6 Hz, 2H), 1.39 (s, 9H)

Production Example 1-12: Synthesis of 1,4-bis{2-[4-(t-butoxycarbonylamino)phenyl]propan-2-yl}benzene

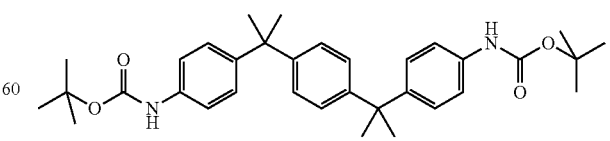

2.4 g (11.1 mmol) of di-t-butyl dicarbonate, 1.3 g (12.8 mmol) of triethylamine, and 15 mL of THF were placed in a 50-mL test tube purged with nitrogen. A mixture of 2.0 g (5.8 mmol) of 1,4-bis[2-(4-aminophenyl)propan-2-yl]benzene and 5 mL of THF was added dropwise, and stirred at 25° C. for 19 hours. The obtained reaction mixture was dried under reduced pressure, thereby obtaining a mixture of a compound represented by the above formula (1,4-bis{2-[4-(t-butoxycarbonylamino)phenyl]propan-2-yl}benzene) and unreacted 1-{2-[4-(t-butoxycarbonylamino)phenyl]-2-propyl}-4-[2-(4-aminophenyl) propan-2-yl]benzene. Part of the obtained mixture was sampled, and di-t-butyl dicarbonate was added. After stirring for 3 hours, diethanolamine was added. After concentration under reduced pressure, a liquid separation operation was carried out, and the obtained organic phase was concentrated under reduced pressure, thereby obtaining a compound represented by the above formula. The $^1$H-NMR analysis results of the compound represented by the above formula are shown below.

$^1$H-NMR (CDCl$_3$) δ (ppm)=7.26-7.22 (m, 4H), 7.15-7.13 (m, 4H), 7.08-7.07 (m, 4H), 6.40 (br, 2H), 1.62 (s, 12H), 1.50 (s, 18H)

Production Example 1-13: Synthesis of 1,3-bis{2-[4-(t-butoxycarbonylamino)phenyl]propan-2-yl}benzene

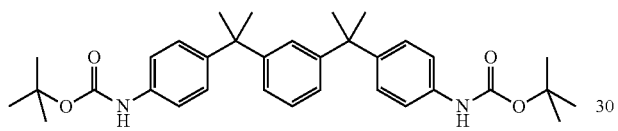

12.7 g (58.2 mmol) of di-t-butyl dicarbonate, 3.3 g (32.6 mmol) of triethylamine, and 25 g of THF were placed in a 200-mL test tube purged with nitrogen. To the resulting mixture, a mixture of 5.0 g (14.5 mmol) of 4,4-(1,3-phenylenediisopropylidene)bisaniline and 30 g of THF was added dropwise over 5 minutes. The mixture was stirred at 25° C. for 4 hours. To the mixture cooled to 0° C., 3.1 g (290 mmol) of diethanolamine was added over 10 minutes. After the mixture was concentrated under reduced pressure, 200 mL of ethyl acetate was added to the obtained concentrated residue, and washed 3 times with 100 mL of water. To the organic phase after washing, magnesium sulfate was added for drying, and the magnesium sulfate was then removed by filtration. The obtained filtrate was concentrated, thereby obtaining 6.3 g of a compound represented by the above formula (1,3-bis{2-[4-(t-butoxycarbonylamino)phenyl]propan-2-yl}benzene) (yield: 80%). The $^1$H-NMR analysis results of the compound represented by the above formula are shown below.

$^1$H-NMR (DMSO-d6) δ (ppm)=9.22 (s, 2H), 7.31 (d, J=8.6 Hz, 4H), 7.12 (t, J=7.7 Hz, 1H), 7.14-7.03 (m, 5H), 6.94 (d, J=7.7 Hz, 2H), 3.34 (s, 12H), 1.45 (s, 18H)

Production Example 1-14: Synthesis of 1,3-bis[4-(t-butoxycarbonylamino)phenoxy]benzene

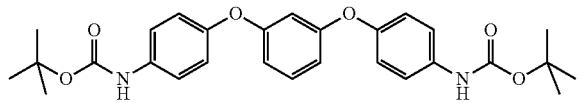 [SMILES: CC(C)(C)OC(=O)Nc1ccc(Oc2cccc(Oc3ccc(NC(=O)OC(C)(C)C)cc3)c2)cc1]

7.5 g (34.3 mmol) of di-t-butyl dicarbonate, 1.7 g (17.2 mmol) of triethylamine, and 40 mL of THF were placed in a 200-mL three-necked flask purged with nitrogen, and a mixture of 5.0 g (17.2 mmol) of 1,3-bis(4-aminophenoxy)benzene and 10 mL of THF was added dropwise. After the resulting mixture was stirred at 25° C. for 6 hours, 3.8 g (17.4 mmol) of di-t-butyl dicarbonate was added, and the resulting mixture was further stirred for 3 hours. Then, 2.8 g (26.3 mmol) of diethanolamine was added to the obtained reaction mixture. After concentration under reduced pressure, a liquid separation operation was carried out, and the obtained organic phase was concentrated under reduced pressure, thereby obtaining 8.0 g of a compound represented by the above formula (1,3-bis[4-(t-butoxycarbonylamino)phenoxy]benzene) (yield: 94%). The $^1$H-NMR analysis results of the compound represented by the above formula are shown below.

$^1$H-NMR (CD$_3$OD) δ (ppm)=7.38 (d, J=8.8 Hz, 4H), 7.23 (t, J=8.4 Hz, 1H), 6.93 (d, J=8.8 Hz, 4H), 6.40 (dd, J=8.4, 2.2 Hz, 2H), 6.50 (d, J=2.2 Hz, 1H), 1.51 (s, 18H)

Production Example 1-15: Synthesis of bis[3-(t-butoxycarbonylamino)phenyl]sulfone

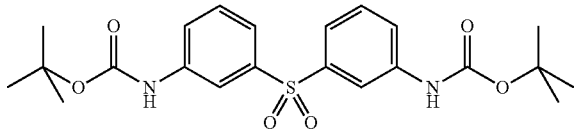 [SMILES: CC(C)(C)OC(=O)Nc1cccc(S(=O)(=O)c2cccc(NC(=O)OC(C)(C)C)c2)c1]

2.0 g (8.1 mmol) of bis(3-aminophenyl)sulfone, 3.6 g (16.5 mmol) of di-t-butyl dicarbonate, and 20 mL of THF were placed in a 100-mL test tube purged with nitrogen. While stirring the mixture, 1.8 g (17.8 mol) of triethylamine was added dropwise. The resulting mixture was stirred at 25° C. for 6 hours, and then further stirred at 40° C. for 16 hours. Thereafter, 5.5 g (25.2 mmol) of di-t-butyl dicarbonate was added, and further stirred at 40° C. for 48 hours. 1.7 g (15.9 mmol) of diethanolamine was added dropwise to the obtained reaction mixture. After stirring for 1 hour, the obtained reaction mixture was dried under reduced pressure. 15 mL of ethyl acetate and 15 mL of water were added to the obtained concentrated residue, and liquid separation was performed. The obtained organic phase was dried over magnesium sulfate, and then dried under reduced pressure, thereby obtaining 3.5 g of a compound represented by the above formula (bis[3-(t-butoxycarbonylamino)phenyl]sulfone) (yield: 97%). The $^1$H-NMR analysis results of the compound represented by the above formula are shown below.

$^1$H-NMR (CDCl$_3$) δ (ppm)=7.86 (s, 2H), 7.68 (d, J=7.3 Hz, 2H), 7.58 (d, J=7.3 Hz, 2H), 7.43-7.39 (m, 2H), 6.67 (s, 2H), 1.51 (s, 18H)

Production Example 2-1: Synthesis of 2.2'-bis{4-[4-(t-butoxycarbonylamino)phenoxy]phenyl}propane

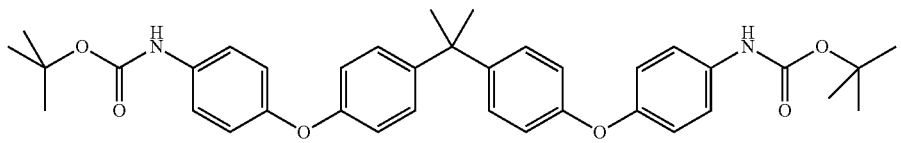 [SMILES: CC(C)(C)OC(=O)Nc1ccc(Oc2ccc(C(C)(C)c3ccc(Oc4ccc(NC(=O)OC(C)(C)C)cc4)cc3)cc2)cc1]

5.6 g (25.6 mmol) of di-t-butyl dicarbonate, 2.7 g (26.8 mmol) of triethylamine, and 25 g of THF were placed in a 200-mL three-necked flask purged with nitrogen, and the mixture of 5.0 g (12.2 mmol) of 2.2'-bis[4-(4-aminophenoxy)phenyl]propane and 8.5 g of THF was added dropwise thereto. The resulting mixture was stirred at 25° C. for 4.5 hours, and then further stirred at 45° C. for 2 hours. After the obtained reaction mixture was cooled to 25° C., 0.2 g (1.4 mmol) of diethanolamine was added to the reaction mixture, stirred at 25° C. for 2 hours, concentrated under reduced pressure, and a liquid separation operation was performed. The obtained organic phase was concentrated under reduced pressure, thereby obtaining 7.4 g of the compound represented by the above formula (2.2'-bis{4-[4-(t-butoxycarbonylamino) phenoxy]phenyl}propane) (yield 99%). The H-NMR analysis results of the compound represented by the above formula are shown below.

$^1$H-NMR (CDCl$_3$) δ (ppm)=7.31 (d, J=8.6 Hz, 4H), 7.15 (d, J=9.1 Hz, 4H), 6.96 (d, J=9.1 Hz, 4H), 6.85 (d, J=9.1 Hz, 2H), 6.42 (s, 2H), 1.65 (s, 6H), 1.52 (s, 18H)

Production Example 1-16: Synthesis of o-chloro-N-t-butoxycarbonylaniline

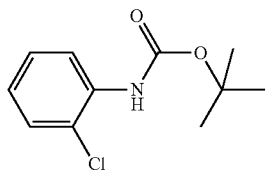

1.0 g (6.5 mmol) of o-chlorophenyl isocyanate and 2.0 g (27.0 mmol) of t-butanol were placed in a 15-mL test tube purged with nitrogen, and stirred at 90° C. for 3 hours. After the obtained reaction mixture was cooled to 25° C., the solvent was distilled off. The obtained concentrated residue was dissolved in chloroform, and insoluble substances were removed by filtration. The obtained filtrate was dried under reduced pressure, thereby obtaining 1.0 g of a compound represented by the above formula (o-chloro-N-t-butoxycarbonylaniline) (yield: 67%). The $^1$H-NMR analysis results of the compound represented by the above formula are shown below.

$^1$H-NMR (CDCl$_3$) δ (ppm)=8.16 (d, J=8.2 Hz, 1H), 7.33 (dd, J=8.2, 1.4 Hz, 1H), 7.24 (t, J=7.7 Hz, 1H), 7.01 (s, 1H), 6.96 (td, J=7.7, 1.4 Hz, 1H), 1.53 (s, 9H)

Production Example 1-17: Synthesis of bis[4-(t-butoxycarbonylamino)phenyl]methane

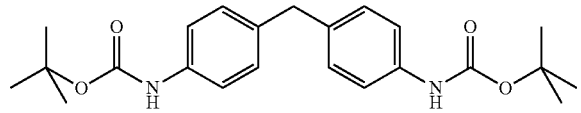 [SMILES: CC(C)(C)OC(=O)Nc1ccc(Cc2ccc(NC(=O)OC(C)(C)C)cc2)cc1]

15.0 g (60 mmol) of 4,4'-methylenediphenyl diisocyanate, 22.2 g (300 mmol) of t-butanol, and 44 g of toluene were placed in a 200-mL test tube purged with nitrogen, and stirred at 85° C. for 3 hours. The obtained reaction mixture was concentrated under reduced pressure, thereby obtaining 22.8 g of a compound represented by the above formula (bis[4-(t-butoxycarbonylamino)phenyl]methane) (yield: 96%). The $^1$H-NMR analysis results of the compound represented by the above formula are shown below.

$^1$H-NMR (DMSO-d6) δ (ppm)=9.23 (s, 2H) 7.34 (d, J=8.6 Hz, 4H), 7.05 (d, J=8.6 Hz, 4H), 3.76 (s, 2H), 1.45 (s, 18H)

Production Example 1-18: Synthesis of p-chloro-N-methoxycarbonylaniline

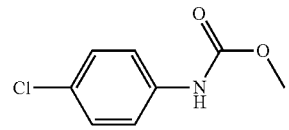

1.0 g (6.5 mmol) of p-chlorophenyl isocyanate and 20 mL of methanol were placed in a 50-mL test tube purged with nitrogen, and stirred at 70° C. for 3 hours. The obtained reaction mixture was dried under reduced pressure, thereby obtaining 1.1 g of a compound represented by the above formula (p-chloro-N-methoxycarbonylaniline) (yield: 91%). The $^1$H-NMR analysis results of the compound represented by the above formula are shown below.

$^1$H-NMR (DMSO-d6) δ (ppm)=9.79 (br, 1H), 7.47 (d, J=8.8 Hz, 2H), 7.33 (d, J=8.8 Hz, 2H), 3.66 (s, 3H)

Production Example 1-19: Synthesis of p-chloro-N-isopropoxycarbonylaniline

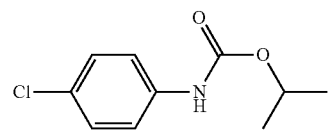

1.0 g (6.5 mmol) of p-chlorophenyl isocyanate and 2.0 g (33.3 mmol) of isopropanol were placed in a 15-mL test tube purged with nitrogen, and stirred at 90° C. for 3 hours. The obtained reaction mixture was cooled to 25° C., and then dried under reduced pressure, thereby obtaining 1.3 g of a compound represented by the above formula (p-chloro-N-isopropoxycarbonylaniline) (yield: 93%). The $^1$H-NMR analysis results of the compound represented by the above formula are shown below.

$^1$H-NMR (CDCl$_3$) δ (ppm)=7.33 (d, J=8.6 Hz, 2H), 7.26 (d, J=9.1 Hz, 2H), 6.50 (s, 1H), 5.04-4.98 (m, 1H), 1.30 (d, J=6.3 Hz, 6H)

Production Example 1-20: Synthesis of p-chloro-N-octoxycarbonylaniline

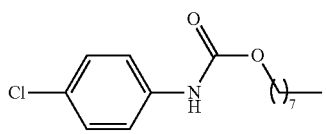

1.0 g (6.5 mmol) of p-chlorophenyl isocyanate, 0.9 g (6.9 mol) of n-octanol, and 2.5 mL of toluene were placed in a 15-mL test tube purged with nitrogen, and stirred at 110° C. for 3 hours. The obtained reaction mixture was cooled to 25° C., and then dried under reduced pressure, thereby obtaining 1.8 g of a compound represented by the above formula (p-chloro-N-octoxycarbonylaniline) (yield: 97%). The $^1$H-NMR analysis results of the compound represented by the above formula are shown below.

$^1$H-NMR (CDCl$_3$) δ (ppm)=7.33 (d, J=8.6 Hz, 2H), 7.27-7.24 (m, 2H), 6.62 (s, 1H), 4.14 (t, J=6.7 Hz, 2H), 1.69-1.62 (m, 2H), 1.36-1.29 (m, 10H), 0.88 (t, J=6.8 Hz, 3H)

Production Example 1-21: Synthesis of p-chloro-N-phenoxycarbonylaniline

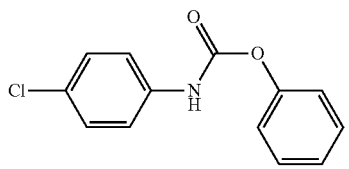 [SMILES: O=C(Nc1ccc(Cl)cc1)Oc1ccccc1]

1.0 g (6.5 mmol) of p-chlorophenyl isocyanate, 0.6 g (6.5 mmol) of phenol, and 2.5 mL of toluene were placed in a 15-mL test tube purged with nitrogen, and stirred at 110° C. for 3 hours. The obtained reaction mixture was cooled to 25° C., and then dried under reduced pressure, thereby obtaining 1.5 g of a compound represented by the above formula (p-chloro-N-phenoxycarbonylaniline) (yield: 93%). The $^1$H-NMR analysis results of the compound represented by the above formula are shown below.

$^1$H-NMR (CDCl$_3$) δ (ppm)=7.41-7.39 (m, 4H), 7.28-7.25 (m, 3H), 7.18 (d, J=7.6 Hz, 2H), 6.97 (s, 1H)

Example 1-1: Synthesis of DMIm-pClPI

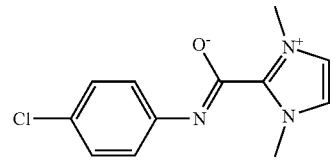 [SMILES: Cn1cc[n+](C)c1/C([O-])=N/c1ccc(Cl)cc1]

0.3 g (2.2 mmol) of DMIm-CO$_2$ obtained in Production Example 1-1, 0.5 g (2.2 mmol) of p-chloro-N-t-butoxycarbonylaniline obtained in Production Example 1-3, and 17 mL of toluene were placed in a three-necked flask purged with nitrogen. The resulting mixture was stirred at 110° C. for 3 hours. After the obtained reaction mixture was cooled to 25° C., the mixture was concentrated under reduced pressure, thereby obtaining 0.3 g of a compound represented by the above formula (DMIm-pClPI) (yield: 55%). The $^1$H-NMR analysis results of the compound represented by the above formula are shown below.

$^1$H-NMR (DMSO-d6) δ (ppm)=7.54-7.53 (m, 4H), 7.14 (d, j=8.8 Hz, 2H), 3.99 (s, 6H)

Example 1-2: Synthesis of DMIm-mClPI

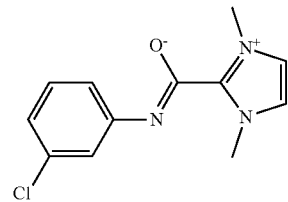 [SMILES: Cn1cc[n+](C)c1/C([O-])=N/c1cccc(Cl)c1]

0.3 g (2.2 mmol) of DMIm-CO$_2$ obtained in Production Example 1-1, 0.5 g (2.2 mmol) of m-chloro-N-t-butoxycarbonylaniline obtained in Production Example 1-4, and 9 mL of toluene were placed in a 30-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.4 g of a compound represented by the above formula (DMIm-mClPI) (yield: 73%). The $^1$H-NMR analysis results of the compound represented by the above formula are shown below.

$^1$H-NMR (DMSO-d6) δ (ppm)=7.78 (t, J=2.0 Hz, 1H), 7.55 (s, 2H), 7.26 (d, J=8.0 Hz, 1H), 7.13 (t, J=8.0 Hz, 1H), 6.81 (dq, J=8.0, 1.1 Hz, 1H), 4.00 (s, 6H)

Example 1-3: Synthesis of DMIm-oClPI

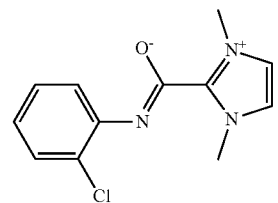 [SMILES: Cn1cc[n+](C)c1/C([O-])=N/c1ccccc1Cl]

0.3 g (2.2 mmol) of DMIm-$CO_2$ obtained in Production Example 1-1, 0.5 g (2.2 mmol) of o-chloro-N-t-butoxycarbonylaniline obtained in Production Example 1-16, and 9 mL of toluene were placed in a 30-mL test tube purged with nitrogen, and the resulting mixture was stirred at 110° C. for 6 hours. After the obtained reaction mixture was cooled to 25° C., filtration was performed, and the obtained white solid was dried under reduced pressure, thereby obtaining 0.47 g of a compound represented by the above formula (DMIm-oClPI) (yield: 85%). The $^1$H-NMR analysis results of the compound represented by the above formula are shown below.

$^1$H-NMR (DMSO-d6) δ (ppm)=7.93 (d, J=7.8 Hz, 1H), 7.57 (s, 2H), 7.28 (d, J=7.8 Hz, 1H), 7.09 (t, J=7.8 Hz, 1H), 6.80-6.78 (m, 1H), 4.09 (s, 6H)

Example 1-4: Synthesis of DMIm-piPrPI

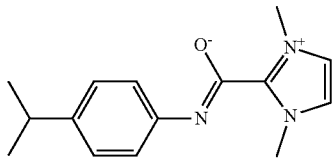 [SMILES: CC(C)c1ccc(/N=C(\[O-])c2n(C)cc[n+]2C)cc1]

0.2 g (1.4 mmol) of DMIm-$C_2$ obtained in Production Example 1-1, 0.34 g (1.4 mmol) of p-isopropyl-N-t-butoxycarbonylaniline obtained in Production Example 1-5, and 6 mL of toluene were placed in a 15-mL test tube purged with nitrogen, and the resulting mixture was stirred at 110° C. for 18 hours. After the obtained reaction mixture was cooled to 25° C., the solvent was distilled off under reduced pressure. 8 mL of toluene and 2 mL of water were added to the resulting concentrated residue, the resulting mixture was stirred at room temperature for 5 minutes, and the aqueous phase and the organic phase were separated. The obtained aqueous phase was dried under reduced pressure, thereby obtaining 0.3 g of a compound represented by the above formula (DMIm-piPrPI) (yield: 81%). The $^1$H-NMR analysis results of the compound represented by the above formula are shown below.

$^1$H-NMR (DMSO-d6) δ (ppm)=7.51 (s, 2H), 7.40 (d, J=8.3 Hz, 2H), 6.99 (d, J=8.3 Hz, 2H), 3.99 (s, 6H), 2.81-2.74 (m, 1H), 1.16 (d, J=6.8 Hz, 6H)

Example 1-5: Synthesis of DMIm-pOctPI

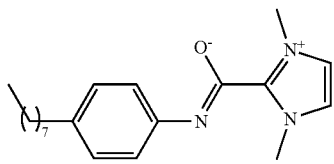

0.2 g (1.6 mmol) of DMIm-$CO_2$ obtained in Production Example 1-1, 0.5 g (1.6 mmol) of p-octyl-N-t-butoxycarbonylaniline obtained in Production Example 1-6, and 6 mL of toluene were placed in a 15-mL test tube purged with nitrogen, and the resulting mixture was stirred at 110° C. for 9 hours. The obtained reaction mixture was cooled to 25° C., and then dried under reduced pressure, thereby obtaining 0.5 g of a compound represented by the above formula (DMIm-pOctPI) (yield: 93%). The $^1$H-NMR analysis results of the compound represented by the above formula are shown below.

$^1$H-NMR (DMSO-d6) δ (ppm)=7.51 (s, 2H), 7.40 (d, J=8.3 Hz, 2H), 6.93 (d, J=8.3 Hz, 2H), 3.98 (s, 6H), 2.46 (t, J=7.6 Hz, 2H), 1.52-1.51 (m, 2H), 1.25-1.23 (m, 10H), 0.85 (t, J=6.8 Hz, 3H)

Example 1-6: Synthesis of DMIm-pMeOPI

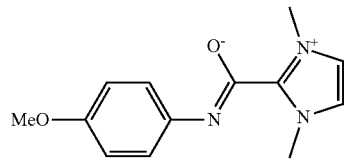 [SMILES: COc1ccc(/N=C(\[O-])c2n(C)cc[n+]2C)cc1]

0.3 g (2.2 mmol) of DMIm-$CO_2$ obtained in Production Example 1-1, 0.5 g (2.2 mmol) of p-methoxy-N-t-butoxycarbonylaniline obtained in Production Example 1-7, and 9 mL of toluene were placed in a 30-mL test tube purged with nitrogen, and the resulting mixture was stirred at 110° C. for 12 hours. After the obtained reaction mixture was cooled to 25° C., filtration was performed, and the obtained residue was dried under reduced pressure, thereby obtaining 0.4 g of a compound represented by the above formula (DMIm-pMeOPI) (yield: 73%). The $^1$H-NMR analysis results of the compound represented by the above formula are shown below.

$^1$H-NMR (DMSO-d6) δ (ppm)=7.50-7.49 (m, 4H), 6.71 (d, J=9.1 Hz, 2H), 3.99 (s, 6H), 3.68 (s, 3H)

Example 1-7: Synthesis of DMIm-pVPI

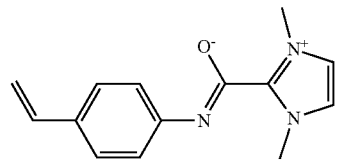 [SMILES: C=Cc1ccc(/N=C(\[O-])c2n(C)cc[n+]2C)cc1]

0.14 g (1.0 mmol) of DMIm-$CO_2$ obtained in Production Example 1-1, 0.21 g (1.0 mmol) of p-vinyl-N-t-butoxycarbonylaniline obtained in Production Example 1-8, and 40 mL of chlorobenzene were placed in a 50-mL test tube purged with nitrogen, and stirred at 130° C. for 2.5 hours. After the obtained reaction mixture was cooled to 25° C., filtration was performed, and the obtained filtrate was concentrated under reduced pressure. The obtained concentrate was mixed with methanol, filtration was performed, and the obtained filtrate was concentrated under reduced pressure, thereby obtaining 0.19 g of a compound represented by the above formula (DMIm-pVPI) (yield: 82%). The $^1$H-NMR analysis results of the compound represented by the above formula are shown below.

$^1$H-NMR (DMSO-d6) δ (ppm)=7.56 (s, 2H), 7.52-7.25 (m, 4H), 6.67-6.60 (m, 1H), 5.65-5.60 (m, 1H), 5.06-5.03 (m, 1H), 4.01 (s, 6H)

Example 1-8: Synthesis of DMIm-26iPrPI

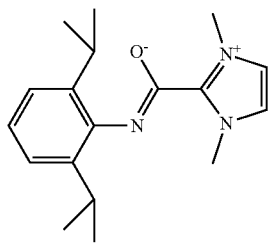 [SMILES: CC(C)c1cccc(C(C)C)c1/N=C(\[O-])c1n(C)cc[n+]1C]

0.3 g (1.8 mmol) of DMIm-$CO_2$ obtained in Production Example 1-1, 0.5 g (1.8 mmol) of 2,6-diisopropyl-N-t-butoxycarbonylaniline obtained in Production Example 1-9, and 6 mL of toluene were placed in a 15-mL test tube purged with nitrogen, and the resulting mixture was stirred at 110° C. for 12 hours. After the obtained reaction mixture was cooled to 25° C., filtration was performed, and the obtained residue was dried under reduced pressure, thereby obtaining 0.5 g of a compound represented by the above formula (DMIm-26iPrPI) (yield: 93%). The $^1$H-NMR analysis results of the compound represented by the above formula are shown below.

$^1$H-NMR (DMSO-d6) δ (ppm)=7.54 (s, 2H), 6.94 (d, J=7.6 Hz, 2H), 6.81 (t, J=7.6 Hz, 1H), 4.01 (s, 6H), 3.20-3.13 (m, 2H), 1.10 (d, J=6.8 Hz, 12H)

Example 1-9: Synthesis of DMIm-BnI

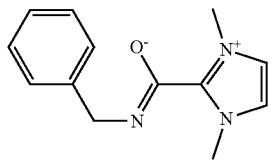 [SMILES: Cn1cc[n+](C)c1/C([O-])=N/Cc1ccccc1]

0.5 g (3.6 mmol) of DMIm-$CO_2$ obtained in Production Example 1-1, 0.6 g (2.9 mmol) of N-t-butoxycarbonylbenzylamine obtained in Production Example 1-10, and 15 mL of chlorobenzene were placed in a 100-mL test tube purged with nitrogen, and the resulting mixture was stirred at 130° C. for 3 hours. After the obtained reaction mixture was cooled to 25° C., filtration was performed, and the obtained filtrate was dried under reduced pressure. 15 mL of toluene and 50 mL of water were added to the resulting concentrated residue, the resulting mixture was stirred at room temperature for 5 minutes, and the aqueous phase and the organic phase were separated. The obtained aqueous phase was dried under reduced pressure, thereby obtaining 0.3 g of a compound represented by the above formula (DMIm-BnI) (yield: 41%). The $^1$H-NMR analysis results of the compound represented by the above formula are shown below.

$^1$H-NMR (DMSO-d6) δ (ppm)=7.48 (s, 2H), 7.34 (d, J=7.3 Hz, 2H), 7.25-7.23 (m, 2H), 7.12 (t, J=7.3 Hz, 1H), 4.40 (s, 2H), 3.97 (s, 6H)

Example 1-10: Synthesis of DMIm-pVPMI

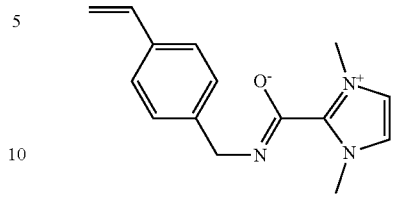

0.24 g (1.7 mmol) of DMIm-$CO_2$ obtained in Production Example 1-1, 0.20 g (0.9 mmol) of p-vinyl-N-t-butoxycarbonylbenzylamine obtained in Production Example 1-11, and 40 mL of toluene were placed in a 50-mL test tube purged with nitrogen, and the resulting mixture was stirred at 110° C. for 13 hours. After the obtained reaction mixture was cooled to 25° C., filtration was performed, and the obtained filtrate was concentrated under reduced pressure, thereby obtaining 0.07 g of a compound represented by the above formula (DMIm-pVPMI) (yield: 32%). The $^1$H-NMR analysis results of the compound represented by the above formula are shown below.

$^1$H-NMR (DMSO-d6) δ (ppm)=7.45 (s, 2H), 7.42-7.20 (m, 4H), 6.75-6.67 (m, 1H), 5.79-5.74 (m, 1H), 5.20-5.17 (m, 1H), 4.40 (s, 2H), 3.99 (s, 6H)

Example 1-11: Synthesis of DMIm-mMDI

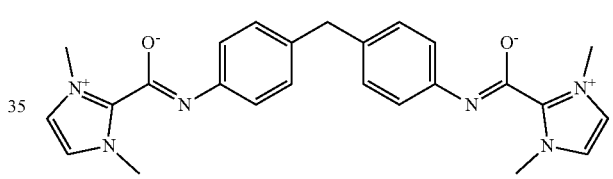

3.0 g (21.4 mmol) of DMIm-$CO_2$ obtained in Production Example 1-1, 3.5 g (8.8 mmol) of bis[4-(t-butoxycarbonylamino)phenyl]methane obtained in Production Example 1-17, and 120 mL of chlorobenzene were placed in a 200-mL test tube purged with nitrogen, and the resulting mixture was stirred at 130° C. for 3 hours. Concentration under reduced pressure was performed, thereby obtaining 3.9 g of a compound represented by the above formula (DMIm-mMDI) (yield: 100%). The $^1$H-NMR analysis results of the compound represented by the above formula are shown below.

$^1$H-NMR (DMSO-d6) δ (ppm)=7.51 (s, 4H), 7.41 (d, J=8.2 Hz, 4H), 6.95 (d, J=8.2 Hz, 4H), 3.99 (s, 12H), 3.83 (s, 2H)

Example 1-12: Synthesis of DMIm-4,4'-(1,4-PBDMM)BPI

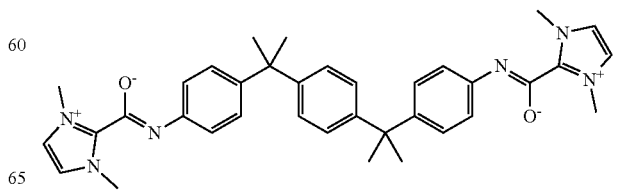

0.2 g (1.4 mmol) of DMIm-CO$_2$ obtained in Production Example 1-1, 8 mL of chlorobenzene, and 0.4 g (0.7 mmol) of 1,4-bis{2-[4-(t-butoxycarbonylamino)phenyl]propan-2-yl}benzene obtained in Production Example 1-12 were placed in a three-necked flask purged with nitrogen, and the resulting mixture was stirred at 130° C. for 3 hours. After the obtained reaction mixture was cooled to 25° C., filtration was performed, and the obtained residue was dried under reduced pressure, thereby obtaining 0.3 g of a compound represented by the above formula (DMIm-4,4'-(1,4-PBDMM)BPI) (yield: 70%). The $^1$H-NMR analysis results of the compound represented by the above formula are shown below.

$^1$H-NMR (DMSO-d6) δ (ppm)=7.50 (s, 4H), 7.37 (d, J=8.4 Hz, 4H), 7.10 (s, 4H), 6.98 (d, J=8.4 Hz, 4H), 3.98 (s, 12H), 1.58 (s, 12H)

Example 1-13: Synthesis of DMIm-4,4'-(1,3-PBDMM)BPI

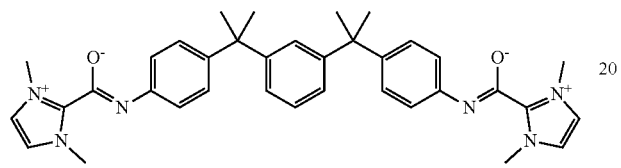

1.5 g (11.0 mmol) of DMIm-CO$_2$ obtained in Production Example 1-1, 100 mL of chlorobenzene, and 3.0 g (5.5 mmol) of 1,3-bis{2-[4-(t-butoxycarbonylamino)phenyl]propan-2-yl}benzene obtained in Production Example 1-13 were placed in a three-necked flask purged with nitrogen, and the resulting mixture was stirred at 130° C. for 3 hours. The obtained reaction mixture was cooled to 25° C., and then dried under reduced pressure. The obtained solid was washed 3 times with 100 ml of toluene, and dried under reduced pressure, thereby obtaining 2.2 g of a compound represented by the above formula (DMIm-4,4'-(1,3-PBDMM)BPI) (yield: 68%). The $^1$H-NMR analysis results of the compound represented by the above formula are shown below.

$^1$H-NMR (DMSO-d6) δ (ppm)=7.53 (s, 4H), 7.42-7.39 (m, 4H), 7.12 (s, 1H), 6.98-6.96 (m, 7H), 4.00 (s, 12H), 1.58 (s, 12H)

Example 1-14: Synthesis of DMIm-4,4'-(1,3-PBO)BPI

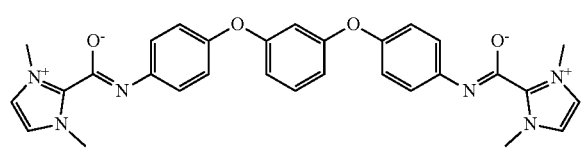 [SMILES: Cn1cc[n+](C)c1/C([O-])=N/c1ccc(Oc2cccc(Oc3ccc(/N=C(\[O-])c4n(C)cc[n+]4C)cc3)c2)cc1]

2.0 g (14 mmol) of DMIm-CO$_2$ obtained in Production Example 1-1, 80 mL of chlorobenzene, and 3.5 g (7.1 mmol) of 1,3-bis[4-(t-butoxycarbonylamino)phenoxy]benzene obtained in Production Example 1-14 were placed in a three-necked flask purged with nitrogen, and the resulting mixture was stirred at 130° C. for 3 hours. The obtained reaction mixture was cooled to 25° C., and then dried under reduced pressure, thereby obtaining 3.8 g of a compound represented by the above formula (DMIm-4,4'-(1,3-PBO)BPI) (yield: 99%). The $^1$H-NMR analysis results of the compound represented by the above formula are shown below.

$^1$H-NMR (CD$_3$OD) δ (ppm)=7.47 (s, 4H), 7.42 (d, J=9.0 Hz, 4H), 7.23 (t, J=8.2 Hz, 1H), 6.96 (d, J:=9.0 Hz, 4H), 6.63 (dd, J=8.2, 2.4 Hz, 2H), 6.57 (t, J=2.4 Hz, 1H), 3.98 (s, 12H)

Example 1-15: Synthesis of DMIm-3,3'-SO$_2$BPI

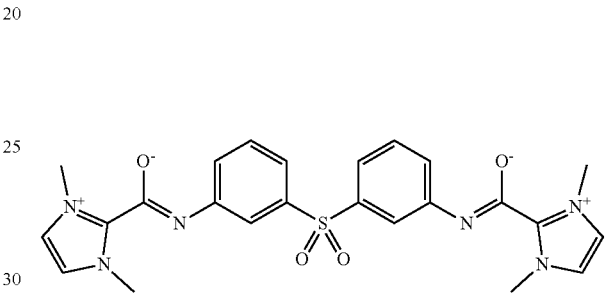

0.6 g (4.5 mmol) of DMIm-CO$_2$ obtained in Production Example 1-1, 1.0 g (2.2 mmol) of bis[3-(t-butoxycarbonylamino)phenyl]sulfone obtained in Production Example 1-15, and 18 mL of chlorobenzene were placed in a 30-mL test tube purged with nitrogen, and the resulting mixture was stirred at 130° C. for 6 hours. After the obtained reaction mixture was cooled to 25° C., filtration was performed, and the obtained brown solid was dried under reduced pressure, thereby obtaining 1.3 g of a compound represented by the above formula (DMIm-3,3'-SO$_2$BPI) (pure content: 1.1 g, yield: 99%). The $^1$H-NMR analysis results of the compound represented by the above formula are shown below.

$^1$H-NMR (DMSO-d6) δ (ppm)=7.68 (s, 2H), 7.63 (d, J=7.3 Hz, 2H), 7.56 (s, 4H), 7.44-7.38 (m, 2H), 7.34-7.30 (m, 2H), 4.01 (s, 12H)

Example 1-16: Synthesis of OMIm-mMDI

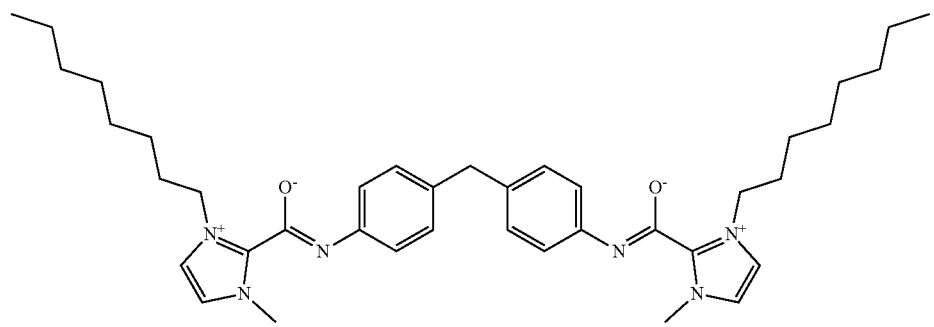 [SMILES: CCCCCCCC[n+]1ccn(C)c1/C([O-])=N/c1ccc(Cc2ccc(/N=C(\[O-])c3n(C)cc[n+]3CCCCCCCC)cc2)cc1]

4.9 g (pure content of OMIm-$CO_2$: 15 mmol) of the methanol solution of OMIm-$CO_2$ obtained in Production Example 1-2, 100 mL of chlorobenzene, and 2.5 g (6.3 mmol) of bis[4-(t-butoxycarbonylamino)phenyl]methane obtained in Production Example 1-17 were placed in a three-necked flask purged with nitrogen, and the resulting mixture was stirred at 130° C. for 5 hours. The obtained reaction mixture was cooled to 25° C., and then dried under reduced pressure, thereby obtaining 4.7 g of a compound represented by the above formula (OMIm-mMDI) (pure content: 4.0 g, yield: 99%). The $^1$H-NMR analysis results of the compound represented by the above formula are shown below.

$^1$H-NMR ($CD_3OD$) δ (ppm)=7.51 (m, 2H), 7.45 (m, 2H), 7.35-7.34 (m, 4H), 7.13-7.11 (m, 4H), 4.35 (t, J=7.4 Hz, 4H), 3.95 (s, 6H), 3.90 (s, 2H), 1.88 (m, 4H), 1.34-1.26 (m, 20H), 0.87 (t, J=7.6 Hz, 6H)

Example 1-17: Synthesis of DMIm-pClPI 0.2 g (1.4 mmol) of DMIm-$CO_2$ obtained in Production Example 1-1, 0.3 g (1.4 mmol) of p-chloro-N-methoxycarbonylaniline obtained in Production Example 1-18, and 6 mL of toluene were placed in a 15-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.3 g of DMIm-pClPI (yield: 86%).

Example 1-18: Synthesis of DMIm-pClPI 0.3 g (2.4 mmol) of DMIm-$C_2$ obtained in Production Example 1-1, 0.5 g (2.4 mmol) of p-chloro-N-isopropoxycarbonylaniline obtained in Production Example 1-19, and 9 mL of toluene were placed in a 30-mL test tube purged with nitrogen, and the resulting mixture was stirred at 110° C. for 6 hours. After the obtained reaction mixture was cooled to 25° C., filtration was performed, and the obtained white solid was dried under reduced pressure, thereby obtaining 0.5 g of DMIm-pClPI (yield: 86%).

Example 1-19: Synthesis of DMIm-pClPI 0.3 g (2.1 mmol) of DMIm-$CO_2$ obtained in Production Example 1-1, 0.6 g (2.1 mol) of p-chloro-N-octoxycarbonylaniline obtained in Production Example 1-20, and 9 mL of toluene were placed in a 30-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.4 g of DMIm-pClPI (yield: 76%).

Example 1-20: Synthesis of DMIm-pClPI 0.3 g (2.1 mmol) of DMIm-$CO_2$ obtained in Production Example 1-1, 0.5 g (2.1 mmol) of p-chloro-N-phenoxycarbonylaniline obtained in Production Example 1-21, and 9 mL of toluene were placed in a 30-mL test tube purged with nitrogen, and the resulting mixture was stirred at 110° C. for 3 hours. The obtained reaction mixture was cooled to 25° C., and then concentrated under reduced pressure, thereby obtaining a mixture of DMIm-pClPI and phenol. The $^1$H-NMR analysis of the obtained mixture showed that the yield of DMIm-pClPI was 98%.

Example 2-1: Synthesis of OMIm-4,4'-(1,4-PBDMM)BPI

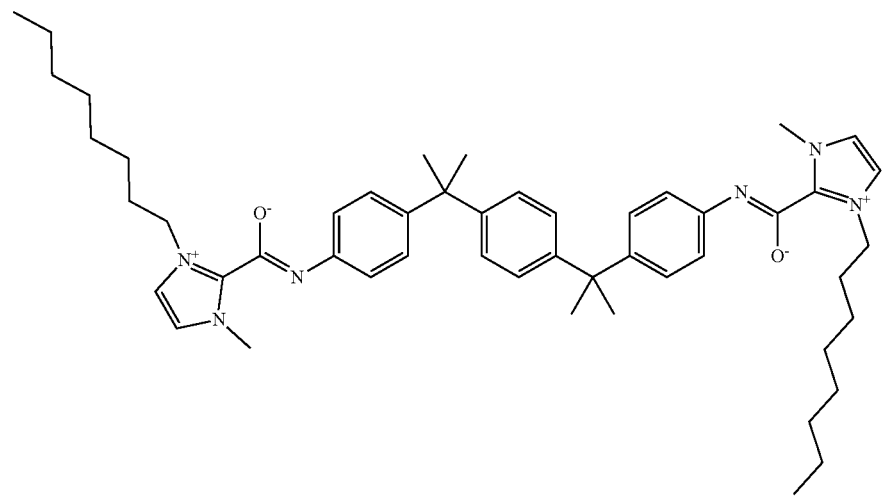 [SMILES: CCCCCCCC[n+]1ccn(C)c1/C([O-])=N/c1ccc(C(C)(C)c2ccc(C(C)(C)c3ccc(/N=C(\[O-])c4n(C)cc[n+]4CCCCCCCC)cc3)cc2)cc1]

3.5 g (pure content of OMIm-$CO_2$: 11.0 mmol) of the methanol solution of OMIm-$CO_2$ obtained in Production Example 1-2, 120 mL of chlorobenzene, and 3.0 g (5.5 mmol) of 1,4-bis{2-[4-(t-butoxycarbonylamino)phenyl]propan-2-yl}benzene obtained in Production Example 1-12 were placed in a three-necked flask purged with nitrogen, and the resulting mixture was stirred at 130° C. for 3 hours. After the obtained reaction mixture was cooled to 25° C., 50 mL of water was added, and liquid separation was performed. The obtained organic phase was dried under reduced pressure, thereby obtaining 1.90 g of a compound represented by the above formula (OMIm-4,4'-(1,4-PBDMM) BPI) (yield 44%). The $^1$H-NMR analysis results of the compound represented by the above formula are shown below.

$^1$H-NMR ($CD_3OD$) δ (ppm)=7.51 (d, j=2.0 Hz, 2H), 7.45 (d, j=2.0 Hz, 2H)), 7.26-7.23 (m, 4H), 7.15-7.11 (m, 8H), 4.36 (t, J=7.4 Hz, 4H), 3.96 (s, 6H), 1.90-1.88 (m, 4H), 1.64 (s, 12H), 1.34-1.26 (m, 20H), 0.86 (t, J=: 7.0 Hz, 6H)

Example 2-2: Synthesis of OMIm-4,4'-(1,3-PBDMM)BPI

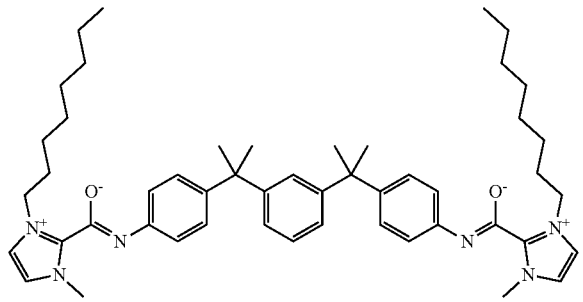 [SMILES: CCCCCCCC[n+]1ccn(C)c1/C([O-])=N/c1ccc(C(C)(C)c2cccc(C(C)(C)c3ccc(/N=C(\[O-])c4n(C)cc[n+]4CCCCCCCC)cc3)c2)cc1]

3.7 g (pure content of OMIm-CO$_2$: 11.6 mol) of the methanol solution of OMIm-CO$_2$ obtained in Production Example 1-2, 120 mL of chlorobenzene, and 3.2 g (5.8 mol) of 1,3-bis(2-[4-(t-butoxycarbonylamino)phenyl]propan-2-yl benzene obtained in Production Example 1-13 were placed in a three-necked flask purged with nitrogen, and the resulting mixture was stirred at 130° C. for 3 hours. After the obtained reaction mixture was cooled to 25° C., the solvent was distilled off. Then, the obtained concentrated residue was dissolved in 30 mL of dichloromethane, and the resulting mixture was washed 3 times with 50 mL of water. The obtained organic phase was dried under reduced pressure, thereby obtaining 4.4 g of a compound represented by the above formula (OMIm-4,4'-(1,3-PBDMM)BPI) (yield 95%). The $^1$H-NMR analysis results of the compound represented by the above formula are shown below.

$^1$H-NMR (CD$_3$OD) δ (ppm)=7.50 (d, j=2.0 Hz, 2H), 7.44 (d, j=2.0 Hz, 2H)), 7.28-7.26 (m, 5H), 7.15-7.09 (m, 5H), 7.02-7.01 (m, 2H), 4.36 (t, J=7.4 Hz, 4H), 3.96 (s, 6H), 1.90-1.88 (m, 4H), 1.61-1.59 (m, 12H), 1.34-1.26 (m, 20H), 0.86 (t, J=6.9 Hz, 6H)

Example 2-3: Synthesis of DMIm-BAPP

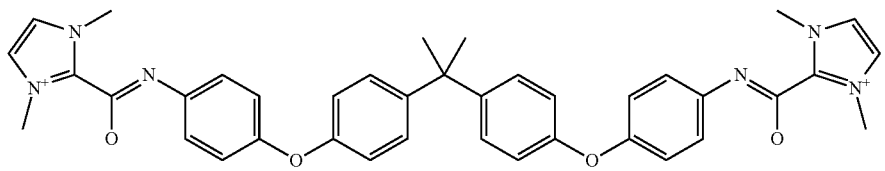 [SMILES: Cn1cc[n+](C)c1/C(O)=N/c1ccc(Oc2ccc(C(C)(C)c3ccc(Oc4ccc(/N=C(\O)c5n(C)cc[n+]5C)cc4)cc3)cc2)cc1]

2.0 g (14.3 mmol) of DMIm-02 obtained in Production Example 1-1, 72 g of chlorobenzene, and 4.4 g (7.1 mmol) of 2.2'-bis{4-[4-(t-butoxycarbonylamino) phenoxy] phenyl}propane obtained in Production Example 2-1 were placed in a three-neck flask purged with nitrogen, and the resulting mixture was stirred at 130° C. for 4 hours. After the obtained reaction mixture was cooled to 25° C., the supernatant was removed, and the resulting viscous liquid was dried under reduced pressure, thereby obtaining 3.5 g of a compound represented by the above formula (DMIm-BAPP) (yield 74%)). The $^1$H-NMR analysis results of the compound represented by the above formula are shown below.

$^1$H-NMR (DMSO-d6) δ (ppm)=7.57-7.53 (m, 8H), 7.17 (d, J=8.3 Hz, 4H), 6.82 (d, J=8.3 Hz, 8H), 4.00 (s, 12H), 1.60 (s, 6H)

Comparative Example 1: Synthesis of DMIm-mMDI 1.0 g (7.1 mmol) of DMIm-CO$_2$ obtained in Production Example 1-1, 0.9 g (3.6 mmol) of diphenylmethane diisocyanate, and 30 mL of toluene were placed in a 100-mL test tube purged with nitrogen, and the resulting mixture was stirred at 110° C. for 3 hours. The resulting reaction mixture was poorly soluble in DMSO, MeOH, or chloroform. The partially dissolved portion was analyzed using $^1$H-NMR; however, the obtained reaction mixture was not the target DMIm-mMDI.

The invention claimed is:

1. A method for producing an amidate compound, comprising reacting a urethane compound with a carboxylate compound, the urethane compound being represented by Formula (1):

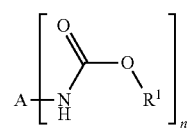

(1)

wherein R$^1$ represents a hydrocarbon group that may contain a heteroatom; A represents a substituted or unsubstituted hydrocarbon group; and n is an integer of 1 or more, the carboxylate compound being represented by Formula (2):

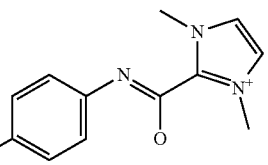

(2)

wherein R$^2$, R$^3$, R$^4$ and R$^5$ each represent a hydrocarbon group that may contain a heteroatom;
some or all of R$^2$, R$^3$, R$^4$, and R$^5$ may be bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom; and the amidate compound being represented by Formula (3):

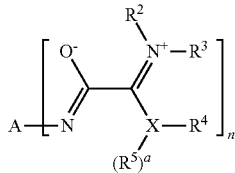 (3)

wherein A, n, $R^2$, $R^3$, $R^4$, $R^5$, X, and a are as defined above.

2. The method for producing an amidate compound according to claim 1, wherein the urethane compound represented by Formula (1) is a urethane compound represented by any one of the following Formulas (1-1), (1-2), and (1-3):

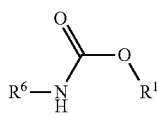 (1-1)

wherein $R^6$ represents a substituted or unsubstituted hydrocarbon group; and $R^1$ is as defined above;

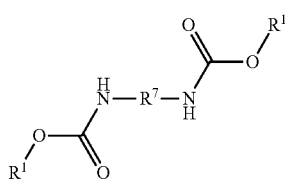 (1-2)

wherein $R^7$ represents a substituted or unsubstituted hydrocarbon group; and $R^1$ is as defined above; and

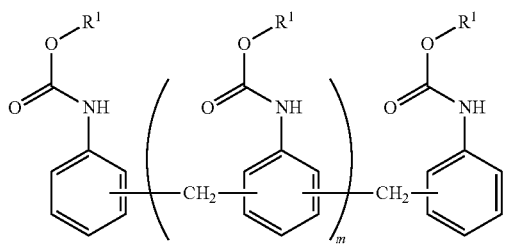 (1-3)

wherein m is an integer of 0 to 4; and $R^1$ is as defined above.

3. The method for producing an amidate compound according to claim 1, wherein the urethane compound represented by Formula (1) is obtained by reacting an amine compound with a carboxyl compound, and the obtained urethane compound represented by Formula (1) is then reacted with the carboxylate compound represented by Formula (2), the amine compound being represented by Formula (4):

 (4)

wherein A and n are as defined above, and the carboxyl compound being represented by any one of the following Formulas (5a), (5b), and (5c):

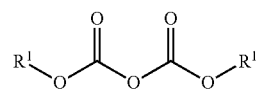 (5a)

wherein $R^1$ is as defined above;

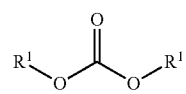 (5b)

wherein $R^1$ is as defined above; and

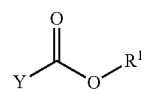 (5c)

wherein $R^1$ is as defined above; and Y represents a halogen atom.

4. The method for producing an amidate compound according to claim 3, wherein the carboxyl compound is a carboxyl compound represented by Formula (5a).

5. The method for producing an amidate compound according to claim 3, wherein the amine compound is an amine compound represented by any one of the following Formulas (4-1), (4-2), and (4-3):

 (4-1)

wherein $R^6$ is as defined above;

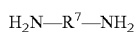 (4-2)

wherein $R^7$ is as defined above; and

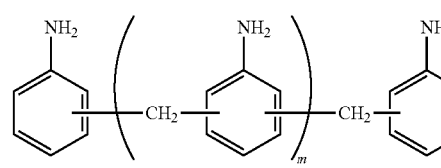 (4-3)

wherein m is an integer of 0 to 4.

6. The method for producing an amidate compound according to claim 1, wherein the urethane compound represented by Formula (1) is obtained by reacting an isocyanate compound with an alcohol compound, and the urethane compound represented by Formula (1) is then reacted with the carboxylate compound represented by Formula (2), the isocyanate compound being represented by Formula (6):

 (6)

wherein A and n are as defined above, and the alcohol compound being represented by Formula (7):

R¹—OH (7)

wherein R¹ is as defined above.

7. The method for producing an amidate compound according to claim 6, wherein the isocyanate compound represented by Formula (6) is an isocyanate compound represented by any one of the following Formulas (6-1), (6-2), and (6-3):

R⁶—NCO (6-1)

wherein R⁶ is a substituted or unsubstituted hydrocarbon group;

OCN—R⁷—NCO (6-2)

wherein R⁷ is a substituted or unsubstituted hydrocarbon group; and

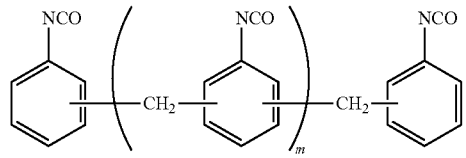 (6-3)

wherein m is an integer of 0 to 4.

8. The method for producing an amidate compound according to claim 1, wherein the carboxylate compound represented by Formula (2) is a carboxylate compound represented by any one of the following Formulas (2-1), (2-2), and (2-3):

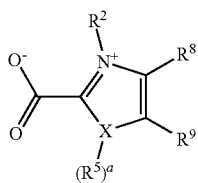 (2-1)

wherein $R^2$, $R^5$, X, and a are as defined above; and $R^8$ and $R^9$ represent a hydrogen atom, or a $C_1$-$C_6$ hydrocarbon group that may contain a heteroatom;

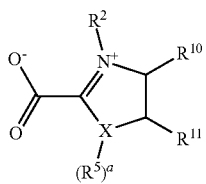 (2-2)

wherein $R^2$, $R^5$, X, and a are as defined above; $R^{10}$ and $R^{11}$ represent a hydrogen atom, or a $C_1$-$C_6$ hydrocarbon group that may contain a heteroatom; and

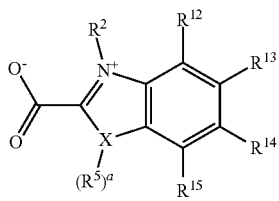 (2-3)

wherein $R^2$, $R^5$, X, and a are as defined above; $R^{12}$, $R^{13}$, $R^{14}$, and $R^{15}$ each represent a hydrogen atom, or a $C_1$-$C_6$ hydrocarbon group that may contain a heteroatom.

9. The method for producing an amidate compound according to claim 1, wherein X is a nitrogen atom.

* * * * *